US007799781B2

(12) United States Patent
Nowak

(10) Patent No.: US 7,799,781 B2
(45) Date of Patent: Sep. 21, 2010

(54) 5,6,7,8-TETRAHYDROPTERIDINE DERIVATIVES AS HSP90 INHIBITORS

(75) Inventor: Thorsten Nowak, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/023,202

(22) Filed: Jan. 31, 2008

(65) Prior Publication Data
US 2008/0194572 A1 Aug. 14, 2008

Related U.S. Application Data

(60) Provisional application No. 60/887,716, filed on Feb. 1, 2007, provisional application No. 60/950,654, filed on Jul. 19, 2007.

(51) Int. Cl.
*C07D 475/00* (2006.01)
*C07D 413/14* (2006.01)
*A61K 31/4985* (2006.01)
*A61K 31/5355* (2006.01)
*A61P 35/00* (2006.01)
*C07D 487/14* (2006.01)

(52) U.S. Cl. .................. 514/234.2; 514/249; 544/118; 544/184; 544/258

(58) Field of Classification Search ................ 544/258, 544/259, 118; 514/249, 234.2
See application file for complete search history.

(56) References Cited

U.S. PATENT DOCUMENTS

| 4,424,351 | A | 1/1984 | Benko |
| 6,514,982 | B1 | 2/2003 | Haddach |
| 6,531,475 | B1 | 3/2003 | Haddach |
| 6,806,272 | B2 | 10/2004 | Bauer |
| 2005/0107343 | A1 | 5/2005 | Kasibhatla |
| 2005/0113340 | A1 | 5/2005 | Kasibhatla |
| 2005/0119282 | A1 | 6/2005 | Kasibhatla |
| 2006/0211702 | A1 | 9/2006 | Oslob |

FOREIGN PATENT DOCUMENTS

| CA | 2588857 | 6/2006 |
| CA | 2608766 | 11/2006 |
| JP | 2000154139 | 6/2000 |
| WO | WO 00/27846 | 5/2000 |
| WO | WO 01/87885 | 11/2001 |
| WO | WO 02/36075 | 5/2002 |
| WO | WO 03/037860 | 5/2003 |
| WO | WO 2005/021552 | 3/2005 |
| WO | WO 2005/028434 | 3/2005 |
| WO | WO 2006/058876 | 6/2006 |
| WO | WO 2006/065703 | 6/2006 |
| WO | WO 2006/084030 | 8/2006 |
| WO | WO 2006/105372 | 10/2006 |
| WO | WO 2006/117669 | 11/2006 |
| WO | WO 2006/122631 | 11/2006 |
| WO | WO 2007/035963 | 3/2007 |
| WO | WO 2007/090844 | 8/2007 |
| WO | WO 2007/092496 | 8/2007 |

OTHER PUBLICATIONS

Ujino, et al., Antiviral Research 74 (2007), A62-A63.*
Hu, et al., J. Virol, Dec. 2004, 13122-13131.*
Miyata, Curr. Pharmaceu. Design, 2005, 11, 1131-1138.*
Rohr, et al., Assn. for Acad. Surg. & Soc. Of University Surgeons, Abstracts, 2007, Abstract #52.*
Bagatell, et al., Mol. Cancer Ther., 2004, 3 (8), 1021-1030.*
Neckers, Trends in Molecular Med., vol. 8, # 4, Apr. 1, 2002, pp. S55-S61.*
Kelland, et al., J. Nat. Can. Inst., vol. 91, # 22, Nov. 17, 1999, 1940-1949.*
Wikipedia, Geldanamycin, http://en.wikipedia.org/wiki/Geldanamycin, downloaded Aug. 21, 2009.*
Sain, et al., Mol. Cancer Ther. 2006; 5(5), May 2006, 1197-1208.*
Albert et al. "415. Pteridine studies. Part XVIII. The reduction of hydroxypteridines" Journal of the Chemical Society 2162-2171 (1962).
Bagatell et al. "Altered Hsp90 function in cancer: a unique therapeutic opportunity" Molecular Cancer Therapeutics 3(8): 1021-1030 (2004).
Baker et al. "Studies on guanosine triphosphate cyclohydrolase I" Chemistry & Biology of Pteridines and Folates 1997, Proceedings of the International Symposium on Pteridines and Folates, Germany, 603-606 (Jun. 15-20, 1997).
Baxter et al. "4,6-Dichloro-5-nitropyrimidine: a versatile building block for the solid-phase synthesis of dihydropteridinones" Tetrahedron Letters 41(42): 8177-8181 (2000).
Beliakoff et al. "Hsp90: an emerging target for breast cancer therapy" Anti-cancer Drugs 15(7): 651-662 (2004).
Blakley "Spectrophotometric studies on the combination of formaldehyde with tetrahydropteroylglutamic acid and other hydropteridines" Biochem Journal 74: 71-82 (1960).
Brook et al. "Hydropteridines. Part III. 5 : 6 : 7 : 8-Tetrahydro-4-methylpteridine" Journal of the Chemical Society 896-900 (1955).
Brook et al. "Hydropteridines. Part IV. 5 : 6 : 7 : 8-Tetrahydropteridine" Journal of the Chemical Society 1-4 (1957).
Buckman et al. "Design synthesis and biological activity of novel purine and bicyclic pyrimidine factor Xa inhibitors" Bioorganic & Medicinal Chemistry Letters 8(16): 2235-2240 (1998).
Cole et al. "Solid-phase synthesis of N-9-subsituted 2,8-diaminopurines" Tetrahedron Letters 47(50): 8897-8900 (2006).
Cullinan et al. "Heat shock protein 90: A unique chemotherapeutic target" Seminars in Oncology 33(4): 457-465 (2006).
Kasibhatla et al. "Rationally designed high-affinity 2-amino-6-halopurine heat shock protein 90 inhibitors that exhibit potent antitumor activity" J Med Chem. 50(12): 2767-2778 (2007).

(Continued)

*Primary Examiner*—James O Wilson
*Assistant Examiner*—Cecilia M Jaisle
(74) *Attorney, Agent, or Firm*—Morgan Lewis & Bockius LLP

(57) ABSTRACT

The present invention relates to compounds that inhibit HSP90 function, processes for their preparation, pharmaceutical compositions containing them as the active ingredient, to their use as medicaments and to their use in the manufacture of medicaments for use in the treatment in warm-blooded animals such as humans of diseases such as for treatment of solid tumors.

19 Claims, No Drawings

OTHER PUBLICATIONS

Makara et al. "Synthesis of bicyclic pyrimidine derivatives as ATP analogues" Journal of Organic Chemistry 66(17): 5783-5789 (2001).

McGill, "Latent inhibitors. Part 8. Synthesis and evaluation of some mechanism-based inhibitors of dihydrofolate reductase" Journal of the Chemical Society 11: 1299-1304 (1992).

Montgomery et al "Synthesis of potential anticancer agents. XXII. 9-Aminohypoxanthine and related compounds" Journal of the American Chemical Society 82: 4592-4596 (1960).

Nagashima et al. "Solution-phase parallel synthesis of an N-alkylated dihydropteridinone library from fluorous amino acids" Journal of Combinatorial Chemistry 6(6): 942-949 (2004).

Pfleiderer et al. "Pteridines. XLV. A simple synthetic approach to 8-substituted 5,6,7,8-tetrahydro- and 7,s-dihydropterins" Chemische Berichte. 104(7): 2293-2312 (1971) (Translation enclosed).

Sabat et al. "The Development of Novel C-2, C-8, and N-9 trisubstituted purines as inhibitors of TNF-$\alpha$ production" Bioorganic & Medicinal Chemistry Letters 16(16): 4360-4365 (2006).

Solit et al. "17-Allylamino-17-demethoxygeldanamycin induces the degradation of androgen receptor and HER-2/neu and inhibits the growth of prostate cancer xenografts" Clinical Cancer Research 8: 986-993 (2002).

Vilenchik et al. "Targeting wide-range oncogenic transformation via PU24FCl, a specific inhibitor of tumor Hsp90" Chemistry & Biology 11: 787-797 (2004).

Solit et al. "Development and application of Hsp90 inhibitors" Drug Discovery Today 13(1-2):38-43 (2008).

Mahalingam et al. "Targeting HSP90 for cancer therapy" British Journal of Cancer 100(10):1523-1529 (2009).

* cited by examiner

5,6,7,8-TETRAHYDROPTERIDINE DERIVATIVES AS HSP90 INHIBITORS

RELATED APPLICATIONS

This application claims the benefit under 35 USC §119(a)-(d) of U.S. Provisional Patent Application No. 60/887,716, filed on Feb. 1, 2007; and U.S. Provisional Patent Application No. 60/950,654, filed on Jul. 19, 2007.

FIELD OF THE INVENTION

The present invention relates to novel 5,6,7,8-tetrahydropteridine derivatives, their pharmaceutical compositions and methods of use. In addition, the present invention relates to therapeutic methods for the treatment and prevention of cancers and to the use of these 5,6,7,8-tetrahydropteridine derivatives in the manufacture of medicaments for use in the treatment and prevention of cancers.

BACKGROUND OF THE INVENTION

Heat shock proteins (hereafter HSP) are chaperone proteins which regulate the conformational stability and maturation of many cellular proteins. Numerous HSP's are known and are classified according to their molecular weight. HSP90 is a 90 k Dalton protein chaperone that plays a central role in regulating, for example, protein homeostasis. HSP90 regulates the stability of certain proteins ("client proteins") and maintains them in the appropriate three-dimensional conformation so they can perform their cellular functions. In humans, there are two HSP90 isoforms in the cytosol, HSP90α and HSP90β. These proteins are closely related and, to date, no differences in their activities have been identified.

In addition to normal cellular function, certain HSP90 client proteins are associated with abnormal cellular function. For example many of the proteins stabilized by HSP90 are oncoproteins and cell-signalling proteins important in cancer cell proliferation and cancer cell survival, including many kinases and transcription factors including, but not limited to ErbB2, Raf-1, Akt/PKB, mutant p53, v-src, c-src, MEK, Focal adhesion kinase (FAK), P210bcr-abl, CDK4 and Epidermal growth factor receptor (EGFR).

Accordingly, HSP90 has been implicated in cancer, and other diseases. HSP90 is therefore an important target for drugs that inhibit the function of HSP90 and its role in diseases such as cancer.

HSP90 is over expressed in cancer cells and is thought to be involved in various cellular processes, such as cell proliferation, differentiation and apoptosis. Inhibition of HSP90 is expected to result in the blockade of multiple cancer-causing pathways by promoting the degradation of many oncogenic HSP90 client proteins, therefore HSP90 inhibitors are expected to provide broad-spectrum antitumour activity.

The anti-cancer effects of HSP90 inhibition have been demonstrated both in vitro and in vivo for a variety of different hematologic and solid tumours including multiple myeloma (Vilenchik et al., Chem & Bio, 2004 Jun. 11, 787-797; Solit et al., Clin Can Res, 2002 May, 8, 986-993, Beliocoff et al., Anticancer Drugs 2004 August; 15 (7):651-62; Bagatel et al., Molecular Cancer Therapeutics, 2004 August; 3 (8):1021-30; and Cullinan et al., Seminars in Oncology, 2006 August; 33 (4):457-65).

HSP90 inhibitors may be useful in the treatment of other disorders, for example inflammatory diseases, infections, autoimmune disorders, stroke, ischemia, cardiac disorders, neurological disorders, fibrogenetic disorders and metabolic diseases.

Various HSP90 inhibitors are known. The benzoquinone ansamycin antibiotic, 17-allylamino-17-demethoxygeldanamycin (17-AAG) and derivatives thereof are currently in clinical trials an anticancer agent in patients with solid tumour disease.

WO 03/037860 discloses certain purine derivatives as HSP90 inhibitors.

WO 2005/021552 discloses certain pyrimidothiophene derivatives as HSP90 inhibitors.

WO 2005/028434 discloses certain pyrimidine derivatives as HSP90 inhibitors.

WO 2006/117669 discloses certain resorcinol pyrimidine derivatives as HSP90 inhibitors.

WO 2006/122631 discloses certain quinazoline derivatives as HSP90 inhibitors.

WO 2006/105372 discloses certain alkynyl pyrrolo[2,3-d] pyrimidine derivatives as HSP90 inhibitors.

WO 2007/035963 discloses certain heterocyclic compounds, such as 2-aminopurines, pyrazolopyrimidines, pyrrolopyrimidines, alkynyl pyrrolopyrimidine and triazopyrimidines as HSP90 inhibitors.

WO 2007/092496 discloses certain 7,9-dihydropurin-8-one compounds as HSP90 inhibitors.

Kasibhatla et al. (J. Med. Chem., 2007, 50 (12), 2767-2778) discloses certain purine derivatives as HSP90 inhibitors.

There remains, however, a need to develop alternative HSP90 inhibitors.

SUMMARY OF THE INVENTION

In accordance with the present invention, the applicants have discovered novel 5,6,7,8-tetrahydropteridine compounds, or pharmaceutically acceptable salts thereof, which possess HSP90 inhibitory activity and are accordingly useful for their anti-proliferation and/or pro-apoptotic (such as anticancer) activity and in methods of treatment of the human or animal body. The invention also relates to processes for the manufacture of said 5,6,7,8-tetrahydropteridine compounds, or pharmaceutically acceptable salts thereof, to pharmaceutical compositions containing them and to their use in the manufacture of medicaments for use in the production of, for example, an anti-proliferative and/or pro-apoptotic effect in warm-blooded animals such as man.

Also in accordance with the present invention the applicants provide methods of using such 5,6,7,8-tetrahydropteridine compounds, or pharmaceutically acceptable salts thereof, in the treatment of cancer.

The compounds claimed in this invention are may to be of value in the treatment of disease states associated with cell proliferation and other conditions such as cancers (both solid tumours and leukaemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases, ocular diseases with retinal vessel proliferation, infections, autoimmune disorders, stroke, ischemia, cardiac disorders, neurological disorders and metabolic diseases.

Furthermore, the compounds, or pharmaceutically acceptable salts thereof, of the invention are expected to be of value in the treatment or prophylaxis of cancers including oesophageal cancer, myeloma, hepatocellular, pancreatic, cervical cancer, ewings tumour, neuroblastoma, kaposis sarcoma, ovarian cancer, endometrial cancer, uterine cancer, vulval cancer, breast cancer, colorectal cancer, prostate cancer, bladder cancer, melanoma, lung cancer—non small cell lung cancer (NSCLC), and small cell lung cancer (SCLC), gastric cancer, head and neck cancer, renal cancer, bile duct cancer, bone cancer, neuronal cancer, skin cancer, testicular cancer, lymphoma and leukaemia, multiple myeloma or lymphoma; particularly ovarian cancer, breast cancer, colorectal cancer, prostate cancer and lung cancer—NSCLC and SCLC; more particularly melanoma, breast, ovarian, lung and gastric cancers.

DETAILED DESCRIPTION OF THE INVENTION

Accordingly the present invention provides a compound of the formula I:

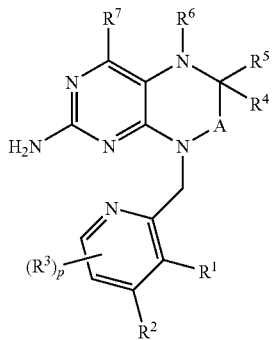

wherein:
$R^1$, $R^2$ and $R^3$ are independently selected from H, halo, cyano, nitro or a group of the formula:

—$X^1$—$R^8$, wherein $X^1$ is a direct bond, O, S or $NR^{8a}$, wherein $R^{8a}$ is H or $C_{1-6}$alkyl, and $R^8$ is selected from H, $C_{1-6}$alkyl, $C_{2-6}$alkenyl, $C_{3-7}$cycloalkyl and $C_{2-6}$alkynyl, and wherein $R^1$, $R^2$ and $R^3$ may independently of each other be optionally substituted on carbon by one or more substituents selected from halo, hydroxy, amino, N—($C_{1-6}$alkyl)amino, N,N—($C_{1-6}$alkyl)$_2$amino, $C_{1-6}$alkoxy, $C_{3-7}$cycloalkyl, carbamoyl, N—($C_{1-6}$alkyl)carbamoyl and N,N—($C_{1-6}$alkyl)$_2$carbamoyl;

p is 1 or 2;

A is $NR^9$ or $CR^{10}R^{11}$;

$R^4$ and $R^{10}$ are independently selected from H, $C_{1-6}$alkyl, $C_{2-6}$alkenyl and $C_{2-6}$alkynyl, wherein $R^4$ and $R^{10}$ may, independently of each other, be optionally substituted on carbon by halo, hydroxy, amino, $C_{1-6}$alkoxy, N—($C_{1-6}$alkyl)amino and N,N—($C_{1-6}$alkyl)$_2$amino;

$R^5$ and $R^{11}$ are independently selected from H, cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, $C_{1-6}$alkylsulfonylaminocarbonyl, carbocyclyl-$X^2$—, heterocyclyl-$X^3$— or heteroaryl-$X^4$—, wherein $R^5$ and $R^{11}$ may independently of each other be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^5$ and $R^{11}$ may optionally bear 1 or 2 oxo or thioxo substituents;

and wherein any carbocyclyl, heterocyclyl or heteroaryl group within $R^5$ and $R^{11}$ may optionally bear a $C_{1-3}$alkylenedioxy group;

or $R^4$ and $R^5$ together form oxo (=O);
or $R^{10}$ and $R^{11}$ together form oxo (=O);
or one of the following pairs of substituents (i) $R^4$ and $R^6$, (ii) $R^4$ and $R^{10}$ or (iii) $R^4$ and $R^9$ together form a bond;

$R^6$ and $R^9$ are independently selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, carbocyclyl-$X^5$—, heterocyclyl-$X^6$— or heteroaryl-$X^7$—, wherein $X^5$, $X^6$ and $X^7$ are independently selected from a direct bond, —C(O)—, —N($R^{12}$)C(O)— and —SO$_2$—;

wherein $R^{12}$ is selected from hydrogen or $C_{1-4}$alkyl, and wherein $R^6$ and $R^9$ may, independently of each other, be optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ and $R^9$ may optionally bear 1 or 2 oxo or thioxo substituents;

and wherein any carbocyclyl, heterocyclyl or heteroaryl group within $R^6$ and $R^9$ may optionally bear a $C_{1-3}$alkylenedioxy group;

$R^7$ is selected from H, halo, hydroxy, trifluoromethoxy, mercapto, $C_{1-6}$alkyl, $C_{2-6}$alkenyl, $C_{2-6}$alkynyl, $C_{1-6}$alkoxy, $C_{1-6}$alkylS(O)$_a$ wherein a is 0 to 2, wherein $R^7$ may be optionally substituted on carbon by one or more $R^{15}$;

$R^{13}$, $R^{15}$ and $R^{16}$ are independently selected from halo, nitro, cyano, hydroxy, trifluoromethoxy, amino, carboxy, carboxyamino, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{13}$, $R^{15}$ and $R^{16}$ may be optionally substituted on carbon by one or more $R^{18}$, and wherein if said heterocyclyl or heteroaryl contains an —NH— moiety that nitrogen may be optionally substituted by a group selected from $R^{19}$, and wherein any heterocyclyl group within $R^{13}$, $R^{15}$ and $R^{16}$ may optionally bear 1 or 2 oxo or thioxo substituents and wherein any carbocyclyl, heterocyclyl or heteroaryl group within $R^{13}$, $R^{15}$ and $R^{16}$ may optionally bear a $C_{1-3}$alkylenedioxy group;

$R^{14}$, $R^{17}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$, $R^{17}$ and $R^{19}$ independently of each other may be optionally substituted on carbon by one or more $R^{20}$;

$X^2$, $X^3$ and $X^4$ are independently selected from a direct bond, —C(O)— and —N($R^{22}$)C(O)—; wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— and —N(R$^{25}$)SO$_2$—; wherein R$^{21}$, R$^{22}$, R$^{23}$, R$^{24}$ and R$^{25}$ are independently selected from hydrogen or C$_{1-4}$alkyl and q is 0-2;

R$^{18}$ is selected from halo, nitro, cyano, hydroxy, trifluoromethoxy, amino, carboxy, carbamoyl, mercapto, sulfamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulfamoyl, N,N—(C$_{1-6}$alkyl)$_2$sulfamoyl, C$_{1-6}$alkylsulfonylamino, carbocyclyl, heterocyclyl or heteroaryl; wherein R$^{18}$ may be optionally substituted on carbon by one or more R$^{25}$;

and wherein if any of said heterocyclyl or heteroaryl contains an —NH— moiety that nitrogen may be optionally substituted by a group selected from R$^{26}$;

and wherein any heterocyclyl group within R$^{18}$ may optionally bear 1 or 2 oxo or thioxo substituents;

and wherein any carbocyclyl, heterocyclyl or heteroaryl group within R$^{18}$ may optionally bear a C$_{1-3}$alkylenedioxy group;

R$^{26}$ is selected from C$_{1-6}$alkyl, C$_{1-6}$alkanoyl, C$_{1-6}$alkylsulfonyl, C$_{1-6}$alkoxycarbonyl, carbamoyl, N—(C$_{1-6}$alkyl)carbamoyl, N,N—(C$_{1-6}$alkyl)$_2$carbamoyl, benzyl, benzyloxycarbonyl, benzoyl and phenylsulfonyl; wherein R$^{26}$ may be optionally substituted on carbon by one or more R$^{27}$; and R$^{20}$, R$^{25}$ and R$^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

The present invention further provides a compound of the formula I, wherein:

R$^1$, R$^2$ and R$^3$ are independently selected from H, halo or a group of the formula:

—X$^1$—R$^8$, wherein X$^1$ is a direct bond, O, S or NR$^{8a}$, wherein R$^{8a}$ is H or C$_{1-6}$alkyl, and R$^8$ is selected from H, C$_{1-6}$alkyl, C$_{2-6}$alkenyl, C$_{3-7}$cycloalkyl and C$_{2-6}$alkynyl, and wherein R$^1$, R$^2$ and R$^3$ may independently of each other be optionally substituted on carbon by one or more substituents selected from halo, hydroxy, amino, N—(C$_{1-6}$alkyl)amino, N,N—(C$_{1-6}$alkyl)$_2$amino, C$_{1-6}$alkoxy, C$_{3-7}$cycloalkyl, carbamoyl, N—(C$_{1-6}$alkyl)carbamoyl and N,N—(C$_{1-6}$alkyl)$_2$carbamoyl;

p is 1 or 2;

A is NR$^9$ or CR$^{10}$R$^{11}$;

R$^4$ and R$^{10}$ are independently selected from H, C$_{1-6}$alkyl, C$_{2-6}$alkenyl and C$_{2-6}$alkynyl, wherein R$^4$ and R$^{10}$ may, independently of each other, be optionally substituted on carbon by halo, hydroxy, amino, C$_{1-6}$alkoxy, N—(C$_{1-6}$alkyl)amino and N,N—(C$_{1-6}$alkyl)$_2$amino;

R$^5$ and R$^{11}$ are independently selected from H, cyano, carboxy, carbamoyl, C$_{1-6}$alkyl, C$_{2-6}$alkenyl, C$_{2-6}$alkynyl, C$_{1-6}$alkanoyl, N—(C$_{1-6}$alkyl)carbamoyl, N,N—(C$_{1-6}$alkyl)$_2$carbamoyl, N—(C$_{1-4}$alkoxy)carbamoyl, N—(C$_{1-4}$alkyl)-N—(C$_{1-4}$alkoxy)carbamoyl, C$_{1-6}$alkoxycarbonyl, C$_{1-6}$alkylsulfonylaminocarbonyl, carbocyclyl-X$^2$—, heterocyclyl-X$^3$— or heteroaryl-X$^4$—, wherein R$^5$ and R$^{11}$ may independently of each other be optionally substituted on carbon by one or more R$^{13}$; and wherein if any of said heterocyclyl or heteroaryl contains an —NH— moiety that nitrogen may be optionally substituted by a group selected from R$^{14}$, and wherein any heterocyclyl group within R$^5$ and R$^{11}$ may optionally bear 1 or 2 oxo or thioxo substituents;

and wherein any carbocyclyl, heterocyclyl or heteroaryl group within R$^5$ and R$^{11}$ may optionally bear a C$_{1-3}$alkylenedioxy group;

or R$^4$ and R$^5$ together form oxo (=O);

or R$^{10}$ and R$^{11}$ together form oxo (=O);

or one of the following pairs of substituents (i) R$^4$ and R$^6$, (ii) R$^4$ and R$^{10}$ or (iii) R$^4$ and R$^9$ together form a bond;

R$^6$ and R$^9$ are independently selected from H, C$_{1-6}$alkyl, C$_{2-6}$alkenyl, C$_{2-6}$alkynyl, C$_{1-6}$alkanoyl, C$_{1-6}$alkylsulfonyl, C$_{1-6}$alkoxycarbonyl, carbamoyl, N—(C$_{1-6}$alkyl)carbamoyl, N,N—(C$_{1-6}$alkyl)$_2$carbamoyl, carbocyclyl-X$^5$—, heterocyclyl-X$^6$— or heteroaryl-X$^7$—, wherein X$^5$, X$^6$ and X$^7$ are independently selected from a direct bond, —C(O)—, —N(R$^{12}$)C(O)— and —SO$_2$—; wherein R$^{12}$ is selected from hydrogen or C$_{1-4}$alkyl, and wherein R$^6$ and R$^9$ may, independently of each other, be optionally substituted on carbon by one or more R$^{16}$; and wherein if any of said heterocyclyl or heteroaryl contains an —NH— moiety that nitrogen may be optionally substituted by a group selected from R$^{17}$, and wherein any heterocyclyl group within R$^6$ and R$^9$ may optionally bear 1 or 2 oxo or thioxo substituents;

and wherein any carbocyclyl, heterocyclyl or heteroaryl group within R$^6$ and R$^9$ may optionally bear a C$_{1-3}$alkylenedioxy group;

R$^7$ is selected from H, halo, hydroxy, trifluoromethoxy, mercapto, C$_{1-6}$alkyl, C$_{2-6}$alkenyl, C$_{2-6}$alkynyl, C$_{1-6}$alkoxy, C$_{1-6}$alkylS(O)$_a$ wherein a is 0 to 2, wherein R$^7$ may be optionally substituted on carbon by one or more R$^{15}$;

R$^{13}$, R$^{15}$ and R$^{16}$ are independently selected from halo, nitro, cyano, hydroxy, trifluoromethoxy, amino, carboxy, carbamoyl, mercapto, sulfamoyl, ureido, C$_{1-6}$alkyl, C$_{2-6}$alkenyl, C$_{2-6}$alkynyl, C$_{1-6}$alkoxy, C$_{2-6}$alkenyloxy, C$_{2-6}$alkynyloxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, N'—(C$_{1-6}$alkyl)ureido, N',N'—(C$_{1-6}$alkyl)$_2$ureido, N,N',N'—(C$_{1-6}$alkyl)$_3$ureido, C$_{1-6}$alkylS(O)$_a$ wherein a is 0 to 2, C$_{1-6}$alkoxycarbonyl, N—(C$_{1-6}$alkyl)sulfamoyl, N,N—(C$_{1-6}$alkyl)$_2$sulfamoyl, C$_{1-6}$alkylsulfonylamino, carbocyclyl-X$^8$—, heterocyclyl-X$^9$— or heteroaryl-X$^{10}$—, and wherein R$^{13}$, R$^{15}$ and R$^{16}$ may be optionally substituted on carbon by one or more R$^{18}$;

and wherein if said heterocyclyl or heteroaryl contains an —NH— moiety that nitrogen may be optionally substituted by a group selected from R$^{19}$, and wherein any heterocyclyl group within R$^{13}$, R$^{15}$ and R$^{16}$ may optionally bear 1 or 2 oxo or thioxo substituents and wherein any carbocyclyl, heterocyclyl or heteroaryl group within R$^{13}$, R$^{15}$ and R$^{16}$ may optionally bear a C$_{1-3}$alkylenedioxy group;

R$^{14}$, R$^{17}$ and R$^{19}$ are independently selected from C$_{1-6}$alkyl, C$_{1-6}$alkanoyl, C$_{1-6}$alkylsulfonyl, C$_{1-6}$alkoxycarbonyl, carbamoyl, N—(C$_{1-6}$alkyl)carbamoyl, N,N—(C$_{1-6}$alkyl)$_2$carbamoyl, benzyl, benzyloxycarbonyl, benzoyl and phenylsulfonyl; wherein $R^{14}$, $R^{17}$ and $R^{19}$ independently of each other may be optionally substituted on carbon by one or more $R^{20}$;

$X^2$, $X^3$ and $X^4$ are independently selected from a direct bond, —C(O)— and —N($R^{22}$)C(O)—; wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— and —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

and wherein any carbocyclyl, heterocyclyl or heteroaryl group within $R^{18}$ may optionally bear a $C_{1-3}$alkylenedioxy group;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

Unless otherwise stated, the following terms used in this specification and claims have the following meanings.

DEFINITIONS

Where optional substituents are chosen from "one or more" groups it is to be understood that this definition includes all substituents being chosen from one of the specified groups or the substituents being chosen from two or more of the specified groups.

"halo" means fluoro, chloro, bromo or iodo.

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl, sec-butyl, n-pentyl, n-hexyl and the like. However, references to individual alkyl groups such as 'propyl' are specific for the straight-chained version only and references to individual branched chain alkyl groups such as 'isopropyl' are specific for the branched-chain version only. A similar convention applies to other radicals.

The term "$C_{m-n}$" or "$C_{m-n}$ group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "$C_{1-6}$alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"$C_{2-6}$alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"$C_{2-6}$alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"$C_{3-7}$cycloalkyl" means a hydrocarbon ring containing from 3 to 7 carbon atoms, for example, cyclopropyl, cyclobutyl, cyclopentyl, cyclohexyl, cycloheptyl or bicyclo[2.2.1]heptyl.

"$C_{3-7}$cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"$C_{3-7}$cycloalkyl-$C_{1-6}$alkylene" means a $C_{3-7}$cycloalkyl group covalently attached to a $C_{1-6}$alkylene group, both of which are defined herein.

A "carbocyclyl" is a saturated, partially saturated or unsaturated, mono or bicyclic carbon ring that contains 3-12 atoms; wherein a —CH$_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include $C_{3-7}$cycloalkyl, $C_{3-7}$cycloalkenyl and aryl, for example "carbocyclyl" includes cyclopropyl, cyclobutyl, 1-oxocyclopentyl, cyclopentyl, cyclopentenyl, cyclohexyl, cyclohexenyl, cyclohexenyl, 4-oxocyclohex-1-yl, 3-oxocyclohept-5-en-1-yl, phenyl, naphthyl, tetralinyl, indanyl or 1-oxoindanyl.

The term "heterocyclyl" means a non-aromatic saturated or partially unsaturated monocyclic, fused, bridged, or spiro bicyclic heterocyclic ring system(s). Monocyclic heterocyclic rings contain from about 3 to 12 ring atoms, with from 1 to 5 heteroatoms selected from N, O, and S, and suitably from 3 to 7 member atoms, in the ring (for example a 5 or 6-membered monocyclic ring containing 1 or 2 heteroatoms selected from O, S and N). Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers (oxiranes) such as ethyleneoxide, tetrahydrofuran, dioxane. Heterocycles containing nitrogen include, for example, azetidine, pyrrolidine, piperidine, piperazine, tetrahydrotriazine, tetrahydropyrazole, and the like. Typical sulfur containing heterocycles include tetrahydrothiophene, dihydro-1,3-dithiol-2-yl, and hexahydrothiepin-4-yl. Other heterocycles include dihydro-oxathiol-4-yl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothiophene. A suitable value for a heterocyclyl group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

The term "heterocyclyl" used herein also covers polycyclic ring systems containing one or more heteroatoms selected from O, S and N, wherein at one or more ring is aromatic and at least one of the other rings is a non-aromatic, saturated or partially unsaturated ring optionally for example partially saturated bicyclic heteroaryl rings such as 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Particular heterocycles include oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, aziridinyl, azetidinyl, pyrrolinyl, pyrrolidinyl, imidazolinyl, imidazolidinyl, pyrazolinyl, pyrazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, 2-azabicyclo[2.2.1]heptyl, quinuclidinyl, chromanyl, isochromanyl, indolinyl, isoindolinyl, dihydropyridinyl, tetrahydropyridinyl, dihydropyrimidinyl or tetrahydropyrimidinyl. Other particular heterocycles include azetidinyl, tetrahydrofuranyl, tetrahydropyranyl, tetrahydrothiopyranyl, pyrrolinyl, pyrrolidinyl, morpholinyl, piperidinyl, piperazinyl, indolinyl or isoindolinyl.

As the skilled person would appreciate, any heterocycle may be linked to another group via. any suitable atom, such as via. a carbon or nitrogen atom.

A suitable value for such a heterocyclyl group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 4-oxo-1,4-dihydropyridinyl, 2,5-dioxopyrrolidinyl, 2,5-dioxoimidazolidinyl or 2,6-dioxopiperidinyl.

"Heterocyclyl-$C_{1-6}$alkyl" means a heterocyclyl group covalently attached to a $C_{1-6}$alkylene group, both of which are defined herein.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like.

The term "aryl-$C_{1-6}$alkyl" means an aryl group covalently attached to a $C_{1-6}$alkyl group, both of which are defined herein. Examples of aryl-$C_{1-6}$alkyl groups include benzyl, phenylethyl, and the like The term "heteroaryl" means an aromatic mono-, bi-, or polycyclic ring incorporating one or more (for example 1-4) heteroatoms selected from N, O, and S. The term heteroaryl includes both monovalent species and divalent species. Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl.

References herein to a "6,5" or "6,6" aryl or heteroaryl ring systems refer to 5 membered ring fused to another 6 membered ring such as a benzothienyl ring (a 6,5 ring); or one 6 membered ring fused to another 6 membered ring such as a naphthyl, quinolyl or quinazolinyl ring (a 6,6 ring). Unless stated otherwise, a 6,5 heteroaryl group may be attached via the 5 or the 6 membered ring.

"Heteroaryl-$C_{1-6}$alkyl" means an heteroaryl group covalently attached to a $C_{1-6}$alkyl group, both of which are defined herein. Examples of heteroaryl-$C_{1-6}$alkyl groups include pyridin-3-ylmethyl, 3-(benzofuran-2-yl)propyl, and the like.

"Haloalkyl" means alkyl substituted with one or more same or different halo atoms, e.g., —$CH_2Cl$, —$CF_3$, —$CH_2CF_3$, —$CH_2CCl_3$, and the like.

Examples for the substituents within the compound of formula I include:—

| | |
|---|---|
| for halo | fluoro, chloro, bromo and iodo; |
| for $C_{1-6}$alkyl: | methyl, ethyl, propyl, isopropyl and tert-butyl; |
| for $C_{2-6}$alkenyl: | vinyl, isopropenyl, allyl and but-2-enyl; |
| for $C_{2-6}$alkynyl: | ethynyl, 2-propynyl and but-2-ynyl; |
| for $C_{1-6}$alkoxy: | methoxy, ethoxy, propoxy, isopropoxy and butoxy; |
| for $C_{2-6}$alkenyloxy: | vinyloxy and allyloxy; |
| for $C_{2-6}$alkynyloxy: | ethynyloxy and 2-propynyloxy; |
| for $C_{1-6}$alkylthio: | methylthio, ethylthio and propylthio; |
| for $C_{1-6}$alkylsulfinyl: | methylsulfinyl and ethylsulfinyl; |
| for $C_{1-6}$alkylsulfonyl: | methylsulfonyl and ethylsulfonyl; |
| for N-($C_{1-6}$alkyl)amino: | methylamino, ethylamino, propylamino, isopropylamino and butylamino; |
| for N,N-($C_{1-6}$alkyl)$_2$amino: | dimethylamino, diethylamino, N-ethyl-N-methylamino and diisopropylamino; |
| for $C_{1-6}$alkoxycarbonyl: | methoxycarbonyl, ethoxycarbonyl, propoxycarbonyl and tert-butoxycarbonyl; |
| for N-($C_{1-6}$alkyl)carbamoyl: | N-methylcarbamoyl, N-ethylcarbamoyl and N-propylcarbamoyl; |

| | |
|---|---|
| for N,N-(C$_{1-6}$alkyl)$_2$carbamoyl: | N,N-dimethylcarbamoyl, N-ethyl-N-methylcarbamoyl and N,N-diethylcarbamoyl; |
| for C$_{1-6}$alkanoyl: | formyl, acetyl and propionyl; |
| for C$_{1-6}$alkanoyloxy: | acetoxy and propionyloxy; |
| for C$_{1-6}$alkanoylamino: | acetamido and propionamido; |
| for N-(C$_{1-6}$alkyl)-C$_{1-6}$alkanoylamino: | N-methylacetamido and N-methylpropionamido; |
| for N-(C$_{1-6}$alkyl)sulfamoyl: | N-methylsulfamoyl and N-ethylsulfamoyl; |
| for N,N-(C$_{1-6}$alkyl)$_2$sulfamoyl: | N,N-dimethylsulfamoyl; |
| for C$_{1-6}$alkylsulfonylamino: | methanesulfonylamino and ethanesulfonylamino; |
| for N-(C$_{1-6}$alkyl)-C$_{1-6}$alkylsulfonylamino: | N-methylmethanesulfonylamino and N-methylethanesulfonylamino; |
| for C$_{1-6}$alkylsulfonylaminocarbonyl: | methylsulfonylaminocarbonyl; |
| for N'-(C$_{1-6}$alkyl)ureido: | N'-methylureido and N'-ethylureido; |
| for N',N'-di-[(1-6C)alkyl]ureido: | N',N'-dimethylureido and N'-methyl-N'-ethylureido; |
| for N-(1-6C)alkylureido: | N-methylureido and N-ethylureido; |
| for N,N'-di-[(1-6C)alkyl]ureido: | N,N'-dimethylureido, N-methyl-N'-ethylureido and N-ethyl-N'-methylureido; |
| for N,N',N'-di-[(1-6C)alkyl]ureido: | N,N',N'-trimethylureido; |
| for amino-C$_{1-6}$alkyl: | aminomethyl, 2-aminoethyl, 1-aminoethyl and 3-aminopropyl; |
| for C$_{1-6}$alkylamino-C$_{1-6}$alkyl: | methylaminomethyl, ethylaminomethyl, 1-methylaminoethyl, 2-methylaminoethyl, 2-ethylaminoethyl and 3-methylaminopropyl; |
| for N,N-(C$_{1-6}$alkyl)$_2$amino-C$_{1-6}$alkyl: | dimethylaminomethyl, diethylaminomethyl, 1-dimethylaminoethyl, 2-dimethylaminoethyl and 3-dimethylaminopropyl; |
| for hydroxy-C$_{1-6}$alkyl: | hydroxymethyl, 2-hydroxyethyl, 1-hydroxyethyl and 3-hydroxypropyl; |
| for C$_{1-6}$alkoxy-C$_{1-6}$alkyl: | methoxymethyl, ethoxymethyl, 1-methoxyethyl, 2-methoxyethyl, 2-ethoxyethyl and 3-methoxypropyl; |
| for cyano-C$_{1-6}$alkyl: | cyanomethyl, 2-cyanoethyl, 1-cyanoethyl and 3-cyanopropyl; |
| for mercapto-(1-6C)alkyl: | mercaptomethyl, 2-mercaptoethyl, 1-mercaptoethyl and 3-mercaptopropyl; |
| for C$_{1-6}$alkylthio-C$_{1-6}$alkyl: | methylthiomethyl, ethylthiomethyl, 2-methylthioethyl, 1-methylthioethyl and 3-methylthiopropyl; |
| for C$_{1-6}$alkylsulfinyl-C$_{1-6}$alkyl: | methylsulfinylmethyl, ethylsulfinylmethyl, 2-methylsulfinylethyl, 1-methylsulfinylethyl and 3-methylsulfinylpropyl; |
| for C$_{1-6}$alkylsulfonyl-C$_{1-6}$alkyl: | methylsulfonylmethyl, ethylsulfonylmethyl, 2-methylsulfonylethyl, 1-methylsulfonylethyl and 3-methylsulfonylpropyl; |
| for C$_{1-6}$alkanoylamino-C$_{1-6}$alkyl: | acetamidomethyl, propionamidomethyl and 2-acetamidoethyl; |
| for ureido-C$_{1-6}$alkyl: | ureidomethyl, 2-ureidoethyl and 1-ureidoethyl; |
| for N'-(C$_{1-6}$alkyl)ureido-C$_{1-6}$alkyl: | N'-methylureidomethyl, 2-(N'-methylureido)ethyl and 1-(N'-methylureido)ethyl; |
| for N',N'-(C$_{1-6}$alkyl)$_2$ureido-C$_{1-6}$alkyl: | N',N'-dimethylureidomethyl, 2-(N',N'-dimethylureido)ethyl and 1-(N',N'-dimethylureido)ethyl; |
| for N-(C$_{1-6}$alkyl)ureido-C$_{1-6}$alkyl: | N-methylureidomethyl, 2-(N-methylureido)ethyl and 1-(N-methylureido)ethyl; |
| for N,N'-(C$_{1-6}$alkyl)$_2$ureido-C$_{1-6}$alkyl: | N,N'-dimethylureidomethyl, 2-(N,N'-dimethylureido)ethyl and 1-(N,N'-dimethylureido)ethyl; |
| for N,N',N'-(C$_{1-6}$alkyl)$_3$ureido-C$_{1-6}$alkyl: | N,N',N'-trimethylureidomethyl, 2-(N,N',N'-trimethylureido)ethyl and 1-(N,N',N'-trimethylureido)ethyl; |
| for carboxy-C$_{1-6}$alkyl: | carboxymethyl, 1-carboxyethyl, 2-carboxyethyl, 3-carboxypropyl and 4-carboxybutyl; |
| for C$_{1-6}$alkoxycarbonylamino-C$_{1-6}$alkyl: | methoxycarbonylaminomethyl, ethoxycarbonylaminomethyl, tert-butoxycarbonylaminomethyl and 2-methoxycarbonylaminoethyl. |

The term "$C_{1-3}$alkylenedioxy" includes for example, methylenedioxy, ethylidenedioxy, isopropylidenedioxy or ethylenedioxy and the oxygen atoms thereof occupy adjacent ring positions.

The term "optionally substituted" refers to either groups, structures, or molecules that are substituted and those that are not substituted.

When, as defined herein that, for example, $R^6$ or $R^9$ is carbocyclyl-$X^5$—, heterocyclyl-$X^6$— or heteroaryl-$X^7$—, and, for example, $X^5$, $X^6$ or $X^7$ is a —$N(R^{12})C(O)$-linking group, it is the nitrogen atom, not the carbon atom, of the —$N(R^{12})C(O)$— linking group which is attached to the carbocyclyl, heterocyclyl or heteroaryl group. The same principle applies to the other groups defined herein, for example when, for example, $R^5$ or $R^{11}$ is, for example, heterocyclyl-$X^3$— and $X^3$ is —$N(R^{22})C(O)$— the nitrogen atom of the —$N(R^{22})C(O)$— linker group is attached to the heterocyclyl. As will be realised, when for example, heterocyclyl-$X^3$— is heterocyclyl-$N(R^{22})C(O)$— and said heterocyclyl group is attached to the —$N(R^{22})C(O)$— group by a ring carbon. Similarly, when $R^5$ or $R^{11}$ is heterocyclyl-$X^3$— and $X^3$ is a direct bond, the heterocyclyl group is attached to the 5,6,7,8-tetrahydropteridine ring by a ring carbon atom in the heterocyclyl group.

In structural formula I, it is to be understood that where it is stated that "one of the following pairs of substituents (i) $R^4$ and $R^6$, (ii) $R^4$ and $R^{10}$ or (iii) $R^4$ and $R^9$ together form a bond" only 1 bond is formed in the compound of the formula I, to give compounds of the following formulae:

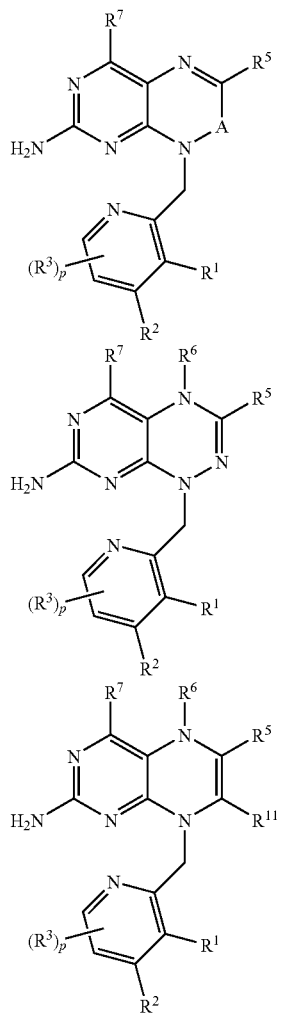

In structural formula I, it is to be understood that where it is stated that "$R^4$ and $R^5$ together form oxo (=O), or $R^{10}$ and $R^{11}$ together form oxo (=O), the oxo group is attached to the ring for to give, for example, a compound of the formula:

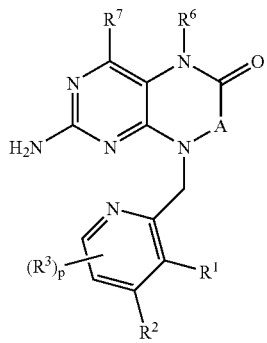

In structural formula I, it is to be understood that where it is stated that the compound of formula I may be in the form of an N-oxide of the compound of formula I, this refers to a nitrogen of a heteroaryl or heterocyclyl group being in the form of its corresponding N-oxide, in particular the pyridyl nitrogen in the compound of formula I may form the N-oxide, thereby providing a compound of the formula:

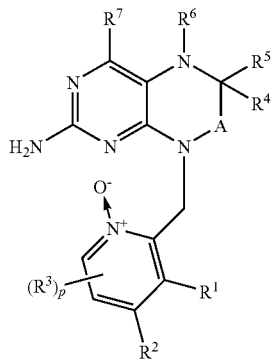

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, the compounds of this invention may possess an asymmetric center at the group A when A represents $CR^{10}R^{11}$ and $R^{10}$ represents H and $R^{11}$ represents a group other than H as defined hereinbefore. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess HSP90 inhibitory activity. The present invention also encompasses all tautomeric forms of the compounds of formula I that possess HSP90 inhibitory activity.

It is also to be understood that certain compounds of the formula I may exist in solvated as well as unsolvated forms such as, for example, hydrated forms. It is to be understood that the invention encompasses all such solvated forms that possess HSP90 inhibitory activity.

It is also to be understood that certain compounds of the formula I may exhibit polymorphism, and that the invention encompasses all such forms that possess HSP90 inhibitory activity.

It is to be understood that certain compounds of formula I defined above may exhibit the phenomenon of tautomerism. In particular, tautomerism may affect heteroaryl rings or heterocyclic groups within the compounds of formula I that bear 1 or 2 oxo or thioxo substituents. For example when $R^4$ is H and $R^5$ is hydroxy the compound is likely to tautomerise to the more stable oxo form:

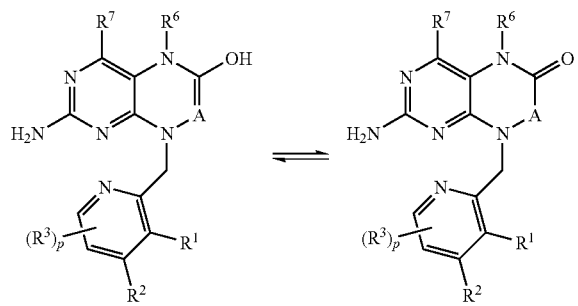

It is to be understood that the present invention includes in its definition any such tautomeric form, or a mixture thereof, which possesses the above-mentioned activity and is not to be limited merely to any one tautomeric form utilised within the formulae drawings or named in the Examples. For example, where the compound of formula I carries a pyrazolyl group, a tautomeric mixture of compounds comprising a 1H-pyrazol-3-yl group and a 1H-pyrazol-5-yl group may be present. In general, just one of any such tautomeric forms is named in the Examples that follow hereinafter or is presented in any relevant formulae drawings that follow hereinafter.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable counter ion" means an ion having a charge opposite to that of the substance with which it is associated and that is pharmaceutically acceptable. Representative examples include, but are not limited to, chloride, bromide, iodide, methanesulfonate, p-tolylsulfonate, trifluoroacetate, acetate, and the like.

A "pharmaceutically acceptable salt" of a compound means a salt that is pharmaceutically acceptable and that possesses the desired pharmacological activity of the parent compound. Such pharmaceutically-acceptable salts of a compound of the formula I is, for example, an acid-addition salt of a compound of the formula I, for example an acid-addition salt with an inorganic or organic acid such as hydrochloric, hydrobromic, sulfuric, trifluoroacetic, citric or maleic acid; or, for example, a salt of a compound of the formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. Compounds of the invention may form internal salts or zwitterions, for example between a carboxy group and a sufficiently basic group in the compound of formula I.

"Leaving group" has the meaning conventionally associated with it in synthetic organic chemistry i.e., an atom or group capable of being displaced by a nucleophile and includes halogen (such as chloro, bromo, iodo), alkanesulfonyloxy (such as mesyloxy or trifluorosulfonyloxy) or arenesulfonyloxy (such as tosyloxy), and the like. Leaving Groups are well known in the art and are catalogued in "Protective Groups in Organic Synthesis 3$^{rd}$ Ed.", edited by Theodora Green and Peter Wuts (John Wiley, 1999).

It is further to be understood that a suitable pharmaceutically-acceptable pro-drug of a compound of the formula I also forms an aspect of the present invention. Accordingly, the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically-acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the formula I that possesses a carboxy group is, for example, an in vivo cleavable ester thereof. An in vivo cleavable ester of a compound of the formula I containing a carboxy group is, for example, a pharmaceutically-acceptable ester which is cleaved in the human or animal body to produce the parent acid. Suitable pharmaceutically-acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically-acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically-acceptable pro-drug of a compound of the formula I that possesses an amino group is, for example, an in vivo cleavable amide derivative thereof. Suitable pharmaceutically-acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

"Treating" or "treatment" of a disease includes:
1. preventing the disease, i.e. causing the clinical symptoms of the disease not to develop in a mammal that may be exposed to or predisposed to the disease but does not yet experience or display symptoms of the disease;
2. inhibiting the disease, i.e., arresting or reducing the development of the disease or its clinical symptoms; or
3. relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The phrase "compound of the invention" means those compounds which are disclosed herein, both generically and specifically.

Particular novel compounds of the invention include, for example, compounds of the formula I, or pharmaceutically acceptable salts and pro-drugs thereof, wherein, unless otherwise stated, each of $R^1$, $R^2$, $R^3$, $R^4$, $R^5$, $R^6$, $R^7$, p and A has any of the meanings defined hereinbefore or in any of paragraphs (1) to (87) hereinafter:—

(1) $R^1$, $R^2$ and $R^3$ are independently selected from H, halo or a group of the formula:

—$X^1$—$R^8$, wherein $X^1$ is a direct bond, O, S or $NR^{8a}$, wherein $R^{8a}$ is H or $C_{1-4}$alkyl, and $R^8$ is selected from H, $C_{1-4}$alkyl, $C_{2-4}$alkenyl, $C_{3-6}$cycloalkyl and $C_{2-4}$alkynyl, and wherein $R^1$, $R^2$ and $R^3$ may independently of each other be optionally substituted on carbon by one or more substituents selected from halo, hydroxy, amino, N—($C_{1-4}$alkyl)amino, N,N—($C_{1-4}$alkyl)$_2$amino, $C_{1-4}$alkoxy, $C_{3-6}$cycloalkyl, carbamoyl, N—($C_{1-4}$alkyl)carbamoyl and N,N—($C_{1-4}$alkyl)$_2$carbamoyl.

(2) $R^1$, $R^2$ and $R^3$ are independently selected from H, halo or a group of the formula:

—$X^1$—$R^8$, wherein $X^1$ is a direct bond, O, S or $NR^{8a}$, wherein $R^{8a}$ is H or $C_{1-4}$alkyl, and $R^8$ is selected from H, $C_{1-4}$alkyl, $C_{2-4}$alkenyl, $C_{3-6}$cycloalkyl and $C_{2-4}$alkynyl, and wherein $R^1$, $R^2$ and $R^3$ may independently of each other be optionally substituted on carbon by one or more substituents selected from hydroxy, $C_{1-4}$alkoxy and $C_{3-6}$cycloalkyl.

(3) $R^1$, $R^2$ and $R^3$ are independently selected from halo or a group of the formula:

—$X^1$—$R^8$, wherein $X^1$ is a direct bond, O or S, and $R^8$ is selected from H and $C_{1-4}$alkyl.

(4) $R^1$, $R^2$ and $R^3$ are independently selected from H, chloro, bromo, iodo, amino or a group of the formula:

—$X^1$—$R^8$, wherein $X^1$ is a direct bond, O or S, and $R^8$ is selected from H, $C_{1-4}$alkyl, $C_{2-4}$alkenyl and $C_{3-6}$cycloalkyl, and wherein $R^1$, $R^2$ and $R^3$ may independently of each other be optionally substituted on carbon by one or more substituents selected from hydroxy, $C_{1-3}$alkoxy $C_{3-6}$cycloalkyl.

(5) $R^1$, $R^2$ and $R^3$ are each a group of the formula:

—$X^1$—$R^8$, wherein $X^1$ is a direct bond or O, and $R^8$ is $C_{1-4}$alkyl (particularly $C_{1-2}$alkyl, for example methyl), and wherein $R^1$, $R^2$ and $R^3$ may independently of each other be optionally substituted on carbon by one or more substituents selected from hydroxy, $C_{1-3}$alkoxy $C_{3-6}$cycloalkyl.

(6) $R^1$, $R^2$ and $R^3$ are each a group of the formula:

—$X^1$—$R^8$, wherein $X^1$ is a direct bond or O, and $R^8$ is $C_{1-4}$alkyl (particularly $C_{1-2}$alkyl, for example methyl).

(7) $R^1$, $R^2$ and $R^3$ are independently selected from H, chloro, bromo, iodo, amino, methyl, ethyl, methoxy, ethoxy, isopropyloxy, isobutyloxy, allyloxy, methylthio, ethylthio, hydroxymethyl, 2-hydroxyethyl, 2-methoxyethoxy, 2-hydroxyethoxy and cyclopropylmethoxy.

(8) $R^1$, $R^2$ and $R^3$ are independently selected from methyl and methoxy.

(9) $R^1$ is selected from H, halo, $C_{1-4}$alkyl and $C_{1-4}$alkoxy.

(10) $R^1$ is selected from H, halo and $C_{1-3}$alkyl.

(11) $R^1$ is selected from halo and $C_{1-3}$alkyl.

(12) $R^1$ is selected from chloro, bromo, methyl and methoxy.

(13) $R^1$ is selected from chloro, bromo and methyl.

(14) $R^1$ is $C_{1-3}$alkyl.

(15) $R^1$ is methyl.

(16) $R^2$ is selected from H, halo, hydroxy, amino, $C_{1-4}$alkyl, $C_{1-4}$alkoxy, $C_{1-4}$alkylthio, N—($C_{1-4}$alkyl)amino, N,N—($C_{1-4}$alkyl)$_2$amino, wherein $R^2$ may be optionally substituted on carbon by one or more substituents selected from hydroxy and $C_{1-4}$alkoxy.

(17) $R^2$ is selected from halo, hydroxy, $C_{1-3}$alkyl, $C_{1-3}$alkoxy, $C_{1-3}$alkylthio, wherein $R^2$ may be optionally substituted on carbon by one or more substituents selected from hydroxy and $C_{1-3}$alkoxy.

(18) $R^2$ is selected from chloro, bromo, iodo, hydroxy, methoxy, methyl and methylthio.

(19) $R^2$ is selected from chloro, bromo, iodo, methoxy, methyl and methylthio.

(20) $R^2$ is $C_{1-3}$alkoxy.

(21) $R^2$ is selected from halo, $C_{1-3}$alkoxy and $C_{1-3}$alkylthio (particularly bromo, methoxy and methylthio).

(22) $R^2$ is methoxy.

(23) p is 1 or 2 (particularly 1) and $R^3$ is selected from H, halo, hydroxy, $C_{1-4}$alkyl, $C_{1-4}$alkoxy and $C_{1-4}$alkylthio, wherein $R^3$ may be optionally substituted on carbon by one or more substituents selected from hydroxy and $C_{1-3}$alkoxy.

(24) p is 1 and $R^3$ is selected from chloro, bromo, iodo, hydroxy, methoxy, methyl and methylthio.

(25) p is 1 and $R^3$ is $C_{1-3}$alkyl (particularly methyl).

(26) p is 1, $R^3$ is $C_{1-3}$alkyl and $R^3$ is in the meta-position to the pyridyl nitrogen.

(27) p is 1, $R^3$ is methyl and $R^3$ is in the meta-position to the pyridyl nitrogen.

(28) at least 1 of $R^1$, $R^2$ and $R^3$ is not H.

(29) $R^1$ is selected from H, halo and $C_{1-3}$alkyl (particularly $R^1$ is halo or $C_{1-3}$alkyl);

$R^2$ is selected from halo, hydroxy, $C_{1-3}$alkyl, $C_{1-3}$alkoxy, $C_{1-3}$alkylthio, wherein $R^2$ may be optionally substituted on carbon by one or more substituents selected from hydroxy and $C_{1-3}$alkoxy; and p is 1, $R^3$ is in the meta-position to the pyridyl nitrogen, and $R^3$ is selected from H, halo, hydroxy, $C_{1-4}$alkyl, $C_{1-4}$alkoxy and $C_{1-4}$alkylthio, wherein $R^3$ may be optionally substituted on carbon by one or more substituents selected from hydroxy and $C_{1-3}$alkoxy (particularly $R^3$ is selected from chloro, bromo, $C_{1-3}$alkyl and $C_{1-3}$alkoxy).

(30) $R^1$ is selected from H, halo and $C_{1-3}$alkyl (particularly $R^1$ is halo or $C_{1-3}$alkyl);

$R^2$ is selected from halo, $C_{1-3}$alkyl, $C_{1-3}$alkoxy and $C_{1-3}$alkylthio (particularly $R^2$ is halo, $C_{1-3}$alkoxy or $C_{1-3}$alkylthio, more particularly bromo, methoxy or methylthio), wherein $R^2$ is optionally substituted on carbon by one or more substituents selected from hydroxy and $C_{1-3}$alkoxy; and p is 1, $R^3$ is in the meta-position to the pyridyl nitrogen, and $R^3$ is selected from H, halo, hydroxy, $C_{1-4}$alkyl, $C_{1-4}$alkoxy and $C_{1-4}$alkylthio, wherein $R^3$ is optionally substituted on carbon by one or more substituents selected from hydroxy and $C_{1-3}$alkoxy (particularly $R^3$ is selected from chloro, bromo, $C_{1-3}$alkyl and $C_{1-3}$alkoxy).

(31) $R^1$ is $C_{1-3}$alkyl (particularly methyl);

$R^2$ is $C_{1-3}$alkoxy (particularly methoxy); and p is 1, $R^3$ is in the meta-position to the pyridyl nitrogen, and $R^3$ is $C_{1-3}$alkyl (particularly methyl).

(32) The pyridyl group in formula I is in the form of the N-oxide of the formula:

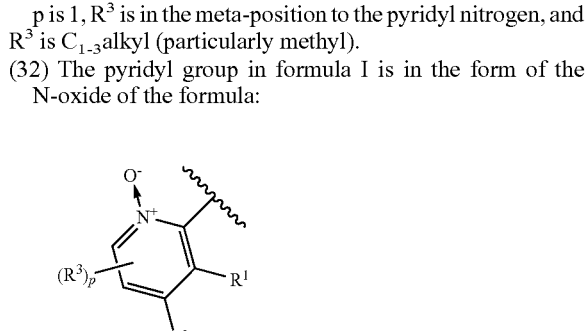

wherein $R^1$, $R^2$, $R^3$ and p have any of the values defined herein, particularly those defined in (1) to (31) above.

(33) The pyridyl group in formula I is of the formula:

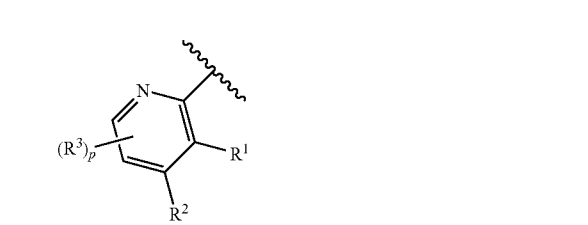

is selected from 4-methoxy-3,5-dimethylpyridin-2-yl, 4-chloro-3,5-dimethylpyridin-2-yl, 4-chloro-3,5-dimethyl-1-oxypyridin-2-yl, 4-methoxy-3,5-dimethyl-1-oxypyridin- 2-yl, 4-bromo-3,5-dimethylpyridin-2-yl, 4-bromo-3,5-dimethyl-1-oxy-pyridin-2-yl, 4-iodo-3,5-dimethyl-1-oxy-pyridin-2-yl, 4-iodo-3,5-dimethylpyridin-2-yl, 3-bromo-4,5,6-trimethoxypyridin-2-yl, 3-chloro-4,5,6-trimethoxypyridin-2-yl, 3,4,5-trimethylpyridin-2-yl, 3,4,5-trimethyl-1-oxypyridin-2-yl, 3,4,5-trimethoxypyridin-2-yl, 6-chloro-4-methoxy-3,5-dimethylpyridin-2-yl, 6-bromo-4-methoxy-3,5-dimethylpyridin-2-yl, 6-chloro-4-methoxy-3,5-dimethyl-1-oxy-pyridin-2-yl, 6-bromo-4-methoxy-3,5-dimethyl-1-oxy-pyridin-2-yl, 6,4-dimethoxy-3,5-dimethylpyridin-2-yl, 6,4-dimethoxy-3,5-dimethyl-1-oxy-pyridin-2-yl, 3-bromo-4,5,6-trimethoxy-1-oxy-pyridin-2-yl and 3-chloro-4,5,6-trimethoxy-1-oxy-pyridin-2-yl.

(34) The pyridyl group in formula I is of the formula:

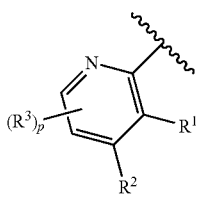

is selected from 4-methoxy-3,5-dimethylpyridin-2-yl, 4-chloro-3,5-dimethylpyridin-2-yl, 4-chloro-3,5-dimethyl-1-oxypyridin-2-yl, 4-methoxy-3,5-dimethyl-1-oxypyridin-2-yl, 4-bromo-3,5-dimethylpyridin-2-yl, 4-methylthio-3,5-dimethylpyridin-2-yl, 4-bromo-3,5-dimethyl-1-oxy-pyridin-2-yl, 4-methylthio-3,5-dimethyl-1-oxy-pyridin-2-yl, 4-iodo-3,5-dimethyl-1-oxy-pyridin-2-yl, 4-iodo-3,5-dimethylpyridin-2-yl, 3-bromo-4,5,6-trimethoxypyridin-2-yl, 3-chloro-4,5,6-trimethoxypyridin-2-yl, 3,4,5-trimethylpyridin-2-yl, 3,4,5-trimethyl-1-oxypyridin-2-yl, 3,4,5-trimethoxypyridin-2-yl, 6-chloro-4-methoxy-3,5-dimethylpyridin-2-yl, 6-bromo-4-methoxy-3,5-dimethylpyridin-2-yl, 6-chloro-4-methoxy-3,5-dimethyl-1-oxy-pyridin-2-yl, 6-bromo-4-methoxy-3,5-dimethyl-1-oxy-pyridin-2-yl, 6,4-dimethoxy-3,5-dimethylpyridin-2-yl, 6,4-dimethoxy-3,5-dimethyl-1-oxy-pyridin-2-yl, 3-bromo-4,5,6-trimethoxy-1-oxy-pyridin-2-yl and 3-chloro-4,5,6-trimethoxy-1-oxy-pyridin-2-yl.

(35) The pyridyl group in formula I of the formula:

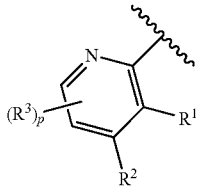

is selected from 4-methoxy-3,5-dimethylpyridin-2-yl, 4-chloro-3,5-dimethylpyridin-2-yl, 4-chloro-3,5-dimethyl-1-oxypyridin-2-yl, 4-methoxy-3,5-dimethyl-1-oxypyridin-2-yl, 4-bromo-3,5-dimethylpyridin-2-yl, 4-bromo-3,5-dimethyl-1-oxy-pyridin-2-yl, 4-iodo-3,5-dimethyl-1-oxy-pyridin-2-yl, 4-iodo-3,5-dimethylpyridin-2-yl and 3-bromo-4,5,6-trimethoxypyridin-2-yl.

(36) The pyridyl group in formula I of the formula:

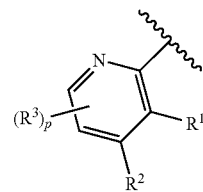

is selected from 4-methoxy-3,5-dimethylpyridin-2-yl, 4-chloro-3,5-dimethylpyridin-2-yl, 4-chloro-3,5-dimethyl-1-oxypyridin-2-yl, 4-methoxy-3,5-dimethyl-1-oxypyridin-2-yl, 4-bromo-3,5-dimethylpyridin-2-yl, 4-methylthio-3,5-dimethylpyridin-2-yl, 4-bromo-3,5-dimethyl-1-oxy-pyridin-2-yl, 4-methylthio-3,5-dimethyl-1-oxy-pyridin-2-yl, 4-iodo-3,5-dimethyl-1-oxy-pyridin-2-yl, 4-iodo-3,5-dimethylpyridin-2-yl, 3-bromo-4,5,6-trimethoxypyridin-2-yl, 6-chloro-4-methoxy-3,5-dimethylpyridin-2-yl and 6-bromo-4-methoxy-3,5-dimethylpyridin-2-yl.

(37) the group of the formula:

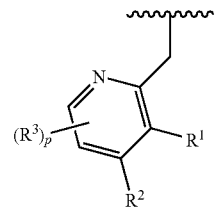

in formula I is of the formula:

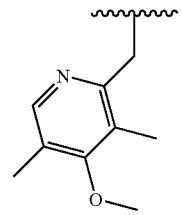

wherein ⁓ indicates the point of attachment to the nitrogen in formula I.

(38) A is $CR^{10}R^{11}$, wherein $R^{10}$ and $R^{11}$ are as hereinbefore defined.

(39) A is $CR^{10}R^{11}$, wherein $R^{10}$ is H or $C_{1-4}$alkyl, and $R^{11}$ is as hereinbefore defined.

(40) A is $CR^{10}R^{11}$, wherein $R^{10}$ is H and $R^{11}$ is H, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, $C_{1-6}$alkylsulfonylaminocarbonyl, $C_{3-7}$cycloalkyl-$X^2$—, aryl-$X^2$, $C_{3-7}$cycloalkenyl-$X^2$—, heterocyclyl-$X^3$— or heteroaryl-$X^4$—, wherein $X^2$, $X^3$ and $X^4$ are selected from a direct bond, —C(O)— and —N($R^{22}$)C(O)—; wherein $R^{22}$ is hydrogen or $C_{1-4}$alkyl, wherein $R^{11}$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 or 2 oxo or thioxo substituents, and wherein any aryl or heteroaryl group within $R^{11}$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^8$—, aryl-$X^8$—, heterocyclyl-$X^9$— or heteroaryl-$X^{10}$—, wherein $X^8$, $X^9$ and $X^{10}$ are independently selected from a direct bond, —O—, —N($R^{21}$)—, —C(O)—, —N($R^{22}$)C(O)—, —C(O)N($R^{23}$)—, S(O)$_q$—, —SO$_2$N($R^{24}$)— or —N($R^{25}$)SO$_2$—, wherein $R^{21}$, $R^{22}$, $R^{23}$, $R^{24}$ and $R^{25}$ are independently selected from hydrogen or $C_{1-4}$alkyl and q is 0-2, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{13}$ may optionally bear 1 or 2 oxo or thioxo substituents, and wherein any aryl or heteroaryl group within $R^{13}$ may optionally bear a $C_{1-3}$alkylenedioxy group;

$R^{14}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$ and $R^{19}$ may be optionally substituted on carbon by one or more $R^{20}$;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $R^{20}$ is selected from halo, amino, methyl, ethyl, methoxy, ethoxy, methylamino, ethylamino, dimethylamino, diethylamino and N-methyl-N-ethylamino;

or $R^{10}$ and $R^{11}$ together form oxo (=O).

(41) A is $CR^{10}R^{11}$, wherein $R^{10}$ is H and $R^{11}$ is H, carbamoyl, sulfamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, N—($C_{1-6}$alkyl)sulfamoyl, N,N—($C_{1-6}$alkyl)$_2$sulfamoyl, $C_{3-7}$cycloalkyl-$X^2$—, phenyl-$X^2$, heterocyclyl-$X^3$— or heteroaryl-$X^4$—, wherein said heteroaryl is a monocyclic 5 or 6-membered heteroaryl ring containing 1, 2 or 3 heteroatoms (suitably 1 or 2 heteroatoms) selected from O, S and N, and said heterocyclyl is a monocyclic 5, 6 or 7-membered heterocyclyl ring containing 1, 2 or 3 (suitably 1 or 2 heteroatoms) heteroatoms selected from O, S and N, wherein $R^{11}$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 oxo substituent, and wherein any phenyl or heteroaryl group within $R^{11}$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl, phenyl-, a monocyclic 5 or 6-membered heteroaryl ring containing 1, 2 or 3 heteroatoms selected from O, S and N, and a monocyclic 5, 6 or 7-membered heterocyclyl ring containing 1, 2 or 3 (suitably 1 or 2) heteroatoms selected from O, S and N, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{13}$ may optionally bear 1 oxo substituent, and wherein any aryl or heteroaryl group within $R^{13}$ may optionally bear a $C_{1-3}$alkylenedioxy group;

$R^{14}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$, $X^3$ and $X^4$ are independently selected from a direct bond, —C(O)— and —N($R^{22}$)C(O)— wherein $R^{22}$ is selected from hydrogen or $C_{1-4}$alkyl;

or $R^{10}$ and $R^{11}$ together form oxo (=O).

(42) A is $CR^{10}R^{11}$, wherein $R^{10}$ is H and $R^{11}$ is H, $C_{1-6}$alkyl, $C_{3-7}$cycloalkyl-$X^2$—, phenyl-$X^2$, heterocyclyl-$X^3$— or heteroaryl-$X^4$—, wherein said heteroaryl is a monocyclic 5 or 6 membered heteroaryl ring containing 1, 2 or 3 heteroatoms selected from O, S and N, and said heterocyclyl is a monocyclic 5, 6 or 7-membered heterocyclyl ring containing 1, 2 or 3 (suitably 1 or 2) heteroatoms selected from O, S and N, wherein $R^{11}$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 oxo substituent, and wherein any phenyl or heteroaryl group within $R^{11}$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl, phenyl-, a monocyclic 5 or 6-membered heteroaryl ring containing 1, 2 or 3 heteroatoms selected from O, S and N, and a monocyclic 5, 6 or 7-membered heterocyclyl ring containing 1, 2 or 3 (suitably 1 or 2) heteroatoms selected from O, S and N, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{13}$ may optionally bear 1 oxo substituent;

$R^{14}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$, $X^3$ and $X^4$ are independently selected from a direct bond, —C(O)— and —N($R^{22}$)C(O)—, wherein $R^{22}$ is selected from hydrogen or $C_{1-4}$alkyl;

or $R^{10}$ and $R^{11}$ together form oxo (═O).

(43) A is $CR^{10}R^{11}$, wherein $R^{10}$ is H and $R^{11}$ is H, $C_{1-6}$alkyl, $C_{3-7}$cycloalkyl-$X^2$—, phenyl-$X^2$, heterocyclyl-$X^3$— or heteroaryl-$X^4$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl, wherein said $C_{3-7}$cycloalkyl is selected from cyclopropyl, cyclobutyl, cyclopentyl and cyclohexyl, and wherein $R^{11}$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 oxo substituent;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, cyclopropyl, cyclobutyl, cyclopentyl, cyclohexyl, phenyl, a heteroaryl selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and a heterocyclyl selected from azetidinyl, pyrrolidinyl, morpholinyl, piperidinyl and piperazinyl, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$;

and wherein any heterocyclyl group within $R^{13}$ may optionally bear 1 oxo substituent;

$R^{14}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$, $X^3$ and $X^4$ are independently selected from a direct bond, —C(O)— and —N($R^{22}$)C(O)—, wherein $R^{22}$ is selected from hydrogen or $C_{1-4}$alkyl.

(43a) A is $CR^{10}R^{11}$, wherein $R^{10}$ is H and $R^{11}$ is selected from H and $C_{1-4}$alkyl, wherein $R^{11}$ is optionally substituted on carbon by one or more $R^{13}$ selected from halo, nitro, cyano, hydroxy, trifluoromethoxy, amino, carboxy, carboxyamino, carbamoyl, mercapto, sulfamoyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{1-4}$alkylsulfonylamino, phenyl, pyridyl and pyrimidinyl. For example, $R^{11}$ is selected from H and $C_{1-4}$alkyl.

(44) A is $CR^{10}R^{11}$, wherein $R^{10}$ is H and $R^{11}$ is H, $C_{1-6}$alkyl or $C_{3-7}$cycloalkyl-$X^2$—, wherein $R^{11}$ may be optionally substituted on carbon by one or more $R^{13}$;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl, phenyl-, a monocyclic 5 or 6-membered heteroaryl ring containing 1, 2 or 3 heteroatoms selected from O, S and N, and a monocyclic 5, 6 or 7-membered heterocyclyl ring containing 1, 2 or 3 (suitably 1 or 2) heteroatoms selected from O, S and N, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$;

and wherein any heterocyclyl group within $R^{13}$ may optionally bear 1 oxo substituent;

$R^{19}$ is selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$ is selected from a direct bond, —C(O)—, —N($R^{22}$)C(O)—; wherein $R^{22}$ is hydrogen or $C_{1-4}$alkyl.

(45) A is $CR^{10}R^{11}$ wherein $R^{10}$ is H and $R^{11}$ is H or $C_{1-6}$alkyl, wherein $R^{11}$ may be optionally substituted on carbon by one or more $R^{13}$;

$R^{13}$ is selected from fluoro, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O), wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl, phenyl-, a monocyclic 5 or 6-membered heteroaryl ring containing 1, 2 or 3 heteroatoms selected from O, S and N, and a monocyclic 5, 6 or 7-membered heterocyclyl ring containing 1, 2 or 3 (suitably 1 or 2) heteroatoms selected from O, S and N, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$;

and wherein any heterocyclyl group within $R^{13}$ may optionally bear 1 oxo substituent;

$R^{19}$ is selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl; and $R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino.

(46) A is $CR^{10}R^{11}$, wherein $R^{10}$ is H and $R^{11}$ is H or $C_{1-6}$alkyl, wherein $R^{11}$ may be optionally substituted on carbon by one or more $R^{13}$;

$R^{13}$ is selected from fluoro, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl and phenyl, and wherein $R^{13}$ may be optionally substituted on carbon by one or more $R^{18}$; and $R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino.

(47) A is $CR^{10}R^{11}$, wherein $R^{10}$ is H and $R^{11}$ is H or $C_{1-6}$alkyl, wherein $R^{11}$ may be optionally substituted on carbon by one or more $R^{13}$;

$R^{13}$ is selected from carboxy, carbamoyl, N—($C_{1-4}$alkyl)carbamoyl, N,N—($C_{1-4}$alkyl)$_2$carbamoyl, $C_{1-4}$alkoxycarbonyl and phenyl, and wherein $R^{13}$ may be optionally substituted on carbon by one or more $R^{18}$; and $R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino.

(48) A is $CR^{10}R^{11}$, wherein $R^{10}$ is H and $R^{11}$ is H or $C_{1-6}$alkyl, wherein $R^{11}$ may be optionally substituted on carbon by one or more $R^{13}$;

$R^{13}$ is selected from carboxy, carbamoyl, N—($C_{1-4}$alkyl)carbamoyl, $C_{1-4}$alkoxycarbonyl and phenyl-, and wherein $R^{13}$ may be optionally substituted on carbon by one or more $R^{18}$; and $R^{18}$ is N,N—($C_{1-4}$alkyl)$_2$amino.

(49) A is $CR^{10}R^{11}$, wherein $R^{10}$ is H and $R^{11}$ is selected from H, methyl, propyl, 2-methylpropyl, benzyl, methoxycarbonylmethyl, carboxymethyl, carbamoylmethyl, N-[3-(dimethylamino)propyl]carbamoylmethyl and N-[2-(dimethylamino)ethyl]carbamoylmethyl.

(50) A is $CR^{10}R^{11}$, wherein $R^{10}$ is H and $R^{11}$ is H or $C_{1-4}$alkyl, for example $R^{11}$ is H, methyl, ethyl or isopropyl.

(51) A is $NR^9$, wherein $R^9$ is as hereinbefore defined.

(52) A is $NR^9$, wherein $R^9$ is selected from H, $C_{1-6}$alkyl, $C_{3-7}$cycloalkyl, $C_{3-7}$cycloalkyl-$C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^9$ may be optionally substituted on carbon by one or more $R^{16}$; and $R^{16}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino.

(53) A is $NR^9$, wherein $R^9$ is selected from H, $C_{1-4}$alkyl, $C_{3-7}$cycloalkyl, $C_{3-7}$cycloalkyl-$C_{4}$alkyl, for example $R^9$ is selected from H, methyl, ethyl, cyclopropyl, cyclobutyl, cyclopentyl, cyclohexyl, cyclopropyl-$C_{1-4}$alkyl, cyclobutyl-$C_{1-4}$alkyl, cyclopentyl-$C_{1-4}$alkyl and cyclohexyl-$C_{1-4}$alkyl. More particularly $R^9$ is selected from H, methyl and ethyl.

(54) $R^4$ is H and $R^5$ is as hereinbefore defined, or $R^4$ and $R^5$ together form oxo (═O).

(55) $R^4$ is H and $R^5$ is H, carboxy, carbamoyl, sulfamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylaminocarbonyl, $C_{3-7}$cycloalkyl-$X^2$—, aryl-$X^2$, $C_{3-7}$cycloalkenyl-$X^2$— or heterocyclyl-$X^3$— or heteroaryl-$X^4$—, wherein $R^5$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^5$ may optionally bear 1 or 2 oxo or thioxo substituents, and wherein any aryl or heteroaryl group within $R^5$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^8$—, aryl-$X^8$—, heterocyclyl-$X^9$— or heteroaryl-$X^{10}$—, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{13}$ may optionally bear 1 or 2 oxo or thioxo substituents, and wherein any aryl or heteroaryl group within $R^{13}$ may optionally bear a $C_{1-3}$alkylenedioxy group;

$R^{14}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$ and $R^{19}$ may be optionally substituted on carbon by one or more $R^{20}$;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino;

$R^{20}$ is selected from halo, amino, methyl, ethyl, methoxy, ethoxy, methylamino, ethylamino, dimethylamino, diethylamino and N-methyl-N-ethylamino;

$X^2$, $X^3$ and $X^4$ are independently selected from a direct bond, —C(O)—, —N($R^{22}$)C(O)—; wherein $R^{22}$ is hydrogen or $C_{1-4}$alkyl; and $X^8$, $X^9$ and $X^{10}$ are independently selected from a direct bond, —O—, —N($R^{21}$)—, —C(O)—, —N($R^{22}$)C(O)—, —C(O)N($R^{23}$)—, S(O)$_q$—, —SO$_2$N($R^{24}$)— or —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

or $R^4$ and $R^5$ together form oxo (═O).

(56) $R^4$ is H and $R^5$ is H, carbamoyl, sulfamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, N—($C_{1-6}$alkyl)sulfamoyl, N,N—($C_{1-6}$alkyl)$_2$sulfamoyl, $C_{3-7}$cycloalkyl-$X^2$—, phenyl-$X^2$, heterocyclyl-$X^3$— or heteroaryl-$X^4$—, wherein said heteroaryl is a monocyclic 5 or 6-membered heteroaryl ring containing 1, 2 or 3 heteroatoms selected from O, S and N, and said heterocyclyl is a monocyclic 5, 6 or 7-membered heterocyclyl ring containing 1, 2 or 3 (suitably 1 or 2) heteroatoms selected from O, S and N, wherein $R^5$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^5$ may optionally bear 1 oxo substituent, and wherein any phenyl or heteroaryl group within $R^5$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl, phenyl-, a monocyclic 5 or 6-membered heteroaryl ring containing 1, 2 or 3 heteroatoms selected from O, S and N, and a monocyclic 5, 6 or 7-membered heterocyclyl ring containing 1, 2 or 3 (suitably 1 or 2) heteroatoms selected from O, S and N, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{13}$ may optionally bear 1 oxo substituent;

$R^{14}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$, $X^3$ and $X^4$ are independently selected from a direct bond, —C(O)— and —N($R^{22}$)C(O)—; wherein $R^{22}$ is hydrogen or $C_{1-4}$alkyl;

or $R^4$ and $R^5$ together form oxo (=O).

(57) $R^4$ is H and $R^5$ is H, $C_{1-6}$alkyl, $C_{3-7}$cycloalkyl-$X^2$—, phenyl-$X^2$, heterocyclyl-$X^3$— or heteroaryl-$X^4$—, wherein said heteroaryl is a monocyclic 5 or 6-membered heteroaryl ring containing 1, 2 or 3 heteroatoms selected from O, S and N, and said heterocyclyl is a monocyclic 5, 6 or 7-membered heterocyclyl ring containing 1, 2 or 3 (suitably 1 or 2) heteroatoms selected from O, S and N, wherein $R^5$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^4$ may optionally bear 1 oxo substituent, and wherein any phenyl or heteroaryl group within $R^4$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl, phenyl-, a monocyclic 5 or 6-membered heteroaryl ring containing 1, 2 or 3 heteroatoms selected from O, S and N, and a monocyclic 5, 6 or 7-membered heterocyclyl ring containing 1, 2 or 3 (suitably 1 or 2) heteroatoms selected from O, S and N, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{13}$ may optionally bear 1 oxo substituent;

$R^{14}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$, $X^3$ and $X^4$ are independently selected from a direct bond, —C(O)— and —N($R^{22}$)C(O)—; wherein $R^{22}$ is hydrogen or $C_{1-4}$alkyl;

or $R^4$ and $R^5$ together form oxo (=O).

(58) $R^4$ is H and $R^5$ is H, $C_{1-6}$alkyl, $C_{3-7}$cycloalkyl-$X^2$—, phenyl-$X^2$, heterocyclyl-$X^3$— or heteroaryl-$X^4$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl, wherein said $C_{3-7}$cycloalkyl is selected from cyclopropyl, cyclobutyl, cyclopentyl and cyclohexyl, and wherein $R^5$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^5$ may optionally bear 1 oxo substituent, and wherein any phenyl or heteroaryl group within $R^5$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O), wherein a is 0 to 2, $C_{1-4}$alkoxycarbonyl, N—($C_{1-4}$alkyl)sulfamoyl, N,N—($C_{1-4}$alkyl)$_2$sulfamoyl, cyclopropyl, cyclobutyl, cyclopentyl, cyclohexyl, phenyl, a heteroaryl selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and a heterocyclyl selected from azetidinyl, pyrrolidinyl, morpholinyl, piperidinyl and piperazinyl, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$;

and wherein any heterocyclyl group within $R^{13}$ may optionally bear 1 oxo substituent;

$R^{14}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$, $X^3$ and $X^4$ are independently selected from a direct bond, —C(O)— and —N($R^{22}$)C(O)—; wherein $R^{22}$ is hydrogen or $C_{1-4}$alkyl;

or $R^4$ and $R^5$ together form oxo (═O).

(59) $R^4$ is H and $R^5$ is H, $C_{1-6}$alkyl or $C_{3-7}$cycloalkyl-$X^2$—, wherein $R^5$ may be optionally substituted on carbon by one or more $R^{13}$;

$R^{13}$ is selected from halo (such as fluoro), nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl, phenyl-, a monocyclic 5 or 6-membered heteroaryl ring containing 1, 2 or 3 heteroatoms selected from O, S and N, and a monocyclic 5, 6 or 7-membered heterocyclyl ring containing 1, 2 or 3 (suitably 1 or 2) heteroatoms selected from O, S and N, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{13}$ may optionally bear 1 oxo substituent;

$R^{19}$ is selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$ is selected from a direct bond, —C(O)— and —N($R^{22}$)C(O)—; wherein $R^{22}$ is hydrogen or $C_{1-4}$alkyl;

or $R^4$ and $R^5$ together form oxo (═O).

(60) $R^4$ is H and $R^5$ is H or $C_{1-4}$alkyl, or $R^4$ and $R^5$ together form oxo (═O).

For example $R^4$ is H and $R^5$ is H, methyl, ethyl or isopropyl. Alternatively, $R^4$ and $R^5$ together form oxo (═O).

(61) $R^4$ and $R^5$ are both H, or $R^4$ and $R^5$ together form oxo (═O).

(62) $R^6$ is selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, $C_{3-7}$cycloalkyl-$X^5$—, $C_{3-7}$cycloalkenyl-$X^5$—, aryl-$X^5$—, heterocyclyl-$X^6$— and heteroaryl-$X^7$—, wherein $X^5$, $X^6$ and $X^7$ are independently selected from a direct bond, —C(O)—, —N($R^{12}$)C(O)— and —SO$_2$—; wherein $R^{12}$ is selected from hydrogen or $C_{1-4}$alkyl, and wherein $R^6$ may be optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 or 2 oxo or thioxo substituents;

$R^{16}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^8$—, aryl-$X^8$—, heterocyclyl-$X^9$— or heteroaryl-$X^{10}$—, and wherein $R^{16}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{16}$ may optionally bear 1 or 2 oxo or thioxo substituents;

$R^{17}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{17}$ and $R^{19}$ may be optionally substituted on carbon by one or more $R^{20}$;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino;

$R^{20}$ is selected from halo, amino, methyl, ethyl, methoxy, ethoxy, methylamino, ethylamino, dimethylamino, diethylamino and N-methyl-N-ethylamino; and $X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— or —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2.

(63) $R^6$ is selected from H, $C_{1-6}$alkyl, $C_{2-6}$alkenyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, $C_{3-7}$cycloalkyl-$X^5$—, phenyl-$X^5$—, heterocyclyl-$X^6$— and heteroaryl-$X^7$—, wherein said heteroaryl is a monocyclic 5 or 6-membered heteroaryl ring containing 1, 2 or 3 heteroatoms selected from O, S and N, and said heterocyclyl is a monocyclic 5, 6 or 7-membered heterocyclyl ring containing 1, 2 or 3 (suitably 1 or 2) heteroatoms selected from O, S and N;

wherein $X^5$, $X^6$ and $X^7$ are independently selected from a direct bond, —C(O)—, —N($R^{12}$)C(O)— and —SO$_2$—; wherein $R^{12}$ is selected from hydrogen or $C_{1-4}$alkyl, and wherein $R^6$ may be optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 oxo substituent;

$R^{16}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^8$—, phenyl-$X^8$—, heterocyclyl-$X^9$—, wherein said heterocyclyl is a monocyclic 5 or 6-membered heterocyclyl ring containing 1, 2 or 3 (suitably 1 or 2) heteroatoms selected from O, S and N, heteroaryl-$X^{10}$—, wherein said heteroaryl is a monocyclic 5, 6 or 7-membered heteroaryl ring containing 1, 2 or 3 heteroatoms selected from O, S and N, and wherein $R^{16}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{16}$ may optionally bear 1 oxo substituent;

$R^{17}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$ amino; and $X^8$, $X^9$ and $X^{10}$ are independently selected from a direct bond, —O—, —N($R^{21}$)—, —C(O)—, and —S(O)$_q$—, wherein $R^{21}$ is selected from hydrogen or $C_{1-4}$alkyl and q is 0-2.

(64) $R^6$ is selected from H and $C_{1-6}$alkyl, and wherein $R^6$ may be optionally substituted on carbon by one or more $R^{16}$;

$R^{16}$ is selected from fluoro, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^8$—, phenyl-$X^8$—, heterocyclyl-$X^9$—, wherein said heterocyclyl is a monocyclic 5 or 6-membered heterocyclyl ring containing 1, 2 or 3 (suitably 1 or 2) heteroatoms selected from O, S and N, heteroaryl-$X^{10}$—, wherein said heteroaryl is a monocyclic 5, 6 or 7-membered heteroaryl ring containing 1, 2 or 3 heteroatoms selected from O, S and N, and wherein $R^{16}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{16}$ may optionally bear 1 oxo substituent;

$R^{19}$ is independently selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$ amino; and $X^8$, $X^9$ and $X^{10}$ are independently selected from a direct bond, —O—, —N($R^{21}$)—, —C(O)—, and —S(O)$_q$—, wherein $R^{21}$ is selected from hydrogen or $C_{1-4}$alkyl and q is 0-2.

(65) $R^6$ is selected from H and $C_{1-6}$alkyl, and wherein $R^6$ may be optionally substituted on carbon by one or more $R^{16}$;

$R^{16}$ is selected from fluoro, $C_{1-6}$alkoxy, N—($C_{1-6}$alkyl)amino, N,N—($C_{1-6}$alkyl)$_2$amino, $C_{3-7}$cycloalkyl-$X^8$—, phenyl-$X^8$—, heterocyclyl-$X^9$—, wherein said heterocyclyl is a monocyclic 5 or 6-membered heterocyclyl ring containing 1, 2 or 3 (suitably 1 or 2) heteroatoms selected from O, S and N, heteroaryl-$X^{10}$—, wherein said heteroaryl is a monocyclic 5, 6 or 7-membered heteroaryl ring containing 1, 2 or 3 heteroatoms selected from O, S and N, and wherein $R^{16}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{16}$ may optionally bear 1 oxo substituent;

$R^{19}$ is independently selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$ amino; and $X^8$, $X^9$ and $X^{10}$ are independently selected from a direct bond, —O—, —N($R^{21}$)—, —C(O)—, and —S(O)$_q$—, wherein $R^{21}$ is selected from hydrogen or $C_{1-4}$alkyl and q is 0-2.

(66) $R^6$ is selected from H and $C_{1-6}$alkyl, and wherein $R^6$ may be optionally substituted on carbon by one or more $R^{16}$;

$R^{16}$ is selected from fluoro, $C_{1-6}$alkoxy, N,N—($C_{1-6}$alkyl)$_2$ amino, $C_{3-7}$cycloalkyl-$X^8$—, phenyl-$X^8$—, heterocyclyl-$X^9$—, wherein said heterocyclyl is a monocyclic 5 or 6-membered heterocyclyl ring containing 1, 2 or 3 (suitably 1 or 2) heteroatoms selected from O, S and N, heteroaryl-$X^{10}$—, wherein said heteroaryl is a monocyclic 5, 6 or 7-membered heteroaryl ring containing 1, 2 or 3 heteroatoms selected from O, S and N, and wherein any heterocyclyl group within $R^{16}$ may optionally bear 1 oxo substituent; and $X^8$, $X^9$ and $X^{10}$ are each a direct bond.

(67) $R^6$ is selected from H, $C_{1-4}$alkyl, $C_{2-4}$alkenyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)$_2$carbamoyl, $C_{3-7}$cycloalkyl-$X^5$—, phenyl-$X^5$—, heterocyclyl-$X^6$— and heteroaryl-$X^7$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl, wherein said $C_{3-7}$cycloalkyl is selected from cyclopropyl, cyclobutyl, cyclopentyl and cyclohexyl, wherein $X^5$, $X^6$ and $X^7$ are independently selected from a direct bond, —C(O)— and —N($R^{12}$)C(O)—, wherein $R^{12}$ is selected from hydrogen or $C_{1-4}$alkyl, and wherein $R^6$ may be optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 oxo substituent;

$R^{16}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{1-4}$alkylsulfonylamino, cyclopropyl-$X^8$—, cyclobutyl-$X^8$—, cyclopentyl-$X^8$—, cyclohexyl-$X^8$—, phenyl-$X^8$—, heterocyclyl-$X^9$—, wherein said heterocyclyl is selected from azetidinyl, pyrrolidinyl, morpholinyl, piperidinyl and piperazinyl, and heteroaryl-$X^{10}$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and wherein $R^{16}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{16}$ may optionally bear 1 oxo substituent;

$R^{17}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^8$, $X^9$ and $X^{10}$ are independently selected from a direct bond, —O—, —N($R^{21}$)—, —C(O)—, and —S(O)$_q$—, wherein $R^{21}$ is selected from hydrogen or $C_{1-4}$alkyl and q is 0-2.

(67a) $R^6$ is selected from H, $C_{1-6}$alkyl, $C_{3-7}$cycloalkyl-$X^5$—, phenyl-$X^5$—, heterocyclyl-$X^6$— and heteroaryl-$X^7$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl, wherein $X^5$, $X^6$ and $X^7$ are independently selected from a direct bond, —C(O)— and —N($R^{12}$)C(O)—, wherein $R^{12}$ is selected from hydrogen or $C_{1-4}$alkyl, and wherein $R^6$ may be optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 oxo substituent;

$R^{16}$ is selected from halo, cyano, hydroxy, amino, mercapto, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, $C_{1-4}$alkylS(O)$_a$ wherein a is 0 to 2, $C_{1-4}$alkoxycarbonyl, cyclopropyl-$X^8$—, cyclobutyl-$X^8$—, cyclopentyl-$X^8$—, cyclohexyl-$X^8$—, phenyl-$X^8$—, heterocyclyl-$X^9$—, wherein said heterocyclyl is selected from azetidinyl, pyrrolidinyl, morpholinyl, piperidinyl and piperazinyl, and heteroaryl-$X^{10}$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and wherein $R^{16}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{16}$ may optionally bear 1 oxo substituent;

$R^{17}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^8$, $X^9$ and $X^{10}$ are independently selected from a direct bond, —O—, —N($R^{21}$)—, —C(O)—, and —S(O)$_q$—, wherein $R^{21}$ is selected from hydrogen or $C_{1-4}$alkyl and q is 0-2.

(68) $R^6$ is selected from H and $C_{1-6}$alkyl, and wherein $R^6$ may be optionally substituted on carbon by one or more $R^{16}$;

$R^{16}$ is selected from halo (particularly fluoro), $C_{1-4}$alkoxy, N,N—($C_{1-4}$alkyl)$_2$amino, cyclopropyl-$X^8$—, phenyl-$X^8$—, heterocyclyl-$X^9$—, wherein said heterocyclyl is selected from imidazolidinyl, azetidinyl, pyrrolidinyl, morpholinyl, piperidinyl and piperazinyl, and heteroaryl-$X^{10}$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and wherein any heterocyclyl group within $R^{16}$ may optionally bear 1 oxo substituent; and $X^8$, $X^9$ and $X^{10}$ are independently selected from a direct bond, —O—, —N($R^{21}$)—, —C(O)—, and —S(O)$_q$—, wherein $R^{21}$ is selected from hydrogen or $C_{1-4}$alkyl and q is 0-2 (particularly $X^8$, $X^9$ and $X^{10}$ are each a direct bond).

(69) $R^6$ is selected from H and $C_{1-6}$alkyl, and wherein $R^6$ may be optionally substituted on carbon by one or more $R^{16}$;

$R^{16}$ is selected from halo (particularly fluoro), $C_{1-4}$alkoxy, N,N—($C_{1-4}$alkyl)$_2$amino, cyclopropyl-$X^8$—, phenyl-$X^8$—, heterocyclyl-$X^9$—, wherein said heterocyclyl is selected from imidazolidinyl, pyrrolidinyl, morpholinyl and piperazinyl, and heteroaryl-$X^{10}$—, wherein said heteroaryl is pyridyl, and wherein any heterocyclyl group within $R^{16}$ may optionally bear 1 oxo substituent; and $X^8$, $X^9$ and $X^{10}$ are each a direct bond.

(70) $R^6$ is selected from H, $C_{1-4}$alkyl, cyclopropyl, cyclobutyl, cyclopentyl, cyclohexyl, cyclopropyl-$C_{1-4}$alkyl, cyclobutyl-$C_{1-4}$alkyl, cyclopentyl-$C_{1-4}$alkyl, cyclohexyl-$C_{1-4}$alkyl, azetidinyl-$C_{1-4}$alkyl, pyrrolidinyl-$C_{1-4}$alkyl, morpholinyl-$C_{1-4}$alkyl, piperidinyl-$C_{1-4}$alkyl and piperazinyl-$C_{1-4}$alkyl, wherein $R^6$ may be optionally substituted on carbon by one or more substituents selected from halo, hydroxy, amino, $C_{1-4}$alkyl, $C_{1-4}$alkoxy, N—($C_{1-4}$alkyl)amino and N,N—($C_{1-4}$alkyl)$_2$amino, and wherein any —NH— in a azetidinyl, pyrrolidinyl, piperidinyl, morpholinyl, piperidinyl or piperazinyl group in $R^6$ is optionally substituted by $C_{1-4}$alkyl, and wherein any azetidinyl, pyrrolidinyl, piperidinyl, morpholinyl, piperidinyl or piperazinyl group in $R^6$ optionally bears 1 oxo substituent.

(71) $R^6$ is selected from H, $C_{1-6}$alkyl, cyclopropyl, cyclobutyl, cyclopentyl, cyclohexyl, phenyl-$C_{1-4}$alkyl, cyclopropyl-$C_{1-4}$alkyl, cyclobutyl-$C_{1-4}$alkyl, cyclopentyl-$C_{1-4}$alkyl, cyclohexyl-$C_{1-4}$alkyl, azetidinyl-$C_{1-4}$alkyl, pyrrolidinyl-$C_{1-4}$alkyl, morpholinyl-$C_{1-4}$alkyl, piperidinyl-$C_{1-4}$alkyl, imidazolidinyl-$C_{1-4}$alkyl, piperazinyl-$C_{1-4}$alkyl and pyridinyl-$C_{1-4}$alkyl, wherein $R^6$ may be optionally substituted on carbon by one or more substituents selected from halo, hydroxy, amino, $C_{1-4}$alkyl, $C_{1-4}$alkoxy, N—($C_{1-4}$alkyl)amino and N,N—($C_{1-4}$alkyl)$_2$amino, and wherein any —NH— in a azetidinyl, pyrrolidinyl, piperidinyl, morpholinyl, imidazolidinyl, piperidinyl or piperazinyl group in $R^6$ is optionally substituted by $C_{1-4}$alkyl, and wherein any azetidinyl, pyrrolidinyl, piperidinyl, morpholinyl, piperidinyl or piperazinyl group in $R^6$ optionally bears 1 oxo substituent.

(72) $R^6$ is selected from H, $C_{1-6}$alkyl, cyclopropyl-$C_{1-4}$alkyl, phenyl-$C_{1-4}$alkyl, pyrrolidinyl-$C_{1-4}$alkyl, morpholinyl-$C_{1-4}$alkyl, imidazolidinyl-$C_{1-4}$alkyl, piperazinyl-$C_{1-4}$alkyl and pyridinyl-$C_{1-4}$alkyl, wherein $R^6$ may be optionally substituted on carbon by one or more substituents selected from halo, $C_{1-4}$alkoxy and N,N—($C_{1-4}$alkyl)$_2$amino, and wherein any pyrrolidinyl, morpholinyl, imidazolidinyl or piperazinyl group in $R^6$ optionally bears 1 oxo substituent.

(73) $R^6$ is selected from H, methyl, ethyl, 3-methoxypropyl, 2-phenylethyl, 2-piperazin-1-ylethyl, 2,2-difluoroethyl, 3-methylbutyl, propyl, benzyl, cyclopropylmethyl, 2-pyrrolidin-1-ylethyl, 2-(dimethylamino)-2-methylpropyl, 3-(dimethylamino)propyl, 2-morpholin-4-ylethyl, 2-pyridin-4-ylethyl, 2-pyridin-3-ylethyl, 3-pyridin-3-ylpropyl, 2-(2-oxoimidazolidin-1-yl)ethyl and 2-(2-oxopyrrolidin-1-yl)ethyl.

(74) $R^6$ is selected from H and $C_{1-4}$alkyl. For example $R^6$ is selected from H, methyl or ethyl, particularly $R^6$ is H or methyl.

(75) $R^7$ is selected from H, halo, hydroxy, trifluoromethoxy, mercapto, $C_{1-6}$alkyl, $C_{2-6}$alkenyl, $C_{2-6}$alkynyl, $C_{1-6}$alkoxy, $C_{1-6}$alkylS(O)$_a$ wherein a is 0 to 2,
wherein $R^7$ may be optionally substituted on carbon by one or more $R^{15}$;

$R^{15}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^8$—, aryl-$X^8$—, heterocyclyl-$X^9$— or heteroaryl-$X^{10}$—, and wherein $R^{15}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{15}$ may optionally bear 1 or 2 oxo substituents, and wherein any aryl or heteroaryl group within $R^{15}$ may optionally bear a $C_{1-3}$alkylenedioxy group;

$R^{19}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{19}$ may be optionally substituted on carbon by one or more $R^{20}$;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino;

$R^{20}$ is selected from halo, amino, methyl, ethyl, methoxy, ethoxy, methylamino, ethylamino, dimethylamino, diethylamino and N-methyl-N-ethylamino; and $X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— or —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2.

(76) $R^7$ is selected from H, halo, hydroxy, trifluoromethoxy, mercapto, $C_{1-6}$alkyl, $C_{2-6}$alkenyl, $C_{2-6}$alkynyl, $C_{1-6}$alkoxy, $C_{1-6}$alkylS(O)$_a$ wherein a is 0 to 2,
wherein $R^7$ may be optionally substituted on carbon by one or more $R^{15}$;

$R^{15}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^8$—, aryl-$X^8$—, heterocyclyl-$X^9$— or heteroaryl-$X^{10}$—, and wherein $R^{15}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{15}$ may optionally bear 1 or 2 oxo substituents, and wherein any aryl or heteroaryl group within $R^{15}$ may optionally bear a $C_{1-3}$alkylenedioxy group;

$R^{19}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{19}$ may be optionally substituted on carbon by one or more $R^{20}$;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino;

$R^{20}$ is selected from halo, amino, methyl, ethyl, methoxy, ethoxy, methylamino, ethylamino, dimethylamino, diethylamino and N-methyl-N-ethylamino; and $X^8$, $X^9$ and $X^{10}$ are independently selected from —O—, —N($R^{21}$)— or —S(O)$_q$—; wherein $R^{21}$ is selected from hydrogen and $C_{1-4}$alkyl and q is 0-2.

(77) $R^7$ is selected from H, halo, hydroxy, mercapto, $C_{1-4}$alkyl, $C_{2-4}$alkenyl, $C_{2-4}$alkynyl, $C_{1-4}$alkoxy and $C_{1-4}$alkyl-S—, wherein $R^7$ may be optionally substituted on carbon by one or more $R^{15}$;

$R^{15}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O), wherein a is 0 to 2, $C_{1-4}$alkoxycarbonyl, N—($C_{1-4}$alkyl)sulfamoyl, N,N—($C_{1-4}$alkyl)$_2$sulfamoyl, cyclopropyl, cyclobutyl, cyclopentyl, cyclohexyl, phenyl, a heteroaryl selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and a heterocyclyl selected from azetidinyl, pyrrolidinyl, morpholinyl, piperidinyl and piperazinyl, and wherein $R^{15}$ may be optionally substituted on carbon by one or more $R^{18}$, and wherein if any of said heterocyclyl or heteroaryl contains an —NH— moiety that nitrogen may be optionally substituted by a group selected from $R^{19}$;

and wherein any heterocyclyl group within $R^{15}$ may optionally bear 1 oxo substituent;

$R^{19}$ is selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl; and $R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino.

(78) $R^7$ is selected from H, halo, hydroxy, mercapto, $C_{1-4}$alkyl, $C_{1-4}$alkoxy and $C_{1-4}$alkyl-S—, wherein $R^7$ may be optionally substituted on carbon by one or more substituents selected from halo, hydroxy, amino, $C_{1-4}$alkoxy, N—($C_{1-4}$alkyl)amino and N,N—($C_{1-4}$alkyl)$_2$amino, cyclopropyl, cyclobutyl, cyclopentyl, cyclohexyl, azetidinyl, pyrrolidinyl, morpholinyl, piperidinyl and piperazinyl, and wherein any —NH— in a azetidinyl, pyrrolidinyl, piperidinyl, morpholinyl, piperidinyl or piperazinyl group in $R^7$ is optionally substituted by $C_{1-4}$alkyl, and wherein any azetidinyl, pyrrolidinyl, piperidinyl, morpholinyl, piperidinyl or piperazinyl group in $R^7$ optionally bears 1 oxo substituent.

(79) $R^7$ is selected from H, halo, hydroxy, mercapto, $C_{1-4}$alkyl, $C_{1-4}$alkoxy and $C_{1-4}$alkyl-S—, wherein $R^7$ may be optionally substituted on carbon by 1 or 2 substituents selected from halo, hydroxy, amino, $C_{1-4}$alkyl, $C_{1-4}$alkoxy, N—($C_{1-4}$alkyl)amino and N,N—($C_{1-4}$alkyl)$_2$amino.

(80) $R^7$ is selected from H, halo, $C_{1-4}$alkyl and $C_{1-4}$alkyl-S— (particularly H, halo and $C_{1-4}$alkyl).

(81) $R^7$ is selected from H, chloro, methyl and methylthio (particularly H, chloro and methyl, more particularly H and chloro).

(82) $R^7$ is selected from H, halo and $C_{1-4}$alkyl. For example, $R^7$ is H, fluoro, chloro, bromo, methyl or ethyl, particularly $R^7$ is H or methyl.

(83) $R^7$ is H or halo (particularly $R^7$ is halo such as chloro or bromo, more particularly chloro. Alternatively $R^7$ is H).

(84) A is $CR^{10}R^{11}$, wherein $R^{10}$ is H and $R^{11}$ is selected from H or $C_{1-6}$alkyl, wherein $R^{11}$ may be optionally substituted on carbon by one or more $R^{13}$;

$R^{13}$ is selected from nitro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$—, piperidinyl-$X^9$—, wherein $X^8$, $X^9$ and $X^{10}$ each represent a direct bond;

and wherein $R^{13}$ may be optionally substituted on carbon by one or more $R^{18}$, and wherein if said heterocyclyl or heteroaryl contains an —NH— moiety that nitrogen may be optionally substituted by a group selected from $R^{19}$;

$R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino, N,N—($C_{1-4}$alkyl)$_2$amino, $C_{1-4}$alkylS(O)$_a$ wherein a is 0 to 2, N—($C_{1-4}$alkyl)carbamoyl, N,N—($C_{1-4}$alkyl)$_2$carbamoyl, piperazinyl, pyrrolidinyl, piperidinyl and morpholinyl; and $R^{19}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

(85) A is $CR^{10}R^{11}$, wherein $R^{10}$ is H and $R^{11}$ is selected from H, $C_{1-6}$alkyl, $C_{3-7}$cycloalkyl-$X^2$—, phenyl-$X^2$, heterocyclyl-$X^3$— or heteroaryl-$X^4$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridinyl, pyridazinyl, pyrimidinyl and pyrazinyl, wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl, wherein said $C_{3-7}$cycloalkyl is selected from cyclopropyl, cyclobutyl, cyclopentyl and cyclohexyl, wherein $X^2$, $X^3$ and $X^4$ are independently selected from a direct bond, —C(O)— and —N($R^{22}$)C(O)—, wherein $R^{22}$ is hydrogen or $C_{1-4}$alkyl;

wherein $R^{11}$ may be optionally substituted on carbon by one or more $R^{13}$;

$R^{13}$ is selected from nitro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$—, piperidinyl-$X^9$—, wherein $X^8$, $X^9$ and $X^{10}$ each represent a direct bond;

and wherein $R^{13}$ may be optionally substituted on carbon by one or more $R^{18}$, and wherein if said heterocyclyl or heteroaryl contains an —NH— moiety that nitrogen may be optionally substituted by a group selected from $R^{19}$;

$R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino, N,N—($C_{1-4}$alkyl)$_2$amino, $C_{1-4}$alkylS(O)$_a$ wherein a is 0 to 2, N—($C_{1-4}$alkyl)carbamoyl, N,N—($C_{1-4}$alkyl)$_2$carbamoyl, piperazinyl, pyrrolidinyl, piperidinyl and morpholinyl; and $R^{19}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

(86) $R^6$ is selected from H, $C_{1-6}$alkyl and $C_{2-6}$alkynyl (particularly H and $C_{1-6}$alkyl), and wherein $R^6$ may be optionally substituted on carbon by one or more $R^{16}$; and wherein if said heterocyclyl or heteroaryl contains an —NH— moiety that nitrogen may be optionally substituted by a group selected from $R^{17}$;

wherein $R^{16}$ is selected from fluoro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$—, piperidinyl-$X^9$— and morpholinyl-$X^9$—, wherein $X^8$, $X^9$ and $X^{10}$ each represent a direct bond; and wherein $R^{16}$ is optionally substituted with one or more $R^{18}$;

wherein $R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino and N,N—($C_{1-4}$alkyl)$_2$amino; and wherein $R^{17}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

(87) $R^6$ is selected from H, $C_{1-6}$alkyl, $C_{3-7}$cycloalkyl-$X^5$—, phenyl-$X^5$—, heterocyclyl-$X^6$— and heteroaryl-$X^7$—, wherein said heterocyclyl is a monocyclic 5 or 6-membered heterocyclyl ring containing 1, 2 or 3 (suitably 1 or 2) heteroatoms selected from O, S and N, and wherein said heteroaryl is a monocyclic 5, 6 or 7-membered heteroaryl ring containing 1, 2 or 3 heteroatoms selected from O, S and N, and wherein $X^5$, $X^6$ and $X^7$ are each independently selected from a direct bond or —N($R^{12}$)C(O)—, wherein $R^{12}$ is hydrogen or $C_{1-4}$alky, and wherein $R^6$ may be optionally substituted on carbon by one or more $R^{16}$; and wherein if said heterocyclyl or heteroaryl contains an —NH— moiety that nitrogen may be optionally substituted by a group selected from $R^{17}$;

wherein $R^{16}$ is selected from fluoro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$—, piperidinyl-$X^9$— and morpholinyl-$X^9$—, wherein $X^8$, $X^9$ and $X^{10}$ each represent a direct bond;

and wherein $R^{16}$ is optionally substituted with one or more $R^{18}$;

wherein $R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino and N,N—($C_{1-4}$alkyl)$_2$amino; and $R^{17}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

In an embodiment of the invention there is provided a compound of the formula I which is of the formula IA:

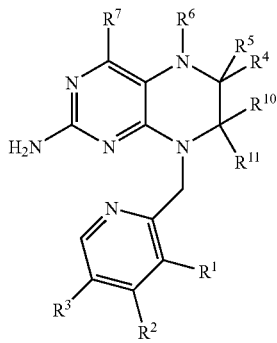

IA wherein $R^4$, $R^5$, $R^6$, $R^7$, $R^{10}$ and $R^{11}$ have any of the meanings defined hereinbefore or hereinafter;

$R^1$ is selected from H, halo, $C_{1-3}$alkyl and $C_{1-3}$alkoxy (for example $R^1$ is H, halo or $C_{1-3}$alkyl, particularly, $R^1$ is methyl, chloro or bromo);

$R^2$ is selected from halo, $C_{1-3}$alkyl and $C_{1-3}$alkoxy (for example $R^1$ is selected from chloro, bromo, iodo, methyl and methoxy); and $R^3$ is selected from H, halo and $C_{1-3}$-alkyl;

or an N-oxide thereof;

or a pharmaceutically acceptable salt thereof.

In another embodiment of the invention there is provided a compound of the formula I which is of the formula IB:

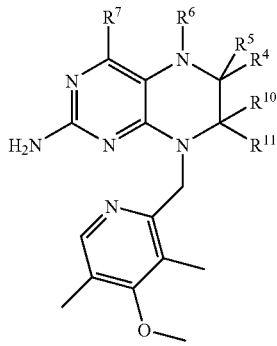

IB wherein $R^4$, $R^5$, $R^6$, $R^7$, $R^{10}$ and $R^{11}$ have any of the meanings defined hereinbefore or hereinafter;

or a pharmaceutically acceptable salt thereof.

In one embodiment of the invention there is provided a compound of the formula I or formula IA or formula IB as hereinbefore defined wherein:

$R^4$ is H;

$R^5$ is H or $C_{1-4}$alkyl or $R^4$ and $R^5$ together form oxo (for example $R^4$ is H, $R^5$ is H or methyl, or $R^4$ and $R^5$ together form oxo);

$R^6$ is selected from H, $C_{1-4}$alkyl, $C_{2-4}$alkenyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)$_2$carbamoyl (for example $R^6$ is H or $C_{1-4}$alkyl);

$R^7$ is selected from H, halo, hydroxy, trifluoromethoxy, mercapto, $C_{1-4}$alkyl, $C_{2-4}$alkenyl, $C_{2-4}$alkynyl, $C_{1-4}$alkoxy, $C_{1-4}$alkylS(O)$_a$ wherein a is 0 to 2 (for example $R^7$ is selected from H, halo, hydroxy, $C_{1-4}$alkyl and $C_{1-4}$alkoxy, particularly $R^7$ is selected from H, halo, methyl, ethyl, and methoxy, more particularly $R^7$ is selected from H, chloro and bromo);

A in the compound of the formula I is $CR^{10}R^{11}$;

$R^{10}$ in the compounds of the formulae I and IA is H;

$R^{11}$ in the compounds of the formulae I and IA is selected from H, cyano, carboxy, carbamoyl, sulfamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylaminocarbonyl, carbocyclyl-$X^2$—, heterocyclyl-$X^3$— or heteroaryl-$X^4$—, wherein $R^{11}$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 or 2 oxo or thioxo substituents;

and wherein any carbocyclyl, heterocyclyl or heteroaryl group within $R^{11}$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{13}$ may be optionally substituted on carbon by one or more $R^{18}$, and wherein if said heterocyclyl or heteroaryl contains an —NH— moiety that nitrogen may be optionally substituted by a group selected from $R^{19}$, and wherein any heterocyclyl group within $R^{13}$ may optionally bear 1 or 2 oxo or thioxo substituents, and wherein any carbocyclyl, heterocyclyl or heteroaryl group within $R^{13}$ may optionally bear a $C_{1-3}$alkylenedioxy group;

$R^{14}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$ may be optionally substituted on carbon by one or more $R^{20}$;

$X^2$, $X^3$ and $X^4$ are independently selected from a direct bond, —C(O)— and —N($R^{22}$)C(O)—;

wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— or —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

and wherein any carbocyclyl, heterocyclyl or heteroaryl group within $R^{18}$ may optionally bear a $C_{1-3}$alkylenedioxy group;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ is selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

In this embodiment particular values for $R^{11}$ include, for example any of those described in paragraphs (40) to (50), (84) and (85) described hereinbefore.

In another embodiment of the invention there is provided a compound of the formula I or formula IA of formula IB as hereinbefore defined wherein:

A in the compound of the formula I is CR$^{10}$R$^{11}$;

$R^{10}$ in the compounds of the formulae I, IA and IB is H;

$R^{11}$ in the compounds of the formulae I, IA and IB is H or $C_{1-4}$alkyl, or $R^{10}$ and $R^{11}$ together form oxo;

$R^6$ is selected from H, $C_{1-4}$alkyl, $C_{2-4}$alkenyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)$_2$carbamoyl (for example $R^6$ is H or $C_{1-4}$alkyl);

$R^7$ is selected from H, halo, hydroxy, trifluoromethoxy, mercapto, $C_{1-4}$alkyl, $C_{2-4}$alkenyl, $C_{2-4}$alkynyl, $C_{1-4}$alkoxy, $C_{1-4}$alkylS(O)$_a$ wherein a is 0 to 2 (for example $R^7$ is selected from H, halo, hydroxy, $C_{1-4}$alkyl and $C_{1-4}$alkoxy, particularly $R^7$ is selected from H, halo, methyl, ethyl, and methoxy, more particularly $R^7$ is selected from H, chloro and bromo);

$R^4$ is H;

$R^5$ is selected from H, cyano, carboxy, carbamoyl, sulfamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylaminocarbonyl, carbocyclyl-$X^2$—, heterocyclyl-$X^3$— or heteroaryl-$X^4$—, wherein $R^5$ may be optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^5$ may optionally bear 1 or 2 oxo or thioxo substituents;

and wherein any carbocyclyl, heterocyclyl or heteroaryl group within $R^5$ may optionally bear a $C_{1-3}$alkylenedioxy group;

$R^{13}$ is selected from halo, nitro, cyano, hydroxy, trifluoromethoxy, amino, carboxy, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{13}$ may be optionally substituted on carbon by one or more $R^{18}$, and wherein if said heterocyclyl or heteroaryl contains an —NH— moiety that nitrogen may be optionally substituted by a group selected from $R^{19}$, and wherein any heterocyclyl group within $R^{13}$ may optionally bear 1 or 2 oxo or thioxo substituents, and wherein any carbocyclyl, heterocyclyl or heteroaryl group within $R^{13}$ may optionally bear a $C_{1-3}$alkylenedioxy group;

$R^{14}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$ may be optionally substituted on carbon by one or more $R^{20}$;

$X^2$, $X^3$ and $X^4$ are independently selected from a direct bond, —C(O)— and —N($R^{22}$)C(O)—; wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— and —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

and wherein any carbocyclyl, heterocyclyl or heteroaryl group within $R^{18}$ may optionally bear a $C_{1-3}$alkylenedioxy group;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ is selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

In this embodiment particular values for $R^5$ include, for example any of those described in paragraphs (54) to (61) described hereinbefore.

In another embodiment of the invention there is provided a compound of the formula I, formula IA or formula IB as hereinbefore defined wherein:

$R^4$ and $R^5$ are independently H or $C_{1-4}$alkyl or $R^4$ and $R^5$ together form oxo (for example $R^4$ is H, $R^5$ is $C_{1-4}$alkyl such as methyl, or $R^4$ and $R^5$ together form oxo);

A in the compound of the formula I is $CR^{10}R^{11}$;

$R^{10}$ in the compounds of the formulae I, IA and IB is H;

$R^{11}$ in the compounds of the formulae I, IA and IB is H or $C_{1-4}$alkyl;

$R^7$ is selected from H, halo, hydroxy, trifluoromethoxy, mercapto, $C_{1-4}$alkyl, $C_{2-4}$alkenyl, $C_{2-4}$alkynyl, $C_{1-4}$alkoxy, $C_{1-4}$alkylS(O)$_a$ wherein a is 0 to 2 (for example $R^7$ is selected from H, halo, hydroxy, $C_{1-4}$alkyl and $C_{1-4}$alkoxy, particularly $R^7$ is selected from H, halo, methyl, ethyl, and methoxy, more particularly $R^7$ is selected from H, chloro and bromo);

$R^6$ is selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, carbocyclyl-$X^5$—, heterocyclyl-$X^6$— or heteroaryl-$X^7$—, wherein $X^5$, $X^6$ and $X^7$ are independently selected from a direct bond, —C(O)—, —N($R^{12}$)C(O)— and —SO$_2$—;

wherein $R^{12}$ is selected from hydrogen or $C_{1-4}$alkyl, and wherein $R^6$ may be optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 or 2 thioxo substituents;

and wherein any carbocyclyl, heterocyclyl or heteroaryl group within $R^6$ may optionally bear a $C_{1-3}$alkylenedioxy group;

$R^{16}$ is selected from halo, nitro, cyano, hydroxy, trifluoromethoxy, amino, carboxy, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{16}$ may be optionally substituted on carbon by one or more $R^{18}$, and wherein if said heterocyclyl or heteroaryl contains an —NH— moiety that nitrogen may be optionally substituted by a group selected from $R^{19}$, and wherein any heterocyclyl group within $R^{16}$ may optionally bear 1 or 2 oxo or thioxo substituents and wherein any carbocyclyl, heterocyclyl or heteroaryl group within $R^{16}$ may optionally bear a $C_{1-3}$alkylenedioxy group;

$R^{17}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{17}$ may be optionally substituted on carbon by one or more $R^{20}$;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— or —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O), wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

In this embodiment particular values for $R^6$ include, for example any of those described in paragraphs (62) to (74), (86) and (87) described hereinbefore.

In one embodiment there is provided a compound of the formula I, IA or IB, wherein A is $CR^{10}R^{11}$ and $R^{10}$ is hydrogen, which is a compound selected from a compound of the formula I*, IA* and IB*, or a pharmaceutically acceptable salt or an N-oxide thereof:

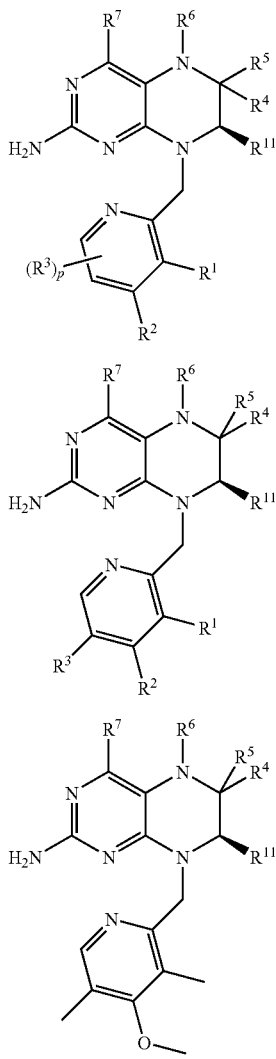

wherein $R^1$, $R^2$, $R^3$, $R^4$, $R^5$, $R^6$, $R^7$, $R^{11}$ and p are as hereinbefore in relation to compounds of the formulae I, IA and IB respectively. Particular compounds of the formula I, IA or IB are those wherein $R^{11}$ is hydrogen or $C_{1-4}$alkyl (particularly $R^{11}$ is $C_{1-4}$alkyl).

In another embodiment are compounds of the formula I*, IA* or IB* wherein $R^7$ is chloro. For example those compounds wherein $R^7$ is chloro and $R^{11}$ is hydrogen or $C_{1-4}$alkyl, wherein $R^{11}$ is optionally substituted on carbon by one or more $R^{13}$ selected from halo, cyano, hydroxy, amino, carboxy, carbamoyl, mercapto, sulfamoyl, $C_{1-4}$alkoxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkoxycarbonyl, $C_{1-4}$alkylS(O)$_a$ wherein a is 0 to 2, N—($C_{1-6}$alkyl)sulfamoyl, N,N—($C_{1-4}$alkyl)$_2$sulfamoyl, $C_{1-4}$alkylsulfonylamino, phenyl, pyridyl or pyrimidinyl. More particularly those compounds wherein $R^7$ is chloro and $R^{11}$ is selected from hydrogen and $C_{1-4}$alkyl (for example $R^{11}$ is $C_{1-4}$alkyl).

In another embodiment of the invention there is provided a compound of the formula I, formula IA or formula IB as hereinbefore defined wherein:

$R^4$ and $R^5$ are independently H or $C_{1-4}$alkyl or $R^4$ and $R^5$ together form oxo (for example $R^4$ is H, $R^5$ is $C_{1-4}$alkyl such as methyl, or $R^4$ and $R^5$ together form oxo);

A in the compound of the formula I is $CR^{10}R^{11}$;

$R^{10}$ in the compounds of the formulae I, IA and IB is H;

$R^{11}$ in the compounds of the formulae I, IA and IB is H or $C_{1-4}$alkyl, wherein $R^{11}$ is optionally substituted on carbon by one or more $R^{13}$ selected from halo, cyano, hydroxy, amino, carboxy, carbamoyl, mercapto, sulfamoyl, $C_{1-4}$alkoxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkoxycarbonyl, $C_{1-4}$alkylS(O)$_a$ wherein a is 0 to 2, N—($C_{1-6}$alkyl)sulfamoyl, N,N—($C_{1-4}$alkyl)$_2$sulfamoyl, $C_{1-4}$alkylsulfonylamino, phenyl, pyridyl or pyrimidinyl (particularly $R^{11}$ is H or $C_{1-4}$alkyl);

$R^6$ is selected from H, $C_{1-4}$alkyl, $C_{2-4}$alkenyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)$_2$carbamoyl (for example $R^6$ is H or $C_{1-4}$alkyl); and $R^7$ is selected from H, halo and $C_{1-4}$alkyl (for example $R^7$ is selected from H, halo, hydroxy, $C_{1-4}$alkyl and $C_{1-4}$alkoxy, particularly $R^7$ is selected from H, halo, methyl, ethyl, and methoxy, more particularly $R^7$ is selected from H, chloro and bromo);

or a pharmaceutically acceptable salt thereof.

In another embodiment of the invention there is provided a compound of the formula I, formula IA or formula IB as hereinbefore defined wherein when A is $CR^{10}R^{11}$, $R^{10}$ and $R^{11}$ together do not form an oxo group.

In an embodiment of the invention there is provided a compound of the formula I which is of the formula IC:

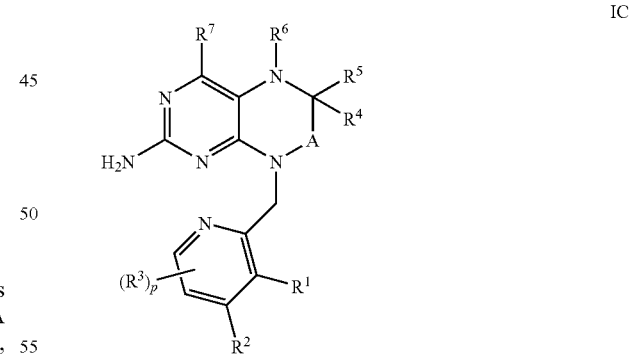

wherein:

$R^1$, $R^2$ and $R^3$ are independently selected from halo, cyano, nitro or a group of the formula:

—$X^1$—$R^8$, wherein $X^1$ is a direct bond, O or S and $R^8$ is $C_{1-4}$alkyl, p is 1 or 2;

A is $CR^{10}R^{11}$;

$R^4$ and $R^{10}$ are independently selected from H and $C_{1-4}$alkyl;

$R^5$ is selected from H, cyano, carboxy, carbamoyl, $C_{1-4}$alkyl, $C_{2-4}$alkenyl, $C_{2-4}$alkynyl, $C_{1-4}$alkanoyl and $C_{1-4}$alkoxycarbonyl;

$R^{11}$ is selected from H, cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, $C_{1-6}$alkylsulfonylaminocarbonyl, carbocyclyl-$X^2$—, heterocyclyl-$X^3$— or heteroaryl-$X^4$—, wherein $R^{11}$ is optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 or 2 oxo or thioxo substituents;

or $R^4$ and $R^5$ together form oxo (=O);

or $R^{10}$ and $R^{11}$ together form oxo (=O);

$R^6$ is selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, carbocyclyl-$X^5$—, heterocyclyl-$X^6$— or heteroaryl-$X^7$—, wherein $X^5$, $X^6$ and $X^7$ are independently selected from a direct bond, —C(O)—, —N($R^{12}$)C(O)— and —SO$_2$—; wherein $R^{12}$ is selected from hydrogen or $C_{1-4}$alkyl, and wherein $R^6$ is optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 or 2 oxo or thioxo substituents;

$R^7$ is selected from H, halo, $C_{1-4}$alkyl and $C_{1-4}$alkylS(O)$_a$ wherein a is 0, $R^{13}$ and $R^{16}$ are independently selected from halo, nitro, cyano, hydroxy, trifluoromethoxy, amino, carboxy, carboxyamino, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{13}$ and $R^{16}$ may be optionally substituted on carbon by one or more $R^{18}$, and wherein if said heterocyclyl or heteroaryl contains an —NH— moiety that nitrogen may be optionally substituted by a group selected from $R^{19}$, and wherein any heterocyclyl group within $R^{13}$ and $R^{16}$ may optionally bear 1 or 2 oxo or thioxo substituents;

$R^{14}$, $R^{17}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$, $R^{17}$ and $R^{19}$ independently of each other may be optionally substituted on carbon by one or more $R^{20}$;

$X^2$, $X^3$ and $X^4$ are independently selected from a direct bond, —C(O)— and —N($R^{22}$)C(O)—; wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— and —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O), wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

In particular, in the compounds of formula IC, $R^1$, $R^2$ and $R^3$ are independently selected from bromo, cyano, nitro, methyl, methoxy and methylthio. More particularly, in the compounds of formula IC, $R^1$, $R^2$ and $R^3$ are independently selected from methyl and methoxy and p is 1.

In particular, in the compounds of formula IC, $R^4$ and $R^5$ are both H or $R^4$ and $R^5$ together form oxo (=O).

In particular, in the compounds of formula IC, $R^7$ is selected from H, chloro, methyl and methylthio, more particularly H and chloro, and even more particularly $R^7$ is chloro.

In one embodiment there is provided a compound of the formula IC of the formula IC*, or a pharmaceutically acceptable salt or an N-oxide thereof:

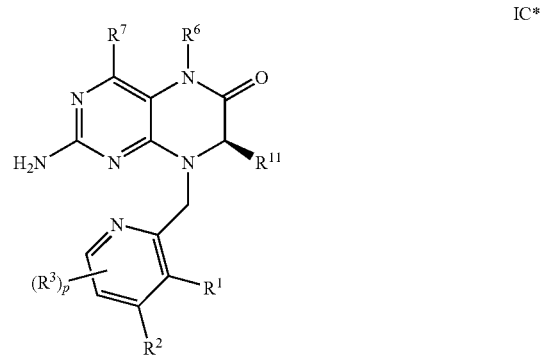

IC* wherein $R^1$, $R^2$, $R^3$, $R^6$, $R^7$, $R^{11}$ and p are as hereinbefore defined in relation to a compound of the formula IC.

Particular compounds of the formula IC* are those wherein $R^{11}$ is H or $C_{1-4}$alkyl, wherein $R^{11}$ is optionally substituted on carbon by one or more $R^{13}$ selected from halo, cyano, hydroxy, amino, carboxy, carbamoyl, mercapto, sulfamoyl, $C_{1-4}$alkoxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkoxycarbonyl, $C_{1-4}$alkylS(O)$_a$ wherein a is 0 to 2, N—($C_{1-6}$alkyl)sulfamoyl, N,N—($C_{1-4}$alkyl)$_2$sulfamoyl, $C_{1-4}$alkylsulfonylamino, phenyl, pyridyl or pyrimidinyl. More particularly $R^{11}$ is selected from H and $C_{1-4}$alkyl.

Other particular compounds of the formula IC* are those wherein $R^7$ is chloro. For example compounds of the formula IC* wherein $R^7$ is chloro and $R^{11}$ is selected from H and $C_{1-4}$alkyl (For example $R^{11}$ is methyl. Alternatively $R^{11}$ is hydrogen).

In an embodiment of the invention there is provided a compound of the formula I which is of the formula ID:

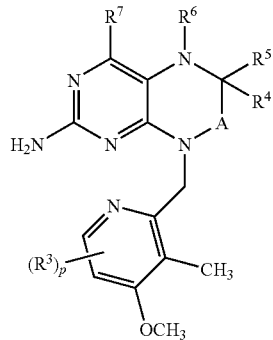

ID wherein:

$R^3$ is selected from halo, cyano, nitro or a group of the formula:

—$X^1$—$R^8$, wherein $X^1$ is a direct bond, O or S and $R^8$ is $C_{1-4}$alkyl,
p is 1 or 2;
A is $CR^{10}R^{11}$;
$R^4$ and $R^5$ are both H, or $R^4$ and $R^5$ together form oxo (=O);
$R^{10}$ is H;
$R^{11}$ is selected from H, cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, $C_{1-6}$alkylsulfonylaminocarbonyl, carbocyclyl-$X^2$—, heterocyclyl-$X^3$— or heteroaryl-$X^4$—, wherein $R^{11}$ is optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 or 2 oxo or thioxo substituents;

and wherein any carbocyclyl, heterocyclyl or heteroaryl group within $R^{11}$ may optionally bear a $C_{1-3}$alkylenedioxy group;

$R^6$ is selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, carbocyclyl-$X^5$—, heterocyclyl-$X^6$— or heteroaryl-$X^7$—, wherein $X^5$, $X^6$ and $X^7$ are independently selected from a direct bond, —C(O)—, —N($R^{12}$)C(O)— and —SO$_2$—;
wherein $R^{12}$ is selected from hydrogen or $C_{1-4}$alkyl, and wherein $R^6$ is optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 or 2 oxo or thioxo substituents;

and wherein any carbocyclyl, heterocyclyl or heteroaryl group within $R^6$ may optionally bear a $C_{1-3}$alkylenedioxy group $R^7$ is selected from H, halo, $C_{1-4}$alkyl and $C_{1-4}$alkylS(O)$_a$ wherein a is 1, $R^{13}$ and $R^{16}$ are independently selected from halo, nitro, cyano, hydroxy, trifluoromethoxy, amino, carboxy, carboxyamino, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{13}$ and $R^{16}$ may be optionally substituted on carbon by one or more $R^{18}$, and wherein if said heterocyclyl or heteroaryl contains an —NH— moiety that nitrogen may be optionally substituted by a group selected from $R^{19}$, and wherein any heterocyclyl group within $R^{13}$ and $R^{16}$ may optionally bear 1 or 2 oxo or thioxo substituents and wherein any carbocyclyl, heterocyclyl or heteroaryl group within $R^{13}$ and $R^{16}$ may optionally bear a $C_{1-3}$alkylenedioxy group;

$R^{14}$, $R^{17}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$, $R^{17}$ and $R^{19}$ independently of each other may be optionally substituted on carbon by one or more $R^{20}$;

$X^2$, $X^3$ and $X^4$ are independently selected from a direct bond, —C(O)— and —N($R^{22}$)C(O)—; wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— and —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

and wherein any carbocyclyl, heterocyclyl or heteroaryl group within $R^{18}$ may optionally bear a $C_{1-3}$alkylenedioxy group;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

In particular, in the compounds of formula ID, $R^3$ is —$X^1$—$R^8$ wherein $X^1$ is O and $R^8$ is $C_{1-4}$alkyl (more particularly $R^3$ is methoxy) and p is 1.

In particular, in the compounds of formula ID, $R^7$ is selected from H, chloro, methyl and methylthio. Particularly $R^7$ is chloro.

In one embodiment there is provided a compound of the formula ID of the formula ID*, or a pharmaceutically acceptable salt or an N-oxide thereof:

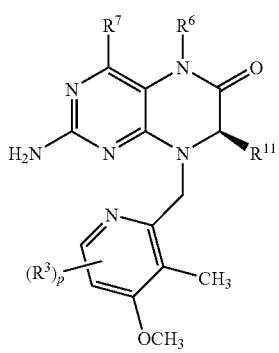

ID* wherein $R^3$, $R^6$, $R^7$, $R^{11}$ and p are as hereinbefore defined in relation to a compound of the formula ID.

Particular compounds of the formula ID* are those wherein $R^{11}$ is selected from H and $C_{1-4}$alkyl, wherein $R^{11}$ is optionally substituted on carbon by one or more $R^{13}$ selected from halo, cyano, hydroxy, amino, carboxy, carbamoyl, mercapto, sulfamoyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{1-4}$alkylsulfonylamino, phenyl, pyridyl and pyrimidinyl. Particularly $R^{11}$ is selected from hydrogen and $C_{1-4}$alkyl.

Other particular compounds of the formula ID* are those wherein $R^7$ is chloro. For example compounds of the formula ID* wherein $R^7$ is chloro and $R^{11}$ is selected from H and $C_{1-4}$alkyl (For example $R^{11}$ is methyl. Alternatively $R^{11}$ is H).

In an embodiment of the invention there is provided a compound of the formula I which is of the formula IE:

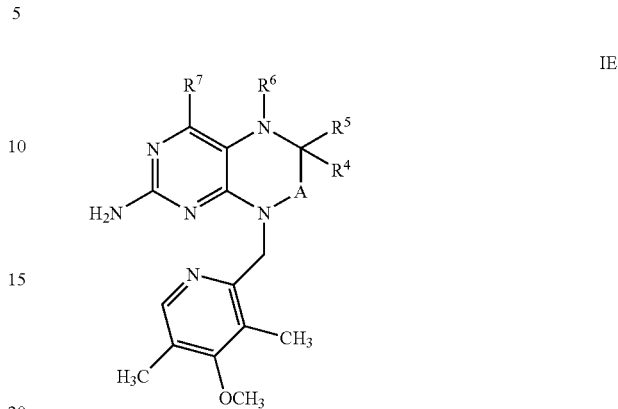

IE wherein:

A is $CR^{10}R^{11}$;

$R^4$ and $R^5$ are both H, or $R^4$ and $R^5$ together form oxo (=O);

$R^{10}$ is H;

$R^{11}$ is selected from H, cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, $C_{1-6}$alkylsulfonylaminocarbonyl, carbocyclyl-$X^2$—, heterocyclyl-$X^3$— or heteroaryl-$X^4$—, wherein $R^{11}$ is optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 or 2 oxo or thioxo substituents;

and wherein any carbocyclyl, heterocyclyl or heteroaryl group within $R^{11}$ may optionally bear a $C_{1-3}$alkylenedioxy group;

$R^6$ is selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, carbocyclyl-$X^5$—, heterocyclyl-$X^6$— or heteroaryl-$X^7$—, wherein $X^5$, $X^6$ and $X^7$ are independently selected from a direct bond, —C(O)—, —N($R^{12}$)C(O)— and —SO$_2$—; wherein $R^{12}$ is selected from hydrogen or $C_{1-4}$alkyl, and wherein $R^6$ is optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 or 2 oxo or thioxo substituents;

and wherein any carbocyclyl, heterocyclyl or heteroaryl group within $R^6$ may optionally bear a $C_{1-3}$alkylenedioxy group $R^7$ is selected from H, chloro, methyl and methylthio;

$R^{13}$ and $R^{16}$ are independently selected from halo, nitro, cyano, hydroxy, trifluoromethoxy, amino, carboxy, carboxyamino, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{13}$ and $R^{16}$ may be optionally substituted on carbon by one or more $R^{18}$ and wherein if said heterocyclyl or heteroaryl contains an —NH— moiety that nitrogen may be optionally substituted by a group selected from $R^{19}$, and wherein any heterocyclyl group within $R^{13}$ and $R^{16}$ may optionally bear 1 or 2 oxo or thioxo substituents and wherein any carbocyclyl, heterocyclyl or heteroaryl group within $R^{13}$ and $R^{16}$ may optionally bear a $C_{1-3}$alkylenedioxy group;

$R^{14}$, $R^{17}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$, $R^{17}$ and $R^{19}$ independently of each other may be optionally substituted on carbon by one or more $R^{20}$;

$X^2$, $X^3$ and $X^4$ are independently selected from a direct bond, —C(O)— and —N($R^{22}$)C(O)—; wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, S(O)$_q$—, —SO$_2$N($R^{24}$)— and —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

and wherein any carbocyclyl, heterocyclyl or heteroaryl group within $R^{18}$ may optionally bear a $C_{1-3}$alkylenedioxy group;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

In one embodiment there is provided a compound of the formula IE of the formula IE*, or a pharmaceutically acceptable salt or an N-oxide thereof:

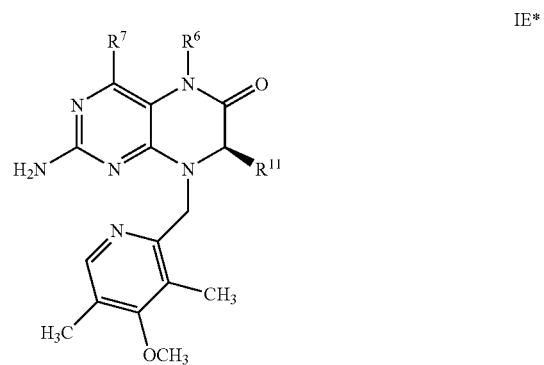

IE*

Particular compounds of the formula IE* are those wherein $R^{11}$ is selected from H and $C_{1-4}$alkyl, wherein $R^{11}$ is optionally substituted on carbon by one or more $R^{13}$ selected from halo, nitro, cyano, hydroxy, trifluoromethoxy, amino, carboxy, carboxyamino, carbamoyl, mercapto, sulfamoyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{1-4}$alkylsulfonylamino, phenyl, pyridyl and pyrimidinyl. Particularly $R^{11}$ is selected from H and $C_{1-4}$alkyl.

Other particular compounds of the formula IE* are those wherein $R^7$ is chloro. For example compounds of the formula IE* wherein $R^7$ is chloro and $R^{11}$ is selected from H and $C_{1-4}$alkyl (For example $R^{11}$ is methyl. Alternatively $R^{11}$ is H).

In an embodiment of the invention there is provided a compound of the formula I which is of the formula IF:

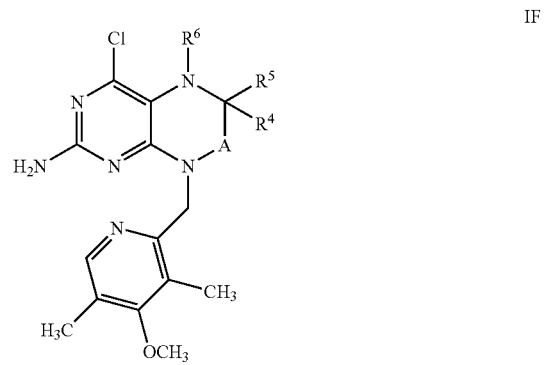

IF wherein:

A is $CR^{10}R^{11}$;

$R^4$ and $R^5$ are both H, or $R^4$ and $R^5$ together form oxo (=O);

$R^{10}$ is H;

$R^{11}$ is selected from H, cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, $C_{1-6}$alkylsulfonylaminocarbonyl, carbocyclyl-$X^2$—, heterocyclyl-$X^3$— or heteroaryl-$X^4$—, wherein $R^{11}$ is optionally substituted on carbon by one or more $R^{13}$; and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 or 2 oxo or thioxo substituents;

and wherein any carbocyclyl, heterocyclyl or heteroaryl group within $R^{11}$ may optionally bear a $C_{1-3}$alkylenedioxy group;

$R^6$ is selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, carbocyclyl-$X^5$—, heterocyclyl-$X^6$— or heteroaryl-$X^7$—, wherein $X^5$, $X^6$ and $X^7$ are independently selected from a direct bond, —C(O)—, —N($R^{12}$)C(O)— and —SO$_2$—; wherein $R^{12}$ is selected from hydrogen or $C_{1-4}$alkyl, and wherein $R^6$ is optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 or 2 oxo or thioxo substituents;

and wherein any carbocyclyl, heterocyclyl or heteroaryl group within $R^6$ may optionally bear a $C_{1-3}$alkylenedioxy group $R^{13}$ and $R^{16}$ are independently selected from halo, nitro, cyano, hydroxy, trifluoromethoxy, amino, carboxy, carboxyamino, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N'—($C_{1-6}$alkyl)ureido, N',N'—($C_{1-6}$alkyl)$_2$ureido, N,N',N'—($C_{1-6}$alkyl)$_3$ureido, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl-$X^8$—, heterocyclyl-$X^9$— or heteroaryl-$X^{10}$—, and wherein $R^{13}$ and $R^{16}$ may be optionally substituted on carbon by one or more $R^{18}$, and wherein if said heterocyclyl or heteroaryl contains an —NH— moiety that nitrogen may be optionally substituted by a group selected from $R^{19}$, and wherein any heterocyclyl group within $R^{13}$ and $R^{16}$ may optionally bear 1 or 2 oxo or thioxo substituents and wherein any carbocyclyl, heterocyclyl or heteroaryl group within $R^{13}$ and $R^{16}$ may optionally bear a $C_{1-3}$alkylenedioxy group;

$R^{14}$, $R^{17}$ and $R^{19}$ are independently selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{14}$, $R^{17}$ and $R^{19}$ independently of each other may be optionally substituted on carbon by one or more $R^{20}$;

$X^2$, $X^3$ and $X^4$ are independently selected from a direct bond, —C(O)— and —N($R^{22}$)C(O)—; wherein $R^{22}$ is hydrogen or $C_{1-4}$alkyl;

$X^8$, $X^9$ and $X^{10}$ are independently selected from a direct bond, —O—, —N($R^{21}$)—, —C(O)—, —N($R^{22}$)C(O)—, —C(O)N($R^{23}$)—, —S(O)$_q$—, —SO$_2$N($R^{24}$)— and —N($R^{25}$)SO$_2$—; wherein $R^{21}$, $R^{22}$, $R^{23}$, $R^{24}$ and $R^{25}$ are independently selected from hydrogen or $C_{1-4}$alkyl and q is 0-2;

$R^{18}$ is selected from halo, nitro, cyano, hydroxy, trifluoromethoxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulfamoyl, N,N—($C_{1-6}$alkyl)$_2$sulfamoyl, $C_{1-6}$alkylsulfonylamino, carbocyclyl, heterocyclyl or heteroaryl; wherein $R^{18}$ may be optionally substituted on carbon by one or more $R^{25}$;

and wherein if any of said heterocyclyl or heteroaryl contains an —NH— moiety that nitrogen may be optionally substituted by a group selected from $R^{26}$;

and wherein any heterocyclyl group within $R^{18}$ may optionally bear 1 or 2 oxo or thioxo substituents;

and wherein any carbocyclyl, heterocyclyl or heteroaryl group within $R^{18}$ may optionally bear a $C_{1-3}$alkylenedioxy group;

$R^{26}$ is selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl; wherein $R^{26}$ may be optionally substituted on carbon by one or more $R^{27}$; and $R^{20}$, $R^{25}$ and $R^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl or N-methyl-N-ethylsulfamoyl;

or an N-oxide thereof;

or a pharmaceutically acceptable salt thereof.

In one embodiment there is provided a compound of the formula IF of the formula IF*, or a pharmaceutically acceptable salt or an N-oxide thereof:

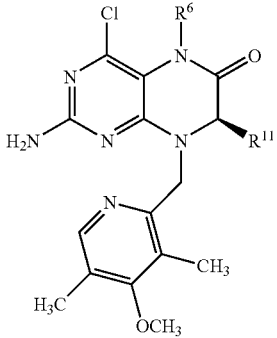

IF* wherein $R^6$ and $R^{11}$ are as hereinbefore defined in relation to a compound of the formula IF.

Particular compounds of the formula IF* are those wherein $R^{11}$ is selected from H and $C_{1-4}$alkyl, wherein $R^{11}$ is optionally substituted on carbon by one or more $R^{13}$ selected from halo, nitro, cyano, hydroxy, trifluoromethoxy, amino, carboxy, carboxyamino, carbamoyl, mercapto, sulfamoyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{1-4}$alkylsulfonylamino, phenyl, pyridyl and pyrimidinyl. Particularly $R^{11}$ is selected from H and $C_{1-4}$alkyl.

In one aspect of the compounds of formula IC, ID, IE and/or IF, $R^{10}$ is H and $R^{11}$ is selected from H or $C_{1-6}$alkyl,
wherein $R^{11}$ may be optionally substituted on carbon by one or more $R^{13}$;
$R^{13}$ is selected from nitro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$— or piperidinyl-$X^9$—, wherein $X^8$, $X^9$ and $X^{10}$ each represent a direct bond;
and wherein $R^{13}$ may be optionally substituted on carbon by one or more $R^{18}$,
and wherein if said heterocyclyl or heteroaryl contains an —NH— moiety that nitrogen may be optionally substituted by a group selected from $R^{19}$;
$R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino, N,N—($C_{1-4}$alkyl)$_2$amino, $C_{1-4}$alkylS(O)$_a$ wherein a is 0 to 2, N—($C_{1-4}$alkyl)carbamoyl, N,N—($C_{1-4}$alkyl)$_2$carbamoyl, piperazinyl-, pyrrolidinyl-, piperidinyl- and morpholinyl-, and
$R^{19}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

In another aspect of the compounds of formula IC, ID, IE and/or IF, $R^{10}$ is H and $R^{11}$ is selected from H, $C_{1-6}$alkyl, $C_{3-7}$cycloalkyl-$X^2$—, phenyl-$X^2$—, heterocyclyl-$X^3$— or heteroaryl-$X^4$—,
wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridinyl, pyridazinyl, pyrimidinyl and pyrazinyl,
wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl,
wherein said $C_{3-7}$cycloalkyl is selected from cyclopropyl, cyclobutyl, cyclopentyl and cyclohexyl,
wherein $X^2$, $X^3$ and $X^4$ are independently selected from a direct bond, —C(O)— and —N($R^{22}$)C(O)—, wherein $R^{22}$ is hydrogen or $C_{1-4}$alkyl;
wherein $R^{11}$ may be optionally substituted on carbon by one or more $R^{13}$;
$R^{13}$ is selected from nitro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$— or piperidinyl-$X^9$—, wherein $X^8$, $X^9$ and $X^{10}$ each represent a direct bond;
and wherein $R^{13}$ may be optionally substituted on carbon by one or more $R^{18}$,
and wherein if said heterocyclyl or heteroaryl contains an —NH— moiety that nitrogen may be optionally substituted by a group selected from $R^{19}$;
$R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino, N,N—($C_{1-4}$alkyl)$_2$amino, $C_{1-4}$alkylS(O)$_a$ wherein a is 0 to 2, N—($C_{1-4}$alkyl)carbamoyl, N,N—($C_{1-4}$alkyl)$_2$carbamoyl, piperazinyl-, pyrrolidinyl-, piperidinyl- and morpholinyl-, and
$R^{19}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

In particular, in the compounds of formula IC, ID, IE and/or IF, $R^{10}$ is H and $R^{11}$ is selected from H and $C_{1-6}$alkyl, wherein $R^1$ is optionally substituted on carbon by one or more $R^{13}$ wherein $R^{13}$ is selected from carboxy, carbamoyl, N—($C_{1-6}$alkyl)carbamoyl, $C_{1-6}$alkoxycarbonyl and carbocyclyl-$X^8$— (such as phenyl-$X^8$—), wherein $X^8$ represents a direct bond and wherein $R^{13}$ is optionally substituted on carbon by N,N—($C_{1-6}$alkyl)$_2$amino.

In one aspect of the compounds of formula IC, ID, IE, IF, IC*, ID*, IE* and/or IF*, $R^6$ has any of the values defined hereinbefore, for example as defined in any of (62) to (74) above.

In one aspect of the compounds of formula IC, ID, IE, IF, IC*, ID*, IE* and/or IF*, $R^6$ is selected from H, $C_{1-6}$alkyl and $C_{2-6}$alkynyl (particularly H and $C_{1-6}$alkyl),
and wherein $R^6$ may be optionally substituted on carbon by one or more $R^{16}$; and wherein if said heterocyclyl or heteroaryl contains an —NH— moiety that nitrogen may be optionally substituted by a group selected from $R^{17}$;
wherein $R^{16}$ is selected from fluoro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$—, piperidinyl-$X^9$— and morpholinyl-$X^9$—, wherein $X^8$, $X^9$ and $X^{10}$ each represent a direct bond; and wherein $R^{16}$ is optionally substituted with one or more $R^{18}$;
wherein $R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino and N,N—($C_{1-4}$alkyl)$_2$amino; and
wherein $R^{17}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

In another aspect of the compounds of formula IC, ID, IE, IF, IC*, ID*, IE* and/or IF*, $R^6$ is selected from H, $C_{1-6}$alkyl, $C_{3-7}$cycloalkyl-$X^5$—, phenyl-$X^5$—, heterocyclyl-$X^6$— and heteroaryl-$X^7$— wherein said heterocyclyl is a monocyclic 5 or 6-membered heterocyclyl ring containing 1, 2 or 3 (suitably 1 or 2) heteroatoms selected from O, S and N, and wherein said heteroaryl is a monocyclic 5, 6 or 7-membered heteroaryl ring containing 1, 2 or 3 heteroatoms selected from O, S and N, and wherein $X^5$, $X^6$ and $X^7$ are each independently selected from a direct bond or —N($R^{12}$)C(O)—, wherein $R^{12}$ is hydrogen or $C_{1-4}$alky, and wherein $R^6$ may be optionally substituted on carbon by one or more $R^{16}$; and wherein if said heterocyclyl or heteroaryl contains an —NH— moiety that nitrogen may be optionally substituted by a group selected from $R^{17}$;

wherein $R^{16}$ is selected from fluoro, cyano, hydroxy, trifluoromethoxy, amino, carboxy, carboxyamino, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{3-7}$cycloalkyl-$X^8$—, phenyl-$X^8$—, pyridinyl-$X^{10}$—, pyrimidinyl-$X^{10}$—, thiazolyl-$X^{10}$—, imidazolyl-$X^{10}$—, pyrazolyl-$X^{10}$—, piperazinyl-$X^9$—, pyrrolidinyl-$X^9$—, piperidinyl-$X^9$— and morpholinyl-$X^9$—, wherein $X^8$, $X^9$ and $X^{10}$ each represent a direct bond;

and wherein $R^{16}$ is optionally substituted with one or more $R^{18}$;

wherein $R^{18}$ is selected from halo, hydroxy, amino, trifluoromethoxy, $C_{1-4}$alkyl (which $C_{1-4}$alkyl is optionally substituted by fluoro), $C_{1-4}$alkoxy, N—($C_{1-4}$alkyl)amino and N,N—($C_{1-4}$alkyl)$_2$amino; and $R^{17}$ is selected from $C_{1-4}$alkyl, $C_{1-4}$alkanoyl, $C_{1-4}$alkylsulfonyl, N—($C_{1-4}$alkyl)carbamoyl and N,N—($C_{1-4}$alkyl)$_2$carbamoyl.

In particular, in the compounds of formula IC, ID, IE, IF, IC*, ID*, IE* and/or IF*, $R^6$ is selected from H and $C_{1-6}$alkyl, wherein $R^6$ is optionally substituted on carbon by one or more $R^{16}$, wherein $R^{16}$ is selected from fluoro, $C_{1-6}$alkoxy, N,N—($C_{1-6}$alkyl)$_2$amino, carbocyclyl-$X^8$—, heterocyclyl-$X^9$— or heteroaryl-$X^{10}$—, wherein $X^8$, $X^9$ and $X^{10}$ each represents a direct bond and wherein any heterocyclyl group within $R^{16}$ optionally bears 1 or 2 oxo substituents.

In another aspect of the compounds of formula IC, ID, IE, IF, IC*, ID*, IE* and/or IF*, $R^6$ has any of the values defined hereinbefore, for example as defined in any of (62) to (74) above; and $R^{11}$ is selected from H and $C_{1-4}$alkyl, wherein $R^1$ is optionally substituted on carbon by one or more $R^{13}$ selected from halo, nitro, cyano, hydroxy, trifluoromethoxy, amino, carboxy, carboxyamino, carbamoyl, mercapto, sulfamoyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, $C_{1-4}$alkylsulfonylamino, phenyl, pyridyl and pyrimidinyl (particularly $R^{11}$ is selected from H and $C_{1-4}$alkyl).

In another embodiment of the invention there is provided a compound of the formula I selected from:

(7S)-2-amino-8-[(4-methoxy-3,5-dimethylpyridin-2-yl)methyl]-7-methyl-7,8-dihydropteridin-6(5H)-one;
(7S)-2-amino-8-[(4-methoxy-3,5-dimethylpyridin-2-yl)methyl]-7-propyl-7,8-dihydropteridin-6(5H)-one;
(7R)-2-amino-8-[(4-methoxy-3,5-dimethylpyridin-2-yl)methyl]-7-methyl-7,8-dihydropteridin-6(5H)-one;
2-amino-8-[(4-methoxy-3,5-dimethylpyridin-2-yl)methyl]-7,8-dihydropteridin-6(5H)-one;
(7S)-8-[(4-methoxy-3,5-dimethylpyridin-2-yl)methyl]-7-methyl-5,6,7,8-tetrahydropteridin-2-amine;
(7S)-2-amino-8-[(4-methoxy-3,5-dimethylpyridin-2-yl)methyl]-5,7-dimethyl-7,8-dihydropteridin-6(5H)-one;
(7S)-2-amino-5-ethyl-8-[(4-methoxy-3,5-dimethylpyridin-2-yl)methyl]-7-methyl-7,8-dihydropteridin-6(5H)-one;
(7R)-2-amino-8-[(4-methoxy-3,5-dimethylpyridin-2-yl)methyl]-5,7-dimethyl-7,8-dihydropteridin-6(5H)-one;
2-amino-8-[(4-methoxy-3,5-dimethylpyridin-2-yl)methyl]-5-methyl-7,8-dihydropteridin-6(5H)-one;
(7S)-8-[(4-methoxy-3,5-dimethylpyridin-2-yl)methyl]-5,7-dimethyl-7,8-tetrahydropteridin-2-amine;
(7R)-8-[(4-methoxy-3,5-dimethylpyridin-2-yl)methyl]-7-methyl-5,6,7,8-tetrahydropteridin-2-amine; and
(7R)-8-[(4-methoxy-3,5-dimethylpyridin-2-yl)methyl]-5,7-dimethyl-5,6,7,8-tetrahydropteridin-2-amine;

or a pharmaceutically acceptable salt thereof.

In another embodiment of the invention there is provided a compound of the formula I selected from:

(7S)-2-amino-8-[(4-methoxy-3,5-dimethylpyridin-2-yl)methyl]-7-methyl-7,8-dihydropteridin-6(5H)-one;
(7S)-2-amino-8-[(4-methoxy-3,5-dimethylpyridin-2-yl)methyl]-7-propyl-7,8-dihydropteridin-6(5H)-one;
(7R)-2-amino-8-[(4-methoxy-3,5-dimethylpyridin-2-yl)methyl]-7-methyl-7,8-dihydropteridin-6(5H)-one;
2-amino-8-[(4-methoxy-3,5-dimethylpyridin-2-yl)methyl]-7,8-dihydropteridin-6(5H)-one;
(7S)-2-amino-8-[(4-methoxy-3,5-dimethylpyridin-2-yl)methyl]-5,7-dimethyl-7,8-dihydropteridin-6(5H)-one;
(7S)-2-amino-5-ethyl-8-[(4-methoxy-3,5-dimethylpyridin-2-yl)methyl]-7-methyl-7,8-dihydropteridin-6(5H)-one;
(7R)-2-amino-8-[(4-methoxy-3,5-dimethylpyridin-2-yl)methyl]-5,7-dimethyl-7,8-dihydropteridin-6(5H)-one;
2-amino-8-[(4-methoxy-3,5-dimethylpyridin-2-yl)methyl]-5-methyl-7,8-dihydropteridin-6(5H)-one;
(7S)-8-[(4-methoxy-3,5-dimethylpyridin-2-yl)methyl]-7-methyl-5,6,7,8-tetrahydropteridin-2-amine;
(7S)-8-[(4-methoxy-3,5-dimethylpyridin-2-yl)methyl]-5,7-dimethyl-5,6,7,8-tetrahydropteridin-2-amine;
(7R)-8-[(4-methoxy-3,5-dimethylpyridin-2-yl)methyl]-7-methyl-5,6,7,8-tetrahydropteridin-2-amine;
(7R)-8-[(4-methoxy-3,5-dimethylpyridin-2-yl)methyl]-5,7-dimethyl-5,6,7,8-tetrahydropteridin-2-amine;
8-[(4-methoxy-3,5-dimethylpyridin-2-yl)methyl]-5-methyl-5,6,7,8-tetrahydropteridin-2-amine;
(7R)-2-amino-8-[(4-methoxy-3,5-dimethyl-pyridin-2-yl)methyl]-7-(2-methylpropyl)-7,8-dihydropteridin-6(5H)-one;
(7R)-2-amino-7-benzyl-8-[(4-methoxy-3,5-dimethyl-pyridin-2-yl)methyl]-7,8-dihydropteridin-6(5H)-one;
methyl {(7R)-2-amino-8-[(4-methoxy-3,5-dimethylpyridin-2-yl)methyl]-6-oxo-5,6,7,8-tetrahydropteridin-7-yl}acetate;
(7R)-2-amino-8-[(4-methoxy-3,5-dimethyl-pyridin-2-yl)methyl]-7-propyl-7,8-dihydropteridin-6(5H)-one;
2-amino-4-chloro-8-[(4-methoxy-3,5-dimethyl-pyridin-2-yl)methyl]-5,7-dihydropteridin-6-one;
2-amino-8-[(4-methoxy-3,5-dimethyl-pyridin-2-yl)methyl]-4-methylsulfanyl-5,7-dihydropteridin-6-one;
(7R)-2-amino-8-[(4-methoxy-3,5-dimethylpyridin-2-yl)methyl]-5-(3-methoxypropyl)-7-methyl-7,8-dihydropteridin-6(5H)-one;
2-amino-8-[(4-methoxy-3,5-dimethylpyridin-2-yl)methyl]-5-(3-methoxypropyl)-7,8-dihydropteridin-6(5H)-one;
(7R)-2-amino-8-[(4-methoxy-3,5-dimethylpyridin-2-yl)methyl]-7-methyl-5-(2-phenylethyl)-7,8-dihydropteridin-6(5H)-one;
(7R)-2-amino-8-[(4-methoxy-3,5-dimethylpyridin-2-yl)methyl]-7-methyl-5-(2-piperazin-1-ylethyl)-7,8-dihydropteridin-6(5H)-one;

(7R)-2-amino-5-(2,2-difluoroethyl)-8-[(4-methoxy-3,5-dimethylpyridin-2-yl)methyl]-7-methyl-7,8-dihydropteridin-6(5H)-one;

2-amino-8-[(4-methoxy-3,5-dimethylpyridin-2-yl)methyl]-5-(3-methylbutyl)-7,8-dihydropteridin-6(5H)-one;

2-amino-4-chloro-8-[(4-methoxy-3,5-dimethylpyridin-2-yl)methyl]-5-(3-methylbutyl)-7,8-dihydropteridin-6(5H)-one;

(7R)-2-amino-8-[(4-methoxy-3,5-dimethylpyridin-2-yl)methyl]-7-methyl-5-(3-methylbutyl)-7,8-dihydropteridin-6(5H)-one;

(7R)-2-amino-8-[(4-methoxy-3,5-dimethylpyridin-2-yl)methyl]-7-methyl-5-propyl-7,8-dihydropteridin-6(5H)-one;

(7R)-2-amino-5-benzyl-8-[(4-methoxy-3,5-dimethylpyridin-2-yl)methyl]-7-methyl-7,8-dihydropteridin-6(5H)-one;

(7R)-2-amino-5-(cyclopropylmethyl)-8-[(4-methoxy-3,5-dimethylpyridin-2-yl)methyl]-7-methyl-7,8-dihydropteridin-6(5H)-one;

(7R)-2-amino-8-[(4-methoxy-3,5-dimethylpyridin-2-yl)methyl]-7-methyl-5-(2-pyrrolidin-1-ylethyl)-7,8-dihydropteridin-6(5H)-one;

(7R)-2-amino-5-[2-(dimethylamino)-2-methylpropyl]-8-[(4-methoxy-3,5-dimethylpyridin-2-yl)methyl]-7-methyl-7,8-dihydropteridin-6(5H)-one;

(7R)-2-amino-5-[3-(dimethylamino)propyl]-8-[(4-methoxy-3,5-dimethylpyridin-2-yl)methyl]-7-methyl-7,8-dihydropteridin-6(5H)-one;

(7R)-2-amino-8-[(4-methoxy-3,5-dimethylpyridin-2-yl)methyl]-7-methyl-5-(2-morpholin-4-ylethyl)-7,8-dihydropteridin-6(5H)-one;

(7R)-2-amino-8-[(4-methoxy-3,5-dimethylpyridin-2-yl)methyl]-7-methyl-5-(2-pyridin-4-ylethyl)-7,8-dihydropteridin-6(5H)-one;

(7R)-2-amino-8-[(4-methoxy-3,5-dimethylpyridin-2-yl)methyl]-7-methyl-5-(2-pyridin-3-ylethyl)-7,8-dihydropteridin-6(5H)-one;

(7R)-2-amino-8-[(4-methoxy-3,5-dimethylpyridin-2-yl)methyl]-7-methyl-5-(3-pyridin-3-ylpropyl)-7,8-dihydropteridin-6(5H)-one;

2-amino-4-chloro-8-[(4-methoxy-3,5-dimethylpyridin-2-yl)methyl]-5-(2-pyridin-3-ylethyl)-7,8-dihydropteridin-6(5H)-one;

2-amino-8-[(4-methoxy-3,5-dimethylpyridin-2-yl)methyl]-5-propyl-7,8-dihydropteridin-6(5H)-one;

(7R)-2-amino-8-[(4-methoxy-3,5-dimethylpyridin-2-yl)methyl]-7-methyl-5-[2-(2-oxoimidazolidin-1-yl)ethyl]-7,8-dihydropteridin-6(5H)-one;

(7R)-2-amino-8-[(4-methoxy-3,5-dimethylpyridin-2-yl)methyl]-7-methyl-5-[2-(2-oxopyrrolidin-1-yl)ethyl]-7,8-dihydropteridin-6(5H)-one;

2-amino-5-benzyl-4-chloro-8-[(4-methoxy-3,5-dimethylpyridin-2-yl)methyl]-7,8-dihydropteridin-6(5H)-one;

2-amino-4-chloro-8-[(4-methoxy-3,5-dimethylpyridin-2-yl)methyl]-5-propyl-7,8-dihydropteridin-6(5H)-one;

2-amino-4-chloro-8-[(4-methoxy-3,5-dimethylpyridin-2-yl)methyl]-5-(2-phenylethyl)-7,8-dihydropteridin-6(5H)-one;

{(7R)-2-amino-8-[(4-methoxy-3,5-dimethylpyridin-2-yl)methyl]-6-oxo-5,6,7,8-tetrahydropteridin-7-yl}acetic acid;

2-{(7R)-2-amino-8-[(4-methoxy-3,5-dimethylpyridin-2-yl)methyl]-6-oxo-5,6,7,8-tetrahydropteridin-7-yl}acetamide;

2-{(7R)-2-amino-8-[(4-methoxy-3,5-dimethylpyridin-2-yl)methyl]-6-oxo-5,6,7,8-tetrahydropteridin-7-yl}-N-[3-(dimethylamino)propyl]acetamide;

2-{(7R)-2-amino-8-[(4-methoxy-3,5-dimethylpyridin-2-yl)methyl]-6-oxo-5,6,7,8-tetrahydropteridin-7-yl}-N-[2-(dimethylamino)ethyl]acetamide;

2-amino-8-[(4-methoxy-3,5-dimethyl-pyridin-2-yl)methyl]-4-methyl-5,7-dihydropteridin-6-one;

or an N-oxide thereof;

or a pharmaceutically acceptable salt thereof.

Synthesis

The compounds of the present invention can be prepared in a number of ways using methods analogous to well known methods of organic synthesis. More specifically, the novel compounds of this invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, are chosen to be the conditions standard for that reaction. It is understood by one skilled in the art of organic synthesis that the functionality present on various portions of the molecule must be compatible with the reagents and reactions proposed. Such restrictions to the substituents, which are not compatible with the reaction conditions, will be apparent to one skilled in the art and alternate methods must then be used.

It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley Interscience (1991). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

Compounds of the formula I, or pharmaceutically-acceptable salts or prodrugs thereof, may be prepared by any process known to be applicable to the preparation of chemically-related compounds and intermediates, for example as described in WO 04/076454, WO 03/020722, WO 04/076454 and WO 03/020722. Such processes, when used to prepare a compound of the formula I, or a pharmaceutically-acceptable salt or prodrug thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist.

The present invention also provides that compounds of the formula I, or pharmaceutically acceptable salts or prodrugs thereof, can be prepared by a process (a) to (g) as follows (wherein the variables are as defined above unless otherwise stated):

Process (a):

For the preparation of compounds of the formula I wherein A is $CR^{10}R^{11}$ and $R^4$ and $R^5$ together form oxo, the reduction and cyclisation in the presence of a suitable reducing agent of the compound of the formula II:

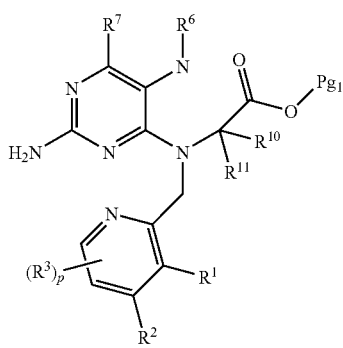

II wherein $R^1$, $R^2$, $R^3$, $R^7$, $R^{10}$, $R^{11}$ and p are as hereinbefore defined, except any functional group is protected if necessary; and $Pg_1$ is a suitable carboxy protecting group; or Process (b)

for the preparation of those compounds of the formula I wherein $R^6$ is optionally substituted $C_{1-6}$alkyl, $C_{2-6}$alkenyl, $C_{2-6}$alkynyl, heterocyclyl, carbocyclyl or heteroaryl, the coupling of a compound of the formula I wherein $R^6$ is H, with an alcohol of the formula $R^6$—OH; or Process (c)

for the preparation of those compounds of the formula I wherein $R^4$ and $R^5$ are both hydrogen, the reduction of a compound of the formula I of the formula I':

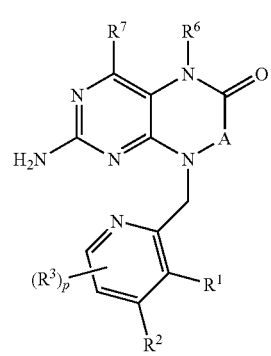

I' wherein $R^1$, $R^2$, $R^3$, $R^6$, $R^7$, A and p are as hereinbefore defined, except any functional group is protected if necessary; or Process (d)

for the preparation of those compounds of the formula I wherein A in the compound of formula I is $CHR^{11}$ and $R^{11}$ is optionally substituted $C_{1-6}$alkyl, $C_{2-6}$alkenyl, $C_{2-6}$alkynyl, $C_{3-7}$cycloalkyl, or an optionally substituted carbon-linked heterocyclyl, the deprotonation and alkylation of a compound of the formula I" with a compound of the formula III:

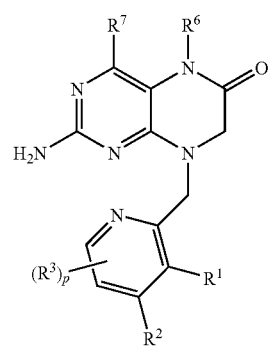

I"

$R^{11}$—$Lg^3$

III wherein $R^1$, $R^2$, $R^3$, $R^6$, $R^7$, $R^{11}$ and p are as hereinbefore defined, except any functional group is protected if necessary and $Lg^3$ is a displaceable group; or Process (e)

the amination of a compound of the formula IV:

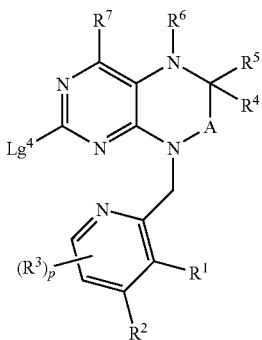

IV wherein $R^1$, $R^2$, $R^3$, $R^4$, $R^5$, $R^6$, $R^7$, A and p are as hereinbefore defined, except any functional group is protected if necessary and $Lg^4$ is a displaceable group; or Process (f)

for the preparation of those compounds of the formula I wherein A in the compound of formula I is $CHR^{11}$ and $R^{11}$ is a $C_{1-6}$alkyl group substituted by a carboxy group, the hydrolysis of a compound of the formula I''':

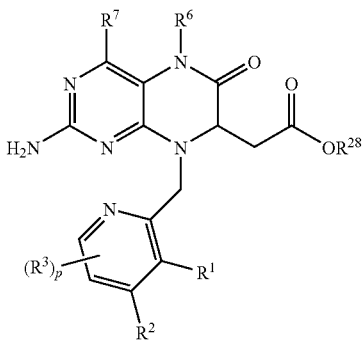

I''' wherein $R^1$, $R^2$, $R^3$, $R^6$, $R^7$ and p are as hereinbefore defined, except any functional group is protected if necessary and $R^{28}$ is a $C_{1-6}$alkyl group; or Process (g)

for the preparation of those compounds of the formula I wherein A in the compound of formula I is $CHR^{11}$ and $R^{11}$ is a $C_{1-6}$alkyl group substituted by a carbamoyl, N—($C_{1-6}$alkyl)carbamoyl or N,N—($C_{1-6}$alkyl)$_2$carbamoyl group, the coupling of a compound of the formula I'''' (or a suitable salt thereof) with ammonia or a N—($C_{1-6}$alkyl)amino or N,N—($C_{1-6}$alkyl)$_2$amino group:

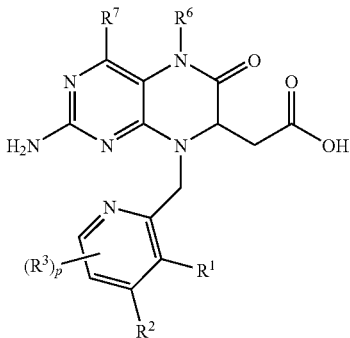

I'''' wherein $R^1$, $R^2$, $R^3$, $R^6$, $R^7$ and p are as hereinbefore defined, except any functional group is protected if necessary;

and thereafter, if necessary (in any order):
(i) converting a compound of the formula I into another compound of the formula I;
(ii) removing any protecting groups; and
(iii) forming a pharmaceutically acceptable salt of the compound of formula I.

Specific conditions for the above reactions are as follows.

Reaction Conditions for Process (a):

$Pg_1$ is a suitable carboxy protecting group such as $C_{1-6}$alkyl, for example methyl.

The reduction of the nitro group in the compound of formula II is conveniently carried out in the presence of a suitable reducing agent such as a transitions metal, for example iron in the presence of a suitable acid. Suitable acids include mineral acids such as hydrochloric acid or sulfuric acid or organic acids such as acetic acid or formic acid. Other suitable reducing agents that may be used under neutral pH conditions include zinc, samarium-di-iodide and trivalent titanium. Conveniently the reaction is carried out in the presence of an inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar solvent such as N,N-dimethylformamide, N,N-dimethylacetamide, N-methylpyrrolidin-2-one, dimethylsulfoxide or acetonitrile. The above reaction is conveniently carried out at a temperature in the range, for example, 0° C. to 180° C., conveniently in the range ambient temperature to 80° C. or preferably, at or near the reflux temperature of the solvent when used.

The above reaction conveniently gives the in-situ cyclisation of the resulting amino derivative of the compound of formula II, thereby providing the compound of formula I.

Preparation of Starting Materials for Process (a)

The compound of formula II may be prepared using conventional methods, for example as illustrated in Reaction Scheme 1:

Reaction Scheme 1

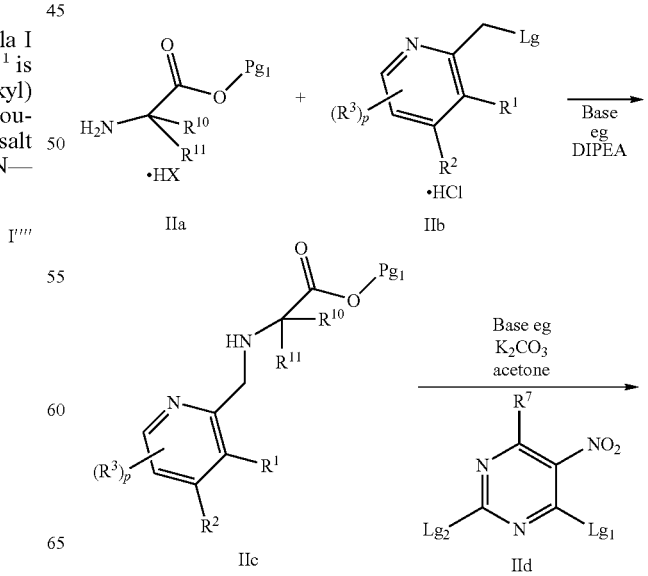

-continued

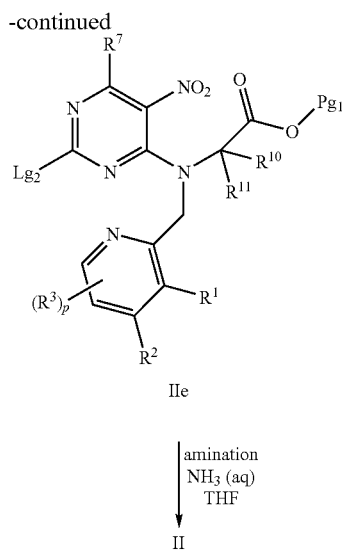

IIe

↓ amination
NH₃ (aq)
THF

II wherein $R^1$, $R^2$, $R^3$, $R^7$, $R^{10}$, $R^{11}$ and p are as hereinbefore defined, except any functional group is protected if necessary; $Pg_1$ is a suitable carboxy protecting group such as $C_{1-6}$alkyl (for example methyl) or benzyl; and Lg, $Lg^1$ and $Lg^2$ are suitable displaceable groups.

Lg is for example halo, such as chloro. Suitable displaceable groups represented by $Lg^1$ and $Lg^2$ include, for example halo (particularly chloro), aryloxy, mercapto, alkylthio, alkylsulfonyl, arylsulfonyl, alkylsulfonyloxy or arylsulfonyloxy methanesulfonyloxy or toluene-4-sulfonyloxy group. A particular displaceable group for $Lg^1$ and $Lg^2$ is chloro.

Suitable reaction conditions for Reaction Scheme 1 are well known for the preparation of similar compounds and are illustrated by the examples described herein.

The starting materials of the formulae IIa and IIb are commercially available or can be prepared using conventional methods.

Reaction Conditions for Process (b):

The coupling reaction is suitably carried out under Mitsunobu conditions as described in Hughes, D. L. et. al. Org. Prep. (1996), 28, 127-164. For example, the reaction is conveniently carried out in the presence of a suitable electrophilic activating agents, for example, diisopropyl azodicarboxylate (DIAD) or 1,1'-(azodicarbonly)dipiperidine (ADDP) or 4,7-dimethyl-3,5,7-hexahydro-1,2,4,7-tetrazocin-3,8-dione (DHTD) in combination with a nucleophilic activating agent such as for example phosphorous based activating agent such as for example tributylphosphine, triphenylphosphine, or cyanomethylenetributylphosphorane. The reaction is conveniently carried out in the presence of a suitable inert solvent or diluent, for example an ether such as tetrahydrofuran or an aromatic solvent such as for example benzene or toluene or an non polar solvent such as acetonitrile. The reaction is conveniently carried out at temperatures in a range, for example, from below room temperature to elevated temperatures such as boiling point of solvent, conveniently at or near ambient temperature.

The phosphine coupling reagent is optionally immobilised on a solid support.

Reaction Conditions for Process (c):

The reduction is carried out in the presence of a suitable reducing agent such as a borane-THF complex. The reaction is suitably carried out in a solvent such as an ether, for example tetrahydrofuran. The reaction is conveniently performed at elevated temperature, for example, under reflux conditions.

Reaction Conditions for Process (d)

Suitable displaceable groups represented by $Lg^3$ include for example halo such as bromo or iodo.

The deprotonation of the compound of formula I" may be achieved by formation of the alkali metal enolate of the compound of formula I" for example the lithium or potassium enolate.

The reaction is conveniently performed in the presence of a suitable base, for example, an alkali metal hydride such as sodium hydride, an alkali metal disalazide such as sodium hexamethyldisilazide or an organolithium reagent such as N-butyl-lithium or methyl-lithium.

The reaction is conveniently carried out in the presence of a suitable inert solvent or diluent, for example an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one, or dimethylsulfoxide.

The reaction is suitably carried out at a temperature of from $-80°$ C. to $30°$ C., conveniently at temperatures of $-78°$ C.

Suitable reaction conditions for the deprotonation and reaction with $R^{11}$-$Lg^3$ are known in the literature, for example as described in Bull et. al., Tetrahedron (2006), 62 (33), 7911-25; or Viso et. al., Journal of Organic Chemistry (2006), 71 (4), 1442-48.

Reaction Conditions for Process (e):

$Lg^4$ is a suitable displaceable group, for example, a halo (particularly chloro), aryloxy, mercapto, alkylthio, alkylsulfonyl, arylsulfonyl, alkylsulfonyloxy or arylsulfonyloxy or groups for example chloro, bromo, fluoro, methoxy, phenoxy, pentafluorophenoxy, methylthio, methanesulfonyl, methanesulfonyloxy or toluene-4-sulfonyloxy group. A particular displaceable group $Lg^4$ is chloro.

The reaction is conveniently carried out in the presence of base, acid or transition metal catalyst, particular conditions are the displacement of $Lg^4$ in the presence of base.

The amination reaction is conveniently performed in an inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar solvent such as N,N-dimethylformamide, N,N-dimethylacetamide, N-methylpyrrolidin-2-one, dimethylsulfoxide or acetonitrile. Particular solvents are ethers such as tetrahydrofuran or 1,4-dioxane.

The reaction is conveniently carried out at a temperature in the range, for example, $0°$ C. to $180°$ C., particularly in the range ambient temperature to $80°$ C. or more particularly, at or near the reflux temperature of the solvent when used.

Conveniently the amination reaction is carried out with ammonia, or a latent form of ammonia such a benzylamine or hydrazine derivative. Conveniently amination may be carried out using a latent source of ammonia in the presence of a suitable transition metal catalyst. For example benzophenonimine might be used as a latent source of ammonia in the presence of a palladium catalyst. If latent sources of ammonia are used, the amino group is liberated after the displacement reaction, for example with acids such as trifluorosulfonic acid, hydrochloric acid or sulfuric acid. It will be appreciated by those skilled in the art that in the liberation of latent amino functionalities might require the utility of aqueous acid. Suitable aqueous acids include, for example hydrochloric acid, or and organic acid such as acetic acid a buffer may also be used to maintain pH at the desired level during the reaction. Particularly, the amination uses of ammonia, which may be conveniently dissolved in a suitable solvent such as for water or methanol.

Reaction Conditions for Process (f):

The hydrolysis reaction is conveniently carried out in the presence of a suitable aqueous base or suitable aqueous acid. Suitable aqueous bases include aqueous sodium hydroxide and potassium hydroxide. Suitable aqueous acids include aqueous sulphuric acid.

Conveniently the hydrolysis reaction is carried out in the presence of an inert solvent or diluent, for example water, an ester or an ether such as tetrahydrofuran or 1,4-dioxan. For example, a suitable solvent may be a mixture of water and tetrahydrofuran. The reaction is conveniently carried out at a temperature in the range, for example, 0° C. to 100° C., conveniently at ambient temperature.

Reaction Conditions for Process (g):

For the coupling of the compound of formula I''' with a N—($C_{1-6}$alkyl)amino or N,N—($C_{1-6}$alkyl)$_2$amino group, the reaction is conveniently conducted using analogous conditions to those defined above for Process (b).

For the coupling of the compound of formula I''' with ammonia, the reaction is conveniently carried out in the presence of a suitable coupling agent. A suitable coupling agent is, for example, a suitable peptide coupling agent, such as O-(7-azabenzotriazol-1-yl)-N,N,N',N'-tetramethyluronium hexafluoro-phosphate (HATU) or a carbodiimide such as dicyclohexylcarbodiimide or 1-(3-dimethylaminopropyl)-3-ethylcarbodiimide hydrochloride (EDCI). The reaction may conveniently be carried out in the presence of a suitable base. A suitable base is, for example, an organic amine base such as pyridine, 2,6-lutidine, collidine, 4-dimethylaminopyridine, triethylamine, di-isopropylethylamine, N-methylmorpholine or diazabicyclo[5.4.0]undec-7-ene, or an alkali or alkaline earth metal carbonate, such as sodium carbonate, potassium carbonate, caesium carbonate or calcium carbonate.

The reaction is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, an alcohol such as methanol or ethanol, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., particularly at or near ambient temperature. Conveniently, this reaction may also be performed by heating the reactants in a sealed vessel using a suitable heating apparatus such as a microwave heater.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

When a pharmaceutically acceptable salt of a compound of the formula I is required, for example an acid or base addition salt, it may be obtained by, for example, reaction of the compound of formula I with a suitable acid or base using a conventional procedure. Methods for the preparation of pharmaceutically acceptable salts are well known in the art. For example, following reaction of a compound of the formula I with an acid or base the required salt may be precipitated from solution by supersaturating the solution containing the compound of the formula I. Super saturation may be achieved using well-known techniques, for example by cooling the solution, by removing solvent by evaporation or by the addition of a suitable anti-solvent to precipitate the salt.

To facilitate isolation of a compound of the formula I during its preparation, the compound may be prepared in the form of a salt that is not a pharmaceutically acceptable salt. The resulting salt can then be modified by conventional techniques to give a pharmaceutically acceptable salt of the compound. Such salt modification techniques are well known and include, for example ion exchange techniques or re-precipitation of the compound from solution in the presence of a pharmaceutically acceptable counter ion as described above, for example by re-precipitation in the presence of a suitable pharmaceutically acceptable acid to give the required pharmaceutically acceptable acid addition salt of a compound of the formula I.

Stereoisomers of compounds of formula I may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free from other stereoisomers, for example containing less than 20%, particularly less than 10% and more particularly less than 5% by weight of other stereoisomers.

In the synthesis section above and hereafter, the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

Biological Activity

The following assays can be used to measure the effects of the compounds of the present invention as HSP90 inhibitors.

Test (a) In Vitro Binding Assay

Test (a) measures the ability of a compound to bind to the ATP pocket of HSP90α. 6H is tagged HSP90α protein (amino acids 2-732) expressed in *E. coli* was purified and stored at −80° C. in aliquots. Assay measurements were performed in assay buffer comprising 20 mM HEPES pH 7.4, 50 mM KCl, 20 mM NaHMoO$_4$, 0.01% Nonidet P40, 2 mM DTT and 0.1 mg/ml BSA. Following resuspension in DMSO, the FP probe 3-[[5-(5-ethyl-2,4-dihydroxy-phenyl)-4-(4-methoxyphenyl)2H-pyrazole-3-carbonyl]amino]propyl-Cy3B-amide; 14-(2-{[3-({[3-(5-ethyl-2,4-dihydroxyphenyl)-4-(4-methoxyphenyl)-1H-pyrazol-5-yl]carbonyl}amino)propyl]amino}-2-oxoethyl)-16,16,18,18-tetramethyl-2-sulfo-6,7,7a,8a,9,10,16,18-octahydrobenzo[2",3"]indolizino [8",7":5',6']pyrano[3',2':3,4]pyrido[1,2-a]indol-5-ium) was diluted to a final concentration of 5 nM in assay buffer. Test compounds were prepared by dilution in 100% DMSO to give the appropriate dose range and dispensed into a 384 well assay plate as a 6X concentrate. Upon addition of recombinant HSP90α to a final assay concentration of 1 μg/ml, FP probe was added and plates incubated at room temperature for 1 to 4 hours. Final DMSO concentration was 1% in a total assay volume of 18 μl. Fluorescence Polarisation measurements were made using a Tecan Ultra plate reader using an excitation wavelength of 530 nm and an emission wavelength of 590 nm. Millipolarisation (mP) values were estimated using Xfluor software.

Assay Probe

The 3-[[5-(5-ethyl-2,4-dihydroxy-phenyl)-4-(4-methoxyphenyl)2H-pyrazole-3-carbonyl]amino]propyl-Cy3B-amide; 14-(2-{[3-({[3-(5-ethyl-2,4-dihydroxyphenyl)-4-(4-methoxyphenyl)-1H-pyrazol-5-yl]carbonyl}amino)propyl]amino}-2-oxoethyl)-16,16,18,18-tetramethyl-2-sulfo-6,7,7a,8a,9,10,16,18-octahydrobenzo[2",3"]indolizino [8",7":5',6']pyrano[3',2':3,4]pyrido[1,2-a]indol-5-ium used as the assay probe in Test (a) was prepared as follows:

Assay Probe

A cold solution (0° C.) of pyrano[3",2":3,4;5",6":3',4']dipyrido[1,2-a:1',2'-a']diindol-5-ium, 2-[2-[(2,5-dioxo-1-pyrrolidinyl)oxy]-2-oxoethyl]-6,7,9,10,16,18-hexahydro-16,16,18,18-tetramethyl-14-sulfo-, inner salt [(9CI) CAS No: 228272-52-4 (also known as Cy 3B NHS Ester)] (5 mg) in 1 ml dry DMF was added to a solution of N-(3-aminopropyl)-5-(5-ethyl-2,4-dihydroxy-phenyl)-4-(4-methoxyphenyl)-2H-pyrazole-3-carboxamide (4 mgs) and dry N,N-diisopropylethylamine (7 μL) in 2 ml of dry DMF. The reaction mixture was stirred at 0° C. for 1 hour before then warmed up slowly to room temperature. The reaction mixture was then stirred for an additional 14 hours at room temperature.

The product was isolated directly from the reaction mixture without prior workup by reverse phase HPLC. The fractions containing the desired product were combined and evaporated under reduced pressure at a temperature not exceeding 30° C. Purification Conditions: Waters XTerra® C18 50×10 mm HPLC Column, 5 micron particle size, flow rate 3.5 ml/min, gradient 30%-55% B 10 minutes (A=10% NH$_3$/H$_2$O; B=100% CH$_3$CN).

Mass Spectrum: (M+H$^+$) 953 Retention time 1.89 minutes. (For alternative conditions see Moulick et. al. Bioorganic & Medicinal Chemistry Letters (2006), 16, 4515-18).

The N-(3-aminopropyl)-5-(5-ethyl-2,4-dihydroxy-phenyl)-4-(4-methoxyphenyl)-2H-pyrazole-3-carboxamide starting material was prepared as follows:

Preparation of 1-(5-ethyl-2,4-dihydroxy-phenyl)-2-(4-methoxyphenyl)ethanone

4-Ethylbenzene-1,3-diol (17.5 g, 159 mmol) and 4-methoxyphenylacetic acid (26.4 g, 159 mmol) was heated with boron trifluoride dietherate solution (100.7 ml, 795 mmol) to 90° C. for 3 hours. The mixture was then cooled to 50° C. before it was added to a stirred solution of 10% aqueous sodium acetate (11). The resulting mixture was stirred at room temperature over night at room temperature. The resulting solid was filtered off dissolved in a minimum volume of methanol and pre-absorbed onto silica gel. For the initial purification the crude material was chromatographed, eluting with an increasingly polar mixture of methylene chloride/methanol (95/5 to 90/10). The fractions containing product were grouped into two groups, evaporated under vacuum to give a solid which was triturated with diethyl ether in a further purification step. The title compound was obtained in three

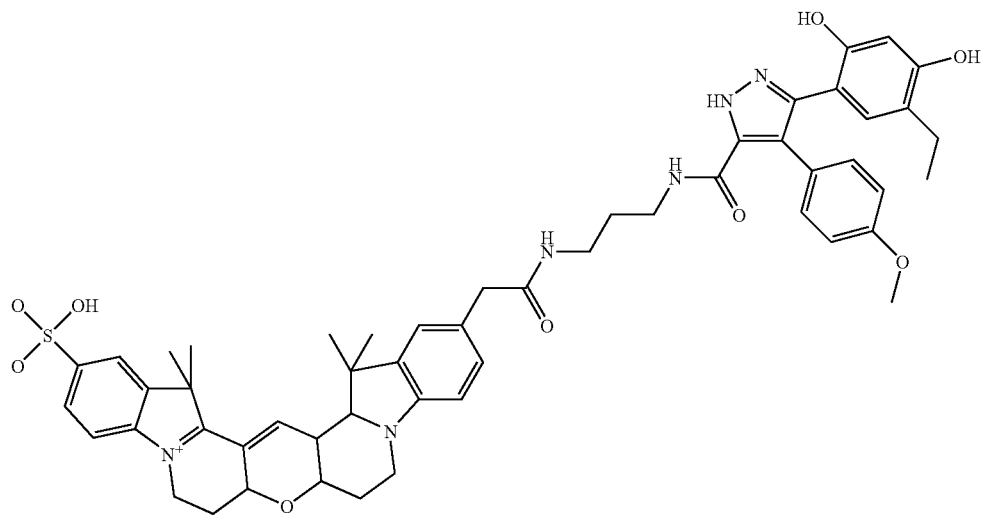

portions of varying purity as an off white solid from combined purest fractions (10.78 g, 26.2%) the less pure fractions (7.56 g, 18.4%) and from the combined, evaporated mother liquors after renewed trituration with iso-hexane/diethylether to give the title product (6.32 g, 15.4%). $^1$H NMR Spectrum (purest solid): δH (300 MHz, CDCl$_3$) 1.22 (3H t, J=7.5 Hz), 1.63 (1H, s), 2.57 (2H q, J=7.5 Hz), 3.79 (3H, s), 4.16 (2H d, J=3.0 Hz), 5.52 (1H, s), 6.30 (1H, s), 6.85-6.90 (2H, m), 7.16-7.21 (2H, m), 7.59 (1H, s), 12.51 (1H, s); Mass Spectrum: (M+H$^-$) 258.20.

Preparation of Methyl 6-ethyl-7-hydroxy-3-(4-methoxyphenyl)-4-oxo-chromene-2-carboxylate 1-(2,4-Dihydroxyphenyl)-2-(4-hydroxyphenyl)ethanone (18.16 g, 63.42 mmol) was dissolved in anhydrous pyridine (100 ml). The solution was cooled to 0° C. in an ice bath. Then methyl chlorooxacetate (17.5 ml, 190.27 mmol) was added drop wise over a period of 15 minutes to the vigorously stirred solution. A precipitate formed immediately. The resulting suspension was stirred at 0° C. for a further 4 hours before it was place in a refrigerator over night. Then the reaction mixture was warmed to room temperature before all volatile components were removed in vacuum. The residue was suspended with DCM and washed with 1N aqueous hydrochloric acid solution, brine. The organic phase was dried over magnesium sulfate and evaporated to dryness. LC/MS analysis indicted that the condensation reaction had only completed partially. To complete the condensation reaction the crude material was dissolved in methanol (400 ml) and 2N hydrochloric acid was added (100 ml) and subsequently heated to reflux for 2 hours. Then the reaction mixture was filtered whilst hot to give the title product as a white solid (13.6 g) which was used without further purification. Mass Spectrum: (M+H$^+$) 355.28, (M+H$^-$) 353.08.

Preparation of 6-ethyl-7-hydroxy-3-(4-methoxyphenyl)-4-oxo-chromene-2-carboxylic acid Methyl 6-ethyl-7-hydroxy-3-(4-methoxyphenyl)-4-oxo-chromene-2-carboxylate (13.6 g, 41.73 mmol) was dissolved in acetone (200 ml). Then a 2N aqueous solution of Sodium hydroxide (62.59 ml, 125.19 mmol) was added at room temperature. The resulting mixture was stirred at room temperature over night. After the reaction was complete the mixture was acidified under cooling with concentrated hydrochloric acid to pH 2.5. A solid precipitated from the solution. The solid was filtered off, washed with water and diethyl ether and dried at 40° C. under vacuum to yield the title product as an off white solid (11.2 g quantitative). The material was used directly without further purification in the next step. Mass Spectrum: (M+H$^+$) 341.25, (M+H$^-$) 339.19.

Preparation of 5-(5-ethyl-2,4-dihydroxy-phenyl)-4-(4-methoxyphenyl)-2H-pyrazole-3-carboxylic acid 6-Ethyl-7-hydroxy-3-(4-methoxyphenyl)-4-oxo-chromene-2-carboxylic acid (13.6 g, 41.73 mmol) and hydrazine monohydrate (6.1 ml, 125.19 mmol) were suspended in ethanol (200 ml) at room temperature. The mixture was then heated slowly to 70° C. and stirred at this temperature for 4 hours. The mixture was cooled to room temperature and all volatile components were removed in vacuum. The residue was partitioned between water (1l) and Ethyl acetate (1.4l). Then the aqueous phase was separated. The organic phase yielded some product. The remainder of the product was extracted from the aqueous phase with Ethyl acetate (4×500 ml). The combined organic extracts were dried over Magnesium sulfate and evaporated to dryness under vacuum resulting in a further quantity of the desired product. The combined isolated product portions yielded 6.99 g (51%) of a light brown solid. $^1$H NMR Spectrum: δH (400 MHz, DMSO-$^6$d) 0.84 (3H t, J=7.5 Hz), 2.23 (2H q, J=7.5 Hz), 3.38 (1H s, br), 3.74 (3H, s), 6.36 (1H, s), 6.56 (1H, s), 6.85 (2H d, J=8.7 Hz), 7.13 (2H d, J=8.7 Hz), 9.3 (1H s, br), 9.4 (1H s, br), 12.8 (1H s, br); Mass Spectrum: (M+H$^+$) 355.04, (M+H$^-$) 353.09.

Preparation of tert-butyl N-[3-[[5-(5-ethyl-2,4-dihydroxy-phenyl)-4-(4-methoxyphenyl)2H-pyrazole-3-carbonyl]amino]propyl]carbamate HOBT (572 mg, 4.2 mmol), NMM (1.55 ml, 14.1 mmol) and EDAC.HCl (820 mg, 4.3 mmol) were added at 0° C. consecutively to a solution of 5-(5-ethyl-2,4-dihydroxy-phenyl)-4-(4-methoxyphenyl)-2H-pyrazole-3-carboxylic acid (500 mg, 1.4 mmol) in 40 ml of dry DCM. The resulting mixture was stirred at 0° C. for 15 minutes. Then a solution of N—BOC-1,3-diaminopropane (740 mg, 4.3 mmol) in 5 ml of dry DCM was added. The resulting mixture was stirred at 0° C. for one our and at room temperature for 2.5 hours. The reaction mixture was washed with 50 ml of 10% w/v aqueous citric acid solution, 50 ml 20% aqueous KHCO3 solution and 50 ml of distilled water. The organic extracts were dried over MgSO4 and evaporated under reduced pressure. The crude material was purified by automated column chromatography on a 40 g RediSep™ normal phase silica cartridge using an ISCO Companion™ eluting with a mixture of 5% methanol in DCM was used. The fractions containing the desired product were combined and evaporated under reduced pressure go give the title compound as a white solid (450 mg, 63%); $^1$H NMR Spectrum: δH (400 MHz, DMSO-d6) 0.90 (3H t, J=7.5 Hz), 1.38 (9H, s), 1.56 (2H t, J=6.9 Hz), 2.28 (2H q, J=7.4 Hz), 2.95 (2H d, J=6.1 Hz), 3.15-3.20 (2H, m), 3.72 (3H, s), 6.41 (1H, s), 6.57 (2H, s), 6.72 (1H, s br), 6.78 (2H d, J=7.3 Hz), 7.12-7.14 (2H, m), 7.92-8.02 (1H, m br), 9.28-9.35 (2H, m), 12.89 (1H, s, br);

Mass Spectrum: (M+H$^+$) 511.12; (M–H$^+$) 509.2, (M-$^t$Bu) 455.08, (M-BOC) 411.09.

Preparation of N-(3-aminopropyl)-5-(5-ethyl-2,4-dihydroxy-phenyl)-4-(4-methoxyphenyl)-2H-pyrazole-3-carboxamide Tert-butyl N-[3-[[5-(5-ethyl-2,4-dihydroxy-phenyl)-4-(4-methoxyphenyl)2H-pyrazole-3-carbonyl]amino]propyl]carbamate (350 mg) was added as a solution in 15 ml dry methanol at room temperature to a solution of 4M HCl in dioxin (15 ml). The resulting solution was warmed to 50° C. for 2 hours. The mixture was cooled to room temperature before it was evaporated to dryness under reduced pressure. The residue was dissolved in methanol and loaded onto a 20 g SCX-2 cartridge. The cartridge was washed with methanol before the product was eluted with a mixture of methanol and 7N ammonia. The fractions containing the desired product were combined and evaporated under vacuum to give a light brown solid (326 mg). The material was subsequently suspended with dry di-ethylether (50 mg) and stirred over night. The resulting material was filtered off and dried and was identified as the title compound as a light brown solid (274 mg, 83%);

$^1$H NMR Spectrum: (400.132 MHz, d$^6$-DMSO) δ 0.89 (3H, t, J=8.0 Hz), 1.77 (2H, m), 2.27 (q, J=6.8 Hz, 2H), 2.79 (2H, m), 3.26 (2H, q, J=6.2 Hz), 3.72 (3H, s), 6.46 (1H, s), 6.55 (1H, s), 6.79 (2H, d, J=8.8 Hz), 7.13 (2H, d, J=8.8 Hz), 7.90 (2H, s br), 8.20 (1H, t, J=5.8 Hz), 9.40 (1H, s br); Mass Spectrum: (M+H⁺) 411.30; (M−H⁺) 409.27.

Test (b) Cellular Assay

HSP90 mediated regulation of both Her2 and Androgen Receptor is well documented and assays to measure HSP90 inhibition are described in the literature. Her2 down regulation in SKBr3 breast cell line can be monitored using an antibody in ELISA or Western blot analysis after exposure to an HSP90 inhibitor (Huezo et al, Chemistry and Biology, 2003, 10, 629-634). Alternatively a fluorescently labelled antibody can be used to detect Her2 levels using a plate reader. Reduction of Androgen Receptor levels by HSP90 inhibitors, as measured by antibody detection, in prostate cell lines e.g. LNCaP, CWR22, can also be used to measure cellular activity (Solit et al, Clin. Can. Res., 2002, 8, 986-993).

Although the pharmacological properties of the compounds of the formula I vary with structural change as expected, in general activity possessed by compounds of the formula I, may be demonstrated at the following concentrations or doses in one or more of the above tests (a) or (b) of for example:—

Test (a):- IC$_{50}$ of less than 200 μM, generally in the range of, for example, 10 nM to 150 μM (for example 10 nM to 100 μM). Preferred compounds are those with an IC$_{50}$ of less that 5 μM, more preferably less than 1 μM.
Test (b):- IC$_{50}$ in the range, for example, 0.1 nM to 10 μM.

By way of example, activity for the following compounds was observed in Test (a):

| Example | IC50 (μM) |
|---|---|
| 1 | 10.03 |
| 2.1 | 14.84 |
| 2.2 | 0.8572 |
| 2.3 | 1.157 |
| 3 | 18.44 |
| 4.1 | 16.65 |
| 4.2 | 0.7883 |
| 4.3 | 0.33 |
| 5 | 81.1 |
| 6.1 | 152 |
| 6.2 | 2.871 |
| 6.3 | 15.64 |
| 6.4 | 12.99 |
| 7.1 | 1.942 |
| 7.2 | 0.5265 |
| 7.3 | 0.3252 |
| 7.4 | 1.796 |
| 8 | 0.1003 |
| 9 | 1.39 |
| 10 | 1.216 |
| 11.1 | 1.94 |
| 11.2 | 0.128 |
| 11.3 | 7.827 |
| 11.4 | 0.1909 |
| 11.5 | 3.777 |
| 11.6 | 0.09679 |
| 11.7 | 0.3749 |
| 11.8 | 0.552 |
| 11.9 | 0.3245 |
| 11.10 | 0.8032 |
| 11.11 | 6.089 |
| 11.12 | 16.03 |
| 11.13 | 4.853 |
| 11.14 | 2.397 |
| 11.15 | 0.5631 |
| 11.16 | 0.5421 |
| 11.17 | 1.481 |
| 11.18 | 0.1659 |
| 11.19 | 0.6192 |
| 11.20 | 2.681 |
| 11.21 | 4.611 |
| 11.22 | 0.288 |
| 11.23 | 0.04956 |
| 11.24 | 0.0818 |
| 12 | 7.339 |
| 13 | 1.747 |
| 14.1 | 1.635 |
| 14.2 | 1.616 |
| 15 | 0.808 |

The data in the above table was generated in an assay substantially as described above in relation to in-vitro Binding Assay (a). Some of the compounds shown in the table were tested more than once in the assay. For those compounds the IC$_{50}$ value shown is the geometric mean of the measured IC$_{50}$ values. Therefore, as will be understood, the IC$_{50}$ values quoted above are not absolute and further measurements of the IC$_{50}$ values may result in a different mean IC$_{50}$ value.

The compounds of examples 5 and 6.1 exhibited low activity in the enzyme assay, test (a). Accordingly these compounds are not preferred compounds. Accordingly, in one embodiment the compounds of examples 5 and 6.1 are excluded ((7S)-8-[(4-methoxy-3,5-dimethylpyridin-2-yl)methyl]-7-methyl-5,6,7,8-tetrahydropteridin-2-amine and (7S)-8-[(4-methoxy-3,5-dimethylpyridin-2-yl)methyl]-5,7-dimethyl-5,6,7,8-tetrahydropteridin-2-amine).

Pharmaceutical Compositions

According to a further aspect of the invention there is provided a pharmaceutical composition which comprises a compound of the formula I, or a pharmaceutically acceptable salt or N-oxide or prodrug thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of infection is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

The compounds of the present invention are expected to possess, amongst others, anti-angiogenic properties such as anti-cancer properties that are believed to arise from their HSP90 inhibitory properties.

Accordingly, the compounds of the present invention are expected to be useful in the treatment of diseases or medical conditions mediated alone or in part by HSP90, i.e. the compounds may be used to produce an HSP90 inhibitory effect in a warm-blooded animal in need of such treatment. Thus the compounds of the present invention provide a method for the treatment of malignant cells characterised by inhibition of HSP90. Particularly the compounds of the invention may be used to produce an anti-tumour effect by means of anti-angiogenic and/or an anti-proliferative and/or anti-invasive effect and/or apoptotic and/or cell cycle arrest effect mediated alone or in part by the inhibition of HSP90. Particularly, the compounds of the present invention are expected to be useful in the prevention or treatment of those tumours that are sensitive to inhibition of HSP90 that are involved in for example, angiogenesis, proliferation, cell cycle regulation, invasion and the signal transduction steps associated therewith. Accordingly the compounds of the present invention may be useful in the treatment of hyperproliferative disorders including psoriasis, benign prostatic hyperplasia (BPH) and cancer by providing an anti-proliferative effect and/or anti-invasive and/or anti-angiogenic effect and/or a pro-apoptotic effect, particularly in the treatment of HSP90 sensitive cancers. Such benign or malignant tumours may affect any tissue and include non-solid tumours such as leukaemia, multiple myeloma or lymphoma, and also solid tumours, for example, oesophageal cancer, myeloma, hepatocellular, pancreatic, cervical cancer, ewings tumour, neuroblastoma, kaposis sarcoma, ovarian cancer, endometrial cancer, uterine cancer, vulval cancer, breast cancer, colorectal cancer, prostate cancer, bladder cancer, melanoma, lung cancer—non small cell lung cancer (NSCLC), and small cell lung cancer (SCLC), gastric cancer, head and neck cancer, renal cancer, bile duct cancer, bone cancer, neuronal cancer, testicular cancer, particularly ovarian cancer, breast cancer, colorectal cancer, prostate cancer and lung cancer—NSCLC and SCLC.

The compounds of the invention may also be useful in the treatment of pathogenic angiogenesis, for example in the treatment of cancers as hereinbefore described and other diseases in which inappropriate, or pathogenic angiogenesis occurs, for example diabetic retinopathy. The compounds of the invention may also be useful in the treatment or prophylaxis of other conditions in which HSP90 is implicated, for example inflammatory diseases, infections, autoimmune disorders, stroke, ischemia, cardiac disorders, neurological disorders and metabolic diseases, such as multiple sclerosis, lupus, rheumatoid arthritis and irritable bowel syndrome CJD, Huntington's disease and Alzheimer's disease. The compounds may also be useful for the protection of normal cells against chemotherapy induced toxicity, In another aspect of the present invention there is provided a compound of formula I, or a pharmaceutically acceptable salt or N-oxide or prodrug thereof, as defined hereinbefore for use as a medicament.

In another embodiment the present invention provides the use of a compound of formula I or a pharmaceutically acceptable or salt N-oxide or prodrug thereof in the preparation of a medicament.

In another embodiment the present invention provides a compound of formula I or a pharmaceutically acceptable salt or N-oxide or prodrug thereof for use in the treatment or prophylaxis of a cancer, for example a cancer involving a solid tumour.

In another embodiment the present invention provides a compound of formula I or a pharmaceutically acceptable salt or N-oxide or prodrug thereof for use in the treatment or prophylaxis of neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors.

In still another embodiment the present invention provides a compound of formula I or a pharmaceutically acceptable salt or N-oxide or prodrug thereof for use in the treatment or prophylaxis of pathologically angiogenic diseases, inflammatory diseases, infections, autoimmune disorders, stroke, ischemia, cardiac disorders, neurological disorders and metabolic diseases.

In another embodiment the present invention provides a compound of formula I or a pharmaceutically acceptable salt or N-oxide or prodrug thereof for use in the inhibition of HSP90 activity.

In another embodiment the present invention provides a compound of formula I or a pharmaceutically acceptable salt or N-oxide or prodrug thereof for use as an antiangiogenic agent in the treatment of a solid tumour.

In another embodiment the present invention provides the use of a compound of formula I or a pharmaceutically acceptable salt or N-oxide or prodrug thereof in the preparation of a medicament for the treatment or prophylaxis of a cancer, for example a cancer involving a solid tumour.

In another embodiment the present invention provides the use of a compound of formula I or a pharmaceutically acceptable salt or N-oxide or prodrug thereof in the preparation of a medicament for the treatment or prophylaxis of neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors.

In still another embodiment the present invention provides the use of a compound of formula I or a pharmaceutically acceptable salt or N-oxide or prodrug thereof in the preparation of a medicament for the treatment or prophylaxis of pathologically angiogenic diseases, inflammatory diseases, infections, autoimmune disorders, stroke, ischemia, cardiac disorders, neurological disorders and metabolic diseases.

In another embodiment the present invention provides the use of a compound of formula I or a pharmaceutically acceptable salt or N-oxide or prodrug thereof in the preparation of a medicament for use in the inhibition of HSP90 activity.

In another embodiment the present invention provides the use of a compound of formula I or a pharmaceutically acceptable salt or N-oxide or prodrug thereof in the manufacture of a medicament for use as an antiangiogenic agent in the treatment of a solid tumour.

In a further aspect of the invention there is provided a pharmaceutical composition which comprises a compound of the formula I, or a pharmaceutically acceptable salt or N-oxide or prodrug thereof, as defined herein before in association with a pharmaceutically-acceptable diluent or carrier for use in the production of an HSP90 inhibitory effect in a warm-blooded animal such as man.

In a further aspect of the invention there is provided a pharmaceutical composition which comprises a compound of the formula I, or a pharmaceutically acceptable salt or N-oxide or prodrug thereof, as defined herein before in association with a pharmaceutically acceptable diluent or carrier for use in the production of an anti-cancer effect in a warm-blooded animal such as man.

In a further aspect of the invention there is provided a pharmaceutical composition which comprises a compound of the formula I, or a pharmaceutically acceptable salt or N-oxide or prodrug thereof, as defined herein before in association with a pharmaceutically acceptable diluent or carrier for use as an antiangiogenic agent in the treatment of a solid tumour.

In a further aspect of the invention there is provided a pharmaceutical composition which comprises a compound of the formula I, or a pharmaceutically acceptable salt or N-oxide or prodrug thereof, as defined herein before in association with a pharmaceutically-acceptable diluent or carrier for use in the treatment or prophylaxis of pathologically angiogenic diseases, inflammatory diseases, infections, autoimmune disorders, stroke, ischemia, cardiac disorders, neurological disorders and metabolic diseases.

In another embodiment the present invention provides a method of inhibiting pathogenic angiogenesis in a human or animal comprising administering to said human or animal a therapeutically effective amount of a compound of formula I or a pharmaceutically acceptable salt or N-oxide or prodrug thereof.

In a further embodiment the present invention provides a method of inhibiting HSP90 comprising administering to an animal or human in need of said inhibiting a therapeutically effective amount of a compound of formula I, or a pharmaceutically acceptable salt or N-oxide or prodrug thereof.

In a further embodiment the present invention provides a method of prophylaxis or treatment of a disease mediated in part or alone by HSP90 comprising administering to an animal or human in need of said inhibiting a therapeutically effective amount of a compound of formula I, or a pharmaceutically acceptable salt or N-oxide or prodrug thereof.

In another embodiment the present invention provides a method of treatment of a human or animal suffering from a cancer comprising administering to said human or animal a therapeutically effective amount of a compound of formula I, or a pharmaceutically acceptable salt or N-oxide or prodrug thereof.

In further embodiment the present invention provides a method of prophylaxis or treatment of cancer comprising administering to a human or animal in need of such treatment a therapeutically effective amount of a compound of formula I, or a pharmaceutically acceptable salt or N-oxide or prodrug thereof.

In another embodiment the present invention provides a method of treatment of a human or animal suffering from a neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors comprising administering to a human or animal in need of such treatment a therapeutically effective amount of a compound of formula I, or a pharmaceutically acceptable salt or N-oxide or prodrug thereof.

In another embodiment the present invention provides a method of treatment of a human or animal suffering from a pathologically angiogenic disease comprising administering to said human or animal a therapeutically effective amount of a compound of formula I or a pharmaceutically acceptable salt or N-oxide or prodrug thereof.

Combination Therapies

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as
N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to a further aspect of the invention there is provided a pharmaceutical product comprising a compound of the formula I as defined hereinbefore and an additional anti-tumour agent as defined hereinbefore for the conjoint treatment of cancer.

According to a further aspect of the invention there is provided a method of treatment of a human or animal suffering from a cancer comprising administering to said human or animal a therapeutically effective amount of a compound of formula I, or a pharmaceutically acceptable salt or prodrug or N-oxide thereof simultaneously, sequentially or separately with an additional anti-tumour agent as defined hereinbefore.

According to a further aspect of the invention there is provided a compound of formula I, or a pharmaceutically acceptable salt or prodrug or N-oxide thereof for use simultaneously, sequentially or separately with an additional anti-tumour agent as defined hereinbefore, in the treatment of a cancer.

Although the compounds of the formula I are primarily of value as therapeutic agents for use in warm-blooded animals (including man), they are also useful whenever it is required to inhibit the effects HSP90. Thus, they are useful as pharmacological standards for use in the development of new biological tests and in the search for new pharmacological agents.

EXAMPLES

The invention will now be illustrated in the following Examples in which, generally:

(i) operations were carried out at ambient temperature, i.e. in the range 17 to 25° C. and under an atmosphere of an inert gas such as nitrogen or argon unless otherwise stated;

(ii) in general, the course of reactions was followed by thin layer chromatography (TLC) and/or analytical high pressure liquid chromatography (HPLC); the reaction times that are given are not necessarily the minimum attainable;

(iii) when necessary, organic solutions were dried over anhydrous magnesium sulfate, work-up procedures were carried out using traditional layer separating techniques, evaporations were carried out either by rotary evaporation in vacuo or in a Genevac HT-4/EZ-2.

(iv) yields, where present, are not necessarily the maximum attainable, and when necessary, reactions were repeated if a larger amount of the reaction product was required;

(v) in general, the structures of the end-products of the formula I were confirmed by nuclear magnetic resonance (NMR) and/or mass spectral techniques; electrospray mass spectral data were obtained using a Waters ZMD or Waters ZQ LC/mass spectrometer acquiring both positive and negative ion data, generally, only ions relating to the parent structure are reported; proton NMR chemical shift values were measured on the delta scale using a Bruker DPX-400. The following abbreviations have been used: s, singlet; d, doublet; t, triplet; q, quartet; m, multiplet; br, broad;

(vi) unless stated otherwise compounds containing an asymmetric carbon and/or sulfur atom were not resolved;

(vii) intermediates were not necessarily fully purified but their structures and purity were assessed by TLC, analytical LCMS and/or NMR analysis;

(viii) unless otherwise stated, column chromatography (by the flash procedure) was performed on Merck Kieselgel silica (Art. 9385); medium pressure liquid chromatography (MPLC) used Silicycle® Isco™ compatible 40-63 μm 60 Å silica packed cartridges; Ion exchange chromatography was carried out with Isolute® strong cation exchange (SCX) cartridges.

(ix) the following analytical HPLC methods were used; in general, reversed-phase silica was used with a flow rate of about 1 ml per minute and detection was by Electrospray Mass Spectrometry and by UV absorbance at a wavelength of 254 nm;

(x) the following abbreviations have been used:—
DCM: Dichloromethane
DMF: N,N-Dimethylformamide
THF: Tetrahydrofuran
DIAD: Diisopropyl azodicarboxylate
DMSO: Dimethylsulfoxide
DMA: N,N-dimethylacetamide
MeOH: Methanol
HATU: O-(7-Azabenzotriazol-1-yl)-N,N,N',N'-Tetramethyluronium Hexafluoro-Phosphate Example 1

(7S)-2-amino-8-[(4-methoxy-3,5-dimethylpyridin-2-yl)methyl]-7-methyl-7,8-dihydropteridin-6(5H)-one

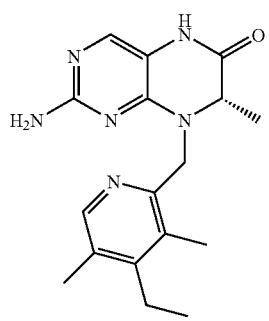

Methyl (2S)-2-[(2-amino-5-nitro-pyrimidin-4-yl)-[(4-methoxy-3,5-dimethyl-pyridin-2-yl)methyl]amino]propanoate (Intermediate 1)(500 mg, 1.28 mmol) was dissolved in acetic acid (4 mL) and heated to 70° C., then iron powder (144 mg, 2.58 mmol) was added. The mixture was stirred at 70° C. for 1 hour, then 100° C. for 30 minutes. The dark mixture was filtered through Celite®, and the filter media was washed with DCM. The filtrate was concentrated under reduced pressure, then purified by column chromatography (eluting with 5-20% methanol in DCM) to yield the title product as a cream foam (354 mg, 84%);

$^1$H NMR spectrum (400 MHz, DMSO-$d_6$) δ1.30 (3H, d), 2.18 (3H, s), 2.20 (3H, s), 3.73 (3H, s), 3.88 (1H, q), 4.15 (1H, d), 5.51 (1H, d), 5.83 (2H, s), 7.40 (1H, s), 8.18 (1H, s), 10.18 (1H, s); Mass spectrum:(M+H)$^+$ 329.

The methyl (2S)-2-[(2-amino-5-nitro-pyrimidin-4-yl)-[(4-methoxy-3,5-dimethyl-pyridin-2-yl)methyl]amino]propanoate (Intermediate 1) used as the starting material was prepared as follows:

Intermediate 2

Methyl (2S)-2-[(4-methoxy-3,5-dimethyl-pyridin-2-yl)methylamino]propanoate

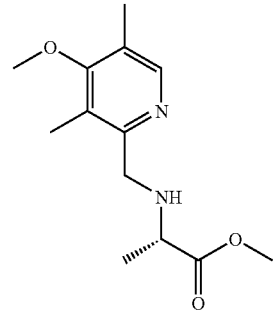

A suspension of alanine methyl ester hydrochloride (22.6 g, 162 mmol) in DMF (215 mL) was treated with diisopropylethylamine (56 mL, 0.32 mol) and stirred for 5 minutes until dissolution occurred. 2-Chloromethyl-3,5-dimethyl-4-methoxypyridine, hydrochloride (12 g, 54 mmol) was added portionwise and the resulting solution was stirred overnight at room temperature. The mixture was heated to 50° C. for 1.5 hours. The mixture was partitioned between ethyl acetate and saturated sodium bicarbonate. The organics were washed twice with water and brine, then dried with magnesium sulfate and concentrated under reduced pressure. The residue was purified by MPLC on silica using gradient elution (3% methanol/DCM to 10% methanol/DCM). Intermediate 2 was obtained as a yellow oil (9.76 g); $^1$H NMR spectrum (400 MHz, CDCl$_3$) δ1.38 (3H, d), 2.21 (3H, s), 2.23 (3H, s), 3.50 (1H, q), 3.71 (3H, s), 3.74 (3H, s), 3.78 (1H, d), 3.84 (1H, d), 8.20 (1H, s); Mass spectrum: (M+H)$^+$ 253.

Intermediate 3

Methyl (2S)-2-[(2-chloro-5-nitro-pyrimidin-4-yl)-[(4-methoxy-3,5-dimethyl-pyridin-2-yl)methyl]amino]propanoate

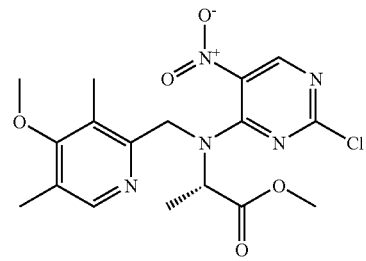

Methyl (2S)-2-[(4-methoxy-3,5-dimethyl-pyridin-2-yl)methylamino]propanoate (Intermediate 2)(2.9 g, 11.5 mmol) in acetone (15 mL) was added to a mixture of 2,4-dichloro-5-nitro-pyrimidine (2.23 g, 11.5 mmol) and potassium carbonate (1.64 g, 11.90 mmol) in acetone (10 mL). The mixture was stirred for 30 minutes at room temperature then partitioned between ethyl acetate and water. The organics were dried with magnesium sulfate and concentrated under reduced pressure. The residue was purified by MPLC on silica using gradient elution (15% ethyl acetate/isohexane to 50% ethyl acetate/isohexane) to give Intermediate 3 as a yellow gum (2.29 g, 49%). $^1$H NMR spectrum (400 MHz, CDCl$_3$) δ1.63 (3H, d), 2.14 (3H, s), 2.21 (3H, s), 3.74 (3H, s), 3.76 (3H, s), 4.50 (1H, d), 4.81 (1H, d), 5.27 (1H, q), 8.02 (1H, s), 8.50 (1H, s); Mass spectrum: (M+H)$^+$ 410,412.

Intermediate 1

Methyl (2S)-2-[(2-amino-5-nitro-pyrimidin-4-yl)-[(4-methoxy-3,5-dimethyl-pyridin-2-yl)methyl]amino]propanoate

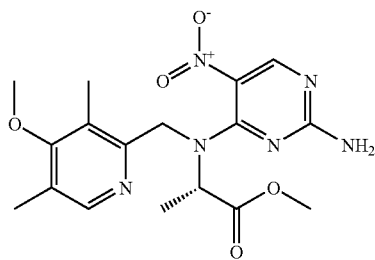

A solution of methyl (2S)-2-[(2-chloro-5-nitro-pyrimidin-4-yl)-[(4-methoxy-3,5-dimethyl-pyridin-2-yl)methyl]amino]propanoate (Intermediate 3)(1.0 g, 2.44 mmol) in THF (30 mL) was treated with ammonia (28% in water, 3 mL). The reaction mixture was stirred at room temperature for 2.5 hours, then partitioned between DCM and water. The organic solution was dried with magnesium sulfate and concentrated under reduced pressure. The residue was purified by MPLC on silica using gradient elution (30% ethyl acetate/isohexane to 100% ethyl acetate). Intermediate 1 was obtained as a yellow foam (770 mg, 81%); $^1$H NMR spectrum: (400 MHz CDCl$_3$) δ1.63 (3H, d), 2.10 (3H, s), 2.22 (3H, s), 3.65 (3H, s), 3.74 (3H, s), 4.44 (1H, d), 4.64-4.72 (2H, m), 5.24 (2H, s), 8.14 (1H, s), 8.66 (1H, s); Mass spectrum: (M+H)$^+$ 391.

Example 2

Using a similar procedure to that described in Example 1, the compounds shown in Table 1 were prepared by cyclising the appropriate nitropyrimidine starting materials shown as "SM" in Table 1.

TABLE 1

| No. and Note | Compound | SM |
|---|---|---|
| [1] | (7S)-2-amino-8-[(4-methoxy-3,5-dimethylpyridin-2-yl)methyl]-7-propyl-7,8-dihydropteridin-6(5H)-one | Intermediate 4 |
| [2] | (7R)-2-amino-8-[(4-methoxy-3,5-dimethylpyridin-2-yl)methyl]-7-methyl-7,8-dihydropteridin-6(5H)-one | Intermediate 5 |
| [3] | 2-amino-8-[(4-methoxy-3,5-dimethylpyridin-2-yl)methyl]-7,8-dihydropteridin-6(5H)-one | Intermediate 6 |

Notes for Table 1

The products gave the characterising data shown below:

[1] $^1$H NMR spectrum: (400 MHz, DMSO-d$_6$) δ0.85 (3H, t), 1.18-1.30 (2H, m), 1.71-1.79 (2H, m), 2.18 (3H, s), 2.20 (3H, s), 3.73 (3H, s), 3.85-3.87 (1H, m), 4.12 (1H, d), 5.57 (1H, d), 5.81 (2H, s), 7.36 (1H, s), 8.17 (1H, s), 10.22 (1H, s); Mass spectrum: (M+H)$^+$ 359.

[2] $^1$H NMR spectrum (400 MHz, DMSO-d$_6$) δ1.30 (3H, d), 2.19 (4H, s), 2.20 (3H, s), 3.73 (3H, s), 3.88 (1H, q), 4.15 (1H, d), 5.51 (1H, d), 5.83 (2H, s), 7.40 (1H, s), 8.18 (1H, s), 10.18 (1H, s); Mass spectrum: (M+H)$^+$ 329.

[3] $^1$H NMR spectrum: (400 MHz, DMSO-d$_6$) δ2.19 (3H, s), 2.20 (3H, s), 3.73 (3H, s), 4.00 (2H, s), 4.76 (2H, s), 5.73 (2H, s), 7.35 (1H, s), 8.15 (1H, s), 10.24 (1H, s); Mass spectrum: (M+H)$^+$ 315.

The Intermediate 4 used as the starting material was benzyl (2S)-2-[(2-amino-5-nitro-pyrimidin-4-yl)-[(4-methoxy-3,5-dimethyl-pyridin-2-yl)methyl]amino]pentanoate and was prepared as follows:

Intermediate 7

Benzyl (2S)-2-[(4-methoxy-3,5-dimethyl-pyridin-2-yl)methylamino]pentanoate

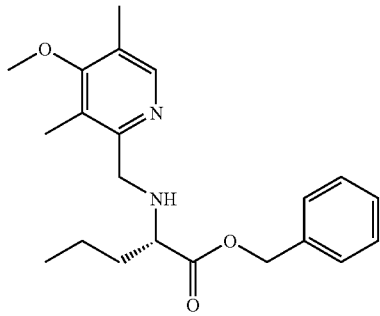

Intermediate 7 was prepared using an analogous method to that used for the preparation of Intermediate 2, except commercially available L-norvaline benzyl ester, 4-toluenesulfonate was used in place of L-alanine methyl ester, hydrochloride to give Intermediate 7 as yellow oil (11.15 g); $^1$H NMR spectrum (400 MHz, CDCl$_3$) δ0.88 (3H, t), 1.35-1.43 (2H, m), 1.62 (1H, s), 1.64-1.75 (1H, m), 1.67-1.73 (2H, m), 2.16 (3H, s), 2.22 (3H, s), 3.41 (1H, t), 3.73 (3H, s), 3.74-3.83 (2H, m), 5.16 (2H, s), 7.29-7.36 (5H, m), 8.18 (1H, s); Mass spectrum: (M+H)$^+$ 357.

Intermediate 8

Benzyl (2S)-2-[(2-chloro-5-nitro-pyrimidin-4-yl)-[(4-methoxy-3,5-dimethyl-pyridin-2-yl)methyl]amino]pentanoate

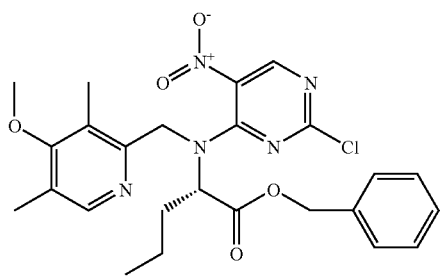

Intermediate 8 was prepared using an analogous method to that used for the preparation of Intermediate 3, except Intermediate 7 was used in place of Intermediate 2 to give Intermediate 8 as a yellow gum (7.44 g); $^1$H NMR spectrum (400 MHz, CDCl$_3$) δ0.96 (3H, t), 1.50-1.57 (2H, m), 1.85-2.15 (5H, m), 2.17 (3H, s), 3.69 (3H, s), 4.49 (1H, d), 4.68 (1H, d), 5.06 (1H, d), 5.19 (1H, d), 5.49-5.53 (1H, m), 7.29-7.36 (5H, m), 7.91 (1H, s), 8.46 (1H, s); Mass spectrum: (M+H)$^+$ 514, 516.

Intermediate 4

Benzyl (2S)-2-[(2-amino-5-nitro-pyrimidin-4-yl)-[(4-methoxy-3,5-dimethyl-pyridin-2-yl)methyl]amino]pentanoate

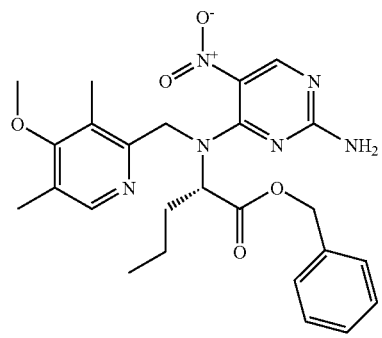

Intermediate 4 was prepared using an analogous method to that used for the preparation of Intermediate 1, except Intermediate 8 was aminated in place of Intermediate 3 to give Intermediate 4 (4.49 g); $^1$H NMR spectrum (400 MHz, CDCl$_3$) δ0.96 (3H, t), 1.50-1.58 (2H, m), 1.98 (3H, s), 2.00-2.14 (2H, m), 2.19 (3H, s), 3.66 (3H, s), 4.47 (1H, d), 4.54 (1H, d), 4.74-4.77 (1H, m), 4.87-4.97 (3H, m), 5.04 (1H, d), 7.19-7.21 (2H, m), 7.28-7.33 (3H, m), 8.07 (1H, s), 8.63 (1H, s); Mass spectrum: (M+H)$^+$ 495.

The Intermediate 5 used as the starting material was methyl (2R)-2-[(2-amino-5-nitro-pyrimidin-4-yl)-[(4-methoxy-3,5-dimethyl-pyridin-2-yl)methyl]amino]propanoate and was prepared as follows:

Intermediate 9

Methyl (2R)-2-[(4-methoxy-3,5-dimethyl-pyridin-2-yl)methylamino]propanoate

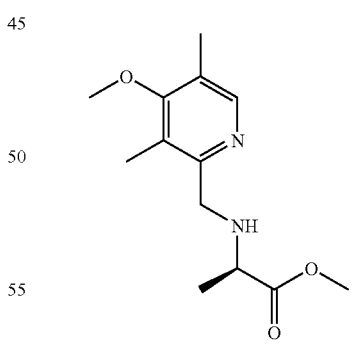

Intermediate 9 was prepared using an analogous method to that used for the preparation of Intermediate 2, except commercially available D-alanine methyl ester, hydrochloride was used in place of L-alanine methyl ester, hydrochloride to give Intermediate 9 as a yellow oil (12.8 g); $^1$H NMR spectrum: (400 MHz, DMSO-d$_6$) δ1.23 (d, 3H), 3.41 (q, 1H), 3.63 (s, 3H), 3.72 (s, 3H), 8.16 (s, 1H); Mass spectrum: (M+H)$^+$ 253.

Intermediate 5

Methyl (2R)-2-[(2-amino-5-nitro-pyrimidin-4-yl)-[(4-methoxy-3,5-dimethyl-pyridin-2-yl)methyl]amino]propanoate

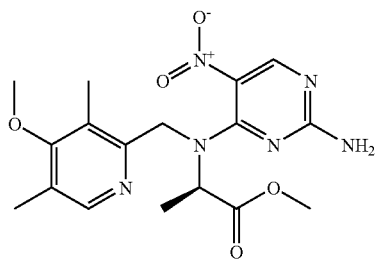

Intermediate 9 (11.61 g, 46 mmol) in acetone (15 mL) was added to a mixture of 2,4-dichloro-5-nitro-pyrimidine (8.93 g, 46 mmol) and potassium carbonate (6.91 g, 50 mmol) in acetone (100 mL). The mixture was stirred for 30 minutes at room temperature and then the reaction mixture was filtered to remove unwanted salts. The filtrate was evaporated under reduced pressure and the residue was purified by flash column chromatography on silica eluting with a gradient of 10% to 100% ethyl acetate/isohexane to afford a yellow oil (3.5 g); Mass spectrum: $(M+H)^+$ 410, 412. This material was treated with concentrated aqueous ammonia (20 mL) in THF (70 mL). The mixture was vigorously stirred for 2 hours before being partitioned between DCM and water. The organics were dried with magnesium sulfate and concentrated under reduced pressure. The residue was purified by flash column chromatography on silica using gradient elution (30% ethyl acetate/isohexane to 100% ethyl acetate). Intermediate 5 was obtained as a yellow crystalline solid (1.73 g, 53%); $^1$H NMR spectrum (400 MHz, CDCl$_3$) δ1.63 (3H, d), 2.10 (3H, s), 2.22 (3H, s), 3.65 (3H, s), 3.74 (3H, s), 4.44 (1H, s), 4.62-4.73 (2H, m), 5.23 (2H, s), 8.14 (1H, s), 8.66 (1H, s); Mass spectrum: $(M+H)^+$ 391.

The Intermediate 6 used as the starting material was methyl 2-[(2-amino-5-nitro-pyrimidin-4-yl)-[(4-methoxy-3,5-dimethyl-pyridin-2-yl)methyl]amino]acetate and was prepared as follows:

Intermediate 10

Methyl 2-[(4-methoxy-3,5-dimethyl-pyridin-2-yl)methylamino]acetate

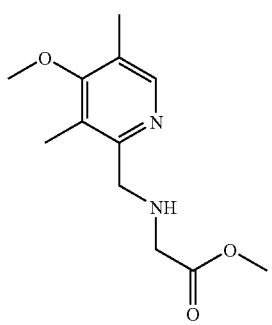

Intermediate 10 was prepared using an analogous method to that used for the preparation of Intermediate 2, except commercially available glycine methyl ester, hydrochloride was used in place of L-alanine methyl ester, hydrochloride to give Intermediate 10 as a yellow oil (9.96 g); $^1$H NMR spectrum: (400 MHz, CDCl$_3$) δ1.87 (2H, s), 2.20 (3H, s), 2.24 (3H, s), 3.75 (3H, s), 3.92-3.93 (2H, m), 8.21 (1H, s); Mass spectrum: $(M+H)^+$ 239.

Intermediate 11

Methyl 2-[(2-chloro-5-nitro-pyrimidin-4-yl)-[(4-methoxy-3,5-dimethyl-pyridin-2-yl)methyl]amino]acetate

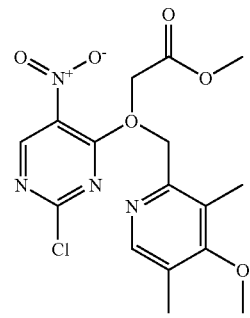

Intermediate 11 was prepared using an analogous method to that used for the preparation of Intermediate 3, except Intermediate 10 was used in place of Intermediate 2 to give Intermediate 11 as a brown oil (6.28 g); $^1$H NMR spectrum: (500 MHz, DMSO-d$_6$) δ2.15 (3H, s), 2.18 (4H, s), 3.70 (3H, s), 3.73 (3H, s), 4.46 (2H, s), 4.85 (2H, s), 8.09 (1H, s), 8.83 (1H, s); Mass spectrum: $(M+H)^+$ 396, 398.

Intermediate 6

Methyl 2-[(2-amino-5-nitro-pyrimidin-4-yl)-[(4-methoxy-3,5-dimethyl-pyridin-2-yl)methyl]amino]acetate

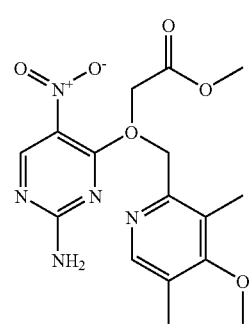

Intermediate 6 was prepared using an analogous method to that used for the preparation of Intermediate 1, except Intermediate 11 was used in place of Intermediate 3 to give Intermediate 6 as a yellow solid (2.87 g); $^1$H NMR spectrum (300 MHz, DMSO-d$_6$) δ2.10 (3H, s), 2.18 (3H, s), 3.64 (3H, s), 3.71 (3H, s), 4.23 (2H, s), 4.71 (2H, s), 7.28 (1H, s), 7.42 (1H, s), 8.10 (1H, s), 8.66 (1H, s) Mass spectrum: (M+H)⁺ 377.

Example 3

(7S)-2-amino-8-[(4-methoxy-3,5-dimethylpyridin-2-yl)methyl]-5,7-dimethyl-7,8-dihydropteridin-6(5H)-one

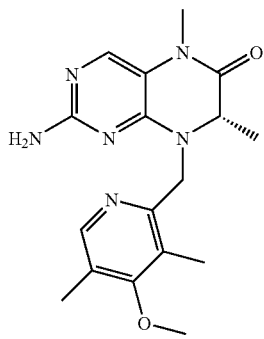

(7S)-2-amino-8-[(4-methoxy-3,5-dimethylpyridin-2-yl)methyl]-7-methyl-7,8-dihydropteridin-6(5H)-one (Example 1)(164 mg, 0.5 mmol) was stirred in anhydrous THF (1 mL) and triphenylphosphine (400 mg, 1.53 mmol) and methanol (0.2 mL, 4.94 mmol) were added. DIAD (0.3 mL, 1.52 mmol) was added dropwise and the mixture was stirred at room temperature overnight. The reaction mixture was loaded onto a SCX cartridge and washed with THF and methanol, then eluting with methanolic ammonia (7M). The crude product was further purified by MPLC eluting with 0-15% methanol/DCM. The title compound was isolated as a colourless foam after trituration and re-concentration from ether (113 mg, 66%); ¹H NMR spectrum (400 MHz, CDCl₃) δ1.39 (3H, d), 2.17 (3H, s), 2.25 (3H, s), 3.26 (3H, s), 3.75 (3H, s), 4.03-4.15 (2H, m), 4.66 (2H, s), 5.71 (1H, d), 7.57 (1H, s), 8.18 (1H, s); Mass spectrum: (M+H)⁺ 343.

Example 4

Using a similar procedure to that used for the synthesis of Example 3, the compounds shown in Table 2 were prepared from the appropriate 7,8-dihydropteridin-6-one (SM in Table 2) and appropriate alcohol (ROH in Table 2).

TABLE 2

| No. and Note | Compound | ROH | SM |
|---|---|---|---|
| [1] | (7S)-2-amino-5-ethyl-8-[(4-methoxy-3,5-dimethylpyridin-2-yl)methyl]-7-methyl-7,8-dihydropteridin-6(5H)-one | CH₃CH₂OH | Example 1 |
| | 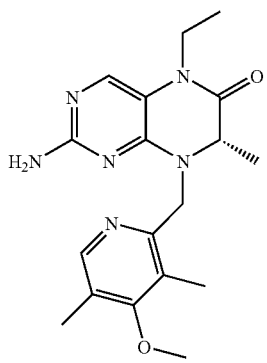 | | |
| [2] | (7R)-2-amino-8-[(4-methoxy-3,5-dimethylpyridin-2-yl)methyl]-5,7-dimethyl-7,8-dihydropteridin-6(5H)-one | CH₃OH | Example 2[2] |
| | 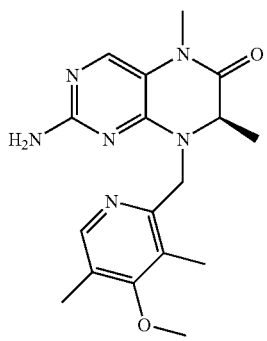 | | |

TABLE 2-continued

| No. and Note | Compound | ROH | SM |
|---|---|---|---|
| [3] | 2-amino-8-[(4-methoxy-3,5-dimethylpyridin-2-yl)methyl]-5-methyl-7,8-dihydropteridin-6(5H)-one | CH₃OH | Example 2[3] |

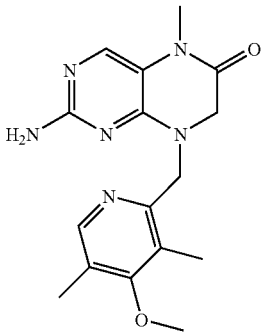

Notes for Table 2

The products gave the characterising data shown below:

[1] ¹H NMR spectrum (400 MHz, CDCl₃) δ1.22 (3H, t), 1.36 (3H, d), 2.17 (3H, s), 2.25 (3H, s), 3.70-3.81 (4H, m), 3.91-3.98 (1H, m), 4.03 (1H, q), 4.09 (1H, d), 4.66 (2H, s), 5.70 (1H, d), 7.60 (1H, s), 8.18 (1H, s); Mass spectrum: (M+H)⁺ 356.

[2] ¹H NMR spectrum (400 MHz, CDCl₃) δ1.39 (3H, d), 2.17 (3H, s), 2.25 (3H, s), 3.26 (3H, s), 3.75 (3H, s), 4.04-4.15 (2H, m), 4.65 (2H, s), 5.71 (1H, d), 7.57 (1H, s), 8.18 (1H, s); Mass spectrum: (M+H)⁺ 343.

[3] ¹H NMR spectrum: (400 MHz, DMSO-d₆) δ2.18 (3H, s), 2.20 (3H, s), 3.18 (3H, s), 3.73 (3H, s), 4.11 (2H, s), 4.78 (2H, s), 5.83 (2H, s), 7.57 (1H, s), 8.14 (1H, s); Mass spectrum: (M+H)⁺ 329.

Example 5

(7S)-8-[(4-methoxy-3,5-dimethylpyridin-2-yl)methyl]-7-methyl-5,6,7,8-tetrahydropteridin-2-amine

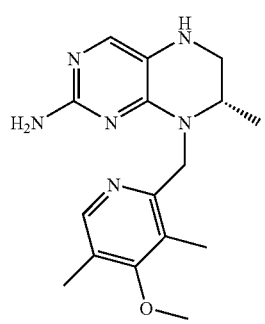

(7S)-2-amino-8-[(4-methoxy-3,5-dimethylpyridin-2-yl)methyl]-7-methyl-7,8-dihydropteridin-6(5H)-one (Example 1)(164 mg, 0.50 mmol) was stirred in THF (3 mL) and borane-THF complex (1M in THF, 2 mL, 2 mmol) was added slowly. The mixture was stirred at room temperature for 1 hour, then heated at reflux for 30 minutes. The mixture was slowly treated with hydrochloric acid (2M, 5 mL). The solution was loaded onto a SCX column and washed with methanol. The product was eluted with methanolic ammonia (7M) and the volatiles were removed under reduced pressure. Further purification was achieved by MPLC eluting with 5-30% methanol/DCM to give the title compound as a cream foam (115 mg, 73%); ¹H NMR spectrum (400 MHz, CDCl₃) δ1.22 (3H, d), 2.24 (6H, s), 2.94-2.97 (1H, m), 3.13-3.17 (1H, m), 3.20 (1H, s), 3.57-3.62 (1H, m), 3.75 (3H, s), 4.32 (1H, d), 4.36 (2H, s), 5.59 (1H, d), 7.33 (1H, s), 8.17 (1H, s);

Mass spectrum: (M+H)⁺ 315.

Example 6

Using a similar procedure to that used for the synthesis of Example 5, the compounds shown in Table 3 were prepared by reducing the appropriate 7,8-dihydropteridin-6-one (SM in Table 3).

TABLE 3
| No. and Note | Compound | SM |
|---|---|---|
| [1] | (7S)-8-[(4-methoxy-3,5-dimethylpyridin-2-yl)methyl]-5,7-dimethyl-5,6,7,8-tetrahydropteridin-2-amine (105 mg) 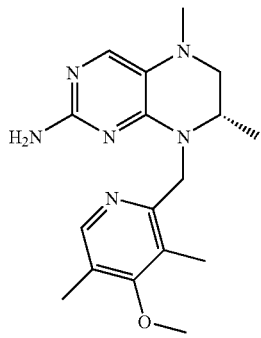 | Example 3 |
| [2] | (7R)-8-[(4-methoxy-3,5-dimethylpyridin-2-yl)methyl]-7-methyl-5,6,7,8-tetrahydropteridin-2-amine (70 mg) 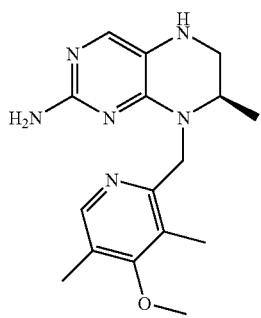 | Example 2[2] |
| [3] | (7R)-8-[(4-methoxy-3,5-dimethylpyridin-2-yl)methyl]-5,7-dimethyl-5,6,7,8-tetrahydropteridin-2-amine (47 mg) 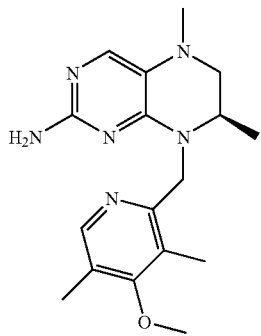 | Example 4[2] |

TABLE 3-continued

| No. and Note | Compound | SM |
|---|---|---|
| [4] | 8-[(4-methoxy-3,5-dimethylpyridin-2-yl)methyl]-5-methyl-5,6,7,8-tetrahydropteridin-2-amine 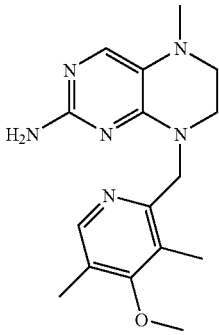 | Example 4[3] |

The products gave the characterising data shown below:

[1] ¹H NMR spectrum; (400 MHz, CDCl₃) δ 1.25 (3H, d), 2.22 (3H, s), 2.23 (3H, s), 2.72-2.74 (4H, m), 2.93-2.97 (1H, m), 3.59-3.64 (1H, m), 3.74 (3H, s), 4.32 (3H, d), 5.60 (1H, d), 7.18 (1H, s), 8.16 (1H, s); Mass spectrum: (M+H)⁺ 329.

[2] ¹H NMR spectrum: (400 MHz, CDCl₃) δ1.22 (3H, d), 2.24 (6H, s), 2.94-2.97 (1H, m), 3.13-3.17 (1H, m), 3.25 (1H, s), 3.57-3.61 (1H, m), 3.75 (3H, s), 4.32 (1H, d), 4.37 (2H, s), 5.59 (1H, d), 7.34 (1H, s), 8.17 (1H, s); Mass spectrum: (M+H)⁺ 315.

[3] ¹H NMR spectrum: (400 MHz, CDCl₃) δ 1.25 (3H, d), 2.22 (3H, s), 2.23 (3H, s), 2.72-2.74 (4H, m), 2.96 (1H, dd), 3.59-3.64 (1H, m), 3.74 (3H, s), 4.28-4.39 (3H, m), 5.60 (1H, d), 7.18 (1H, s), 8.16 (1H, s); Mass spectrum: (M+H)⁺ 329.

[4] ¹H NMR spectrum (300 MHz, CDCl₃) δ 2.15 (3H, s), 2.16 (3H, s), 2.63 (3H, s), 2.88 (2H, t), 3.38 (2H, t), 3.65-3.69 (3H, m), 4.34 (2H, s), 4.85 (2H, s), 7.10 (1H, s), 8.09 (1H, s); Mass spectrum: (M+H)⁺ 315.

Example 7

Using a similar procedure to that described in Example 1, the compounds shown in Table 4 were prepared by cyclising the appropriate nitropyrimidine starting materials shown as "SM" in Table 4.

TABLE 4

| No. and Note | Compound | SM |
|---|---|---|
| [1] | (7R)-2-amino-8-[(4-methoxy-3,5-dimethyl-pyridin-2-yl)methyl]-7-(2-methylpropyl)-7,8-dihydropteridin-6(5H)-one 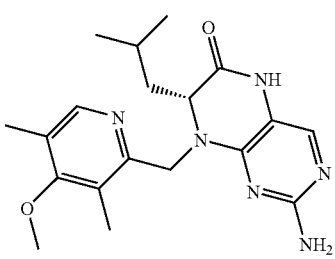 | Intermediate 12 |

TABLE 4-continued

| No. and Note | Compound | SM |
|---|---|---|
| [2] | (7R)-2-amino-7-benzyl-8-[(4-methoxy-3,5-dimethyl-pyridin-2-yl)methyl]-7,8-dihydropteridin-6(5H)-one | Intermediate 13 |
| [3] | Methyl {(7R)-2-amino-8-[(4-methoxy-3,5-dimethylpyridin-2-yl)methyl]-6-oxo-5,6,7,8-tetrahydropteridin-7-yl}acetate | Intermediate 14 |
| [4] | (7R)-2-amino-8-[(4-methoxy-3,5-dimethyl-pyridin-2-yl)methyl]-7-propyl-7,8-dihydropteridin-6(5H)-one | Intermediate 15 |

Notes for Table 1

The products gave the characterising data shown below:

[1] $^1$H NMR spectrum (400 MHz, CDCl$_3$) δ 0.91-0.93 (6H, m), 1.65-75 (3H, m), 2.16 (3H, s), 2.24 (3H, s), 3.75 (3H, s), 4.00 (1H, t), 4.12 (1H, d), 5.69-5.76 (3H, m), 7.42 (1H, s), 8.18 (1H, s), 11.50 (1H, br.); Mass spectrum: (M+H)$^+$.

[2] $^1$H NMR spectrum (400 MHz, CDCl$_3$) δ 2.13 (3H, s), 2.26 (3H, s), 3.08-3.13 (1H, m), 3.30-3.34 (1H, m), 3.76 (3H, s), 4.16 (1H, d), 4.35 (1H, t), 5.72 (2H, s), 5.77 (1H, d), 6.93 (1H, s), 7.07-7.19 (5H, m), 8.20 (1H, s); Mass spectrum: 405 (M+H)$^+$.

[3] $^1$H NMR spectrum (400 MHz, DMSO-d$_6$) δ 2.19 (6H, s), 2.72-2.92 (2H, m), 3.51 (3H, s), 3.73 (3H, s), 4.23 (1H, d), 4.29 (1H, t), 5.45 (1H, d), 5.76 (2H, s), 7.37 (1H, s), 8.14 (1H, s), 10.33 (1H, s); Mass spectrum: 387 (M+H)$^+$.

[4] $^1$H NMR spectrum (400 MHz, DMSO-d$_6$) δ 0.85 (3H, t), 1.12-1.35 (2H, m), 1.65-1.81 (2H, m), 2.17 (3H, s), 2.20 (3H, s), 3.73 (3H, s), 3.81-3.88 (1H, m), 4.11 (1H, d), 5.56 (1H, d), 5.80 (2H, s), 7.36 (1H, s), 8.17 (1H, s), 10.22 (1H, s); Mass spectrum: 357 (M+H)$^+$.

The Intermediate 12 used as the starting material was methyl (2R)-2-[(2-amino-5-nitro-pyrimidin-4-yl)-[(4-methoxy-3,5-dimethyl-pyridin-2-yl)methyl]amino]-4-methylpentanoate and was prepared as follows:

Intermediate 16

Methyl (2R)-2-[(4-methoxy-3,5-dimethyl-pyridin-2-yl)methylamino]-4-methyl-pentanoate

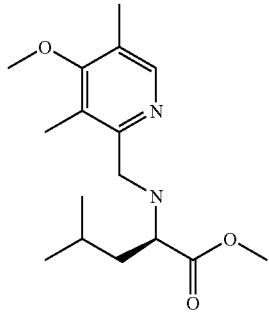

Intermediate 16 was prepared using an analogous method to that used for the preparation of Intermediate 2, except commercially available D-leucine methyl ester, hydrochloride was used in place of L-alanine methyl ester, hydrochloride to give Intermediate 16 as a yellow oil; $^1$H NMR spectrum (400 MHz, CDCl$_3$) δ0.86-0.93 (6H, dd), 1.53-1.57 (2H, t), 1.73-1.80 (1H, m), 2.22 (3H, s), 2.23 (3H, s), 3.40 (1H, t), 3.71 (3H, s), 3.74 (3H, s), 3.74-3.84 (2H, m), 8.19 (1H, s); Mass spectrum: (M+H)$^+$ 295.

Intermediate 17

Methyl (2R)-2-[(2-chloro-5-nitro-pyrimidin-4-yl)-[(4-methoxy-3,5-dimethyl-pyridin-2-yl)methyl]amino]-4-methyl-pentanoate

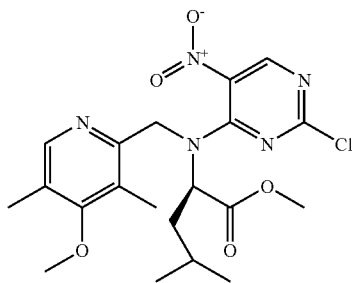

Intermediate 17 was prepared using an analogous method to that used for the preparation of Intermediate 3, except Intermediate 16 was used in place of Intermediate 2 to give Intermediate 17 as a yellow gum; $^1$H NMR spectrum (500 MHz, DMSO-d$_6$) δ0.93 (3H, d), 1.03 (3H, d), 1.81-1.91 (3H, m), 2.12 (3H, s), 2.19 (3H, s), 3.70 (3H, s), 3.72 (3H, s), 4.57 (1H, d), 4.78 (1H, d), 5.70-5.73 (1H, m), 7.96 (1H, s), 8.44 (1H, s);

Mass spectrum: (M+H)$^+$ 452, 454.

Intermediate 12

Methyl (2R)-2-[(2-amino-5-nitro-pyrimidin-4-yl)-[(4-methoxy-3,5-dimethyl-pyridin-2-yl)methyl]amino]-4-methyl-pentanoate

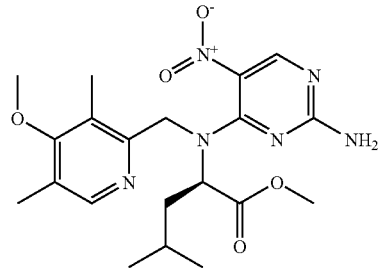

Intermediate 12 was prepared using an analogous method to that used for the preparation of Intermediate 1, except Intermediate 17 was used in place of Intermediate 3 to give Intermediate 12 as a yellow solid; $^1$H NMR spectrum (300 MHz, DMSO-d$_6$) δ0.88 (3H, d), 0.96 (3H, d), 1.77-1.85 (2H, m), 1.90-1.97 (1H, m), 2.04 (3H, s), 2.16 (3H, s), 3.51 (3H, s), 3.68 (3H, s), 4.48 (1H, d), 4.63 (1H, d), 5.15-5.18 (1H, m), 7.03-7.49 (2H, br), 8.05 (1H, s), 8.53 (1H, s); Mass spectrum: (M+H)$^+$ 433.

The Intermediate 13 used as the starting material was benzyl (2R)-2-[(2-amino-5-nitro-pyrimidin-4-yl)-[(4-methoxy-3,5-dimethyl-pyridin-2-yl)methyl]amino]-3-phenyl-propanoate and was prepared as follows:

Intermediate 18

Benzyl (2R)-2-[(4-methoxy-3,5-dimethyl-pyridin-2-yl)methylamino]-3-phenyl-propanoate

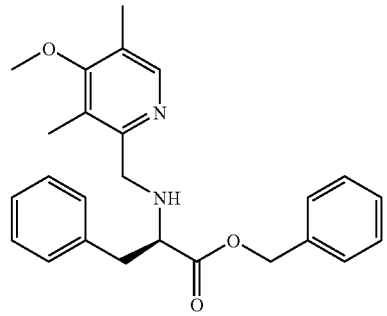

Intermediate 18 was prepared using an analogous method to that used for the preparation of Intermediate 2, except commercially available D-phenylalanine benzyl ester, 4-toluenesulfonate was used in place of L-alanine methyl ester, hydrochloride to give Intermediate 18 as a yellow oil; $^1$H NMR spectrum (400 MHz, CDCl$_3$) δ 2.09 (3H, s), 2.21 (3H, s), 3.02-3.04 (2H, m), 3.68 (1H, t), 3.71 (3H, s), 3.74-3.84 (2H, m), 5.02-5.09 (2H, m), 7.13-7.37 (10H, m), 8.14 (1H, s); Mass spectrum: (M+H)$^+$ 405.

Intermediate 19

Benzyl (2R)-2-[(2-chloro-5-nitro-pyrimidin-4-yl)-[(4-methoxy-3,5-dimethyl-pyridin-2-yl)methyl]amino]-3-phenyl-propanoate

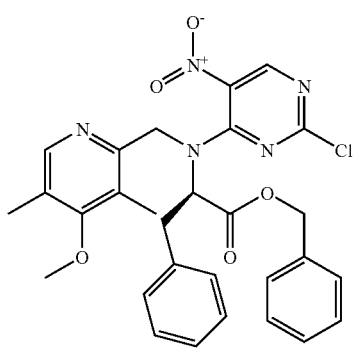

Intermediate 19 was prepared using an analogous method to that used for the preparation of Intermediate 3, except Intermediate 18 was used in place of Intermediate 2 to give Intermediate 19 as a yellow gum; $^1$H NMR spectrum (400 MHz, CDCl$_3$) δ1.98 (3H, s), 2.17 (3H, s), 3.33-3.46 (2H, m), 3.69 (3H, s), 4.41 (1H, d), 4.60 (1H, d), 5.00 (1H, d), 5.17 (1H, d), 5.54 (1H, t), 7.19-7.36 (10H, m), 7.93 (1H, s), 8.48 (1H, s); Mass spectrum: (M+H)$^+$ 562, 564.

Intermediate 13

Benzyl (2R)-2-[(2-amino-5-nitro-pyrimidin-4-yl)-[(4-methoxy-3,5-dimethyl-pyridin-2-yl)methyl]amino]-3-phenyl-propanoate

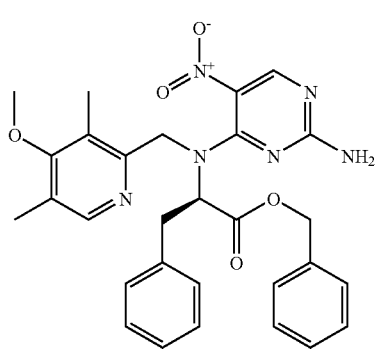

Intermediate 13 was prepared using an analogous method to that used for the preparation of Intermediate 1, except Intermediate 19 was used in place of Intermediate 3 to give Intermediate 13 as a yellow solid; $^1$H NMR spectrum (400 MHz, CDCl$_3$) δ1.97 (3H, s), 2.19 (3H, s), 3.38 (1H, dd), 3.55 (1H, dd), 3.67 (3H, s), 4.28 (1H, d), 4.53 (1H, d), 4.89-4.99 (4H, m), 5.05 (1H, d), 7.16-7.32 (10H, m), 8.08 (1H, s), 8.63 (1H, s); Mass spectrum: (M+H)$^+$ 543.

The Intermediate 14 used as the starting material was dimethyl (2R)-2-[(2-amino-5-nitro-pyrimidin-4-yl)-[(4-methoxy-3,5-dimethyl-pyridin-2-yl)methyl]amino]butanedioate and was prepared as follows:

Intermediate 20

Dimethyl (2R)-2-[(4-methoxy-3,5-dimethyl-pyridin-2-yl)methylamino]butanedioate

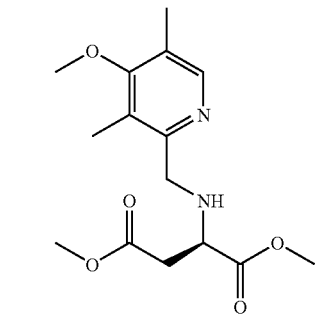

Intermediate 20 was prepared using an analogous method to that used for the preparation of Intermediate 2, except commercially available D-aspartic acid dimethyl ester, hydrochloride was used in place of L-alanine methyl ester, hydrochloride to give Intermediate 20 as a yellow oil; $^1$H NMR spectrum (400 MHz, CDCl$_3$) δ 2.21 (3H, s), 2.23 (3H, s), 2.70-2.76 (1H, m), 2.77-2.84 (1H, m), 3.68 (3H, s), 3.73 (3H, s), 3.75 (3H, s), 3.77-3.81 (1H, m), 3.84 (1H, d), 3.91 (1H, d), 8.18 (1H, s); Mass spectrum: (M+H)$^+$ 311.

Intermediate 21

Dimethyl (2R)-2-[(2-chloro-5-nitro-pyrimidin-4-yl)-[(4-methoxy-3,5-dimethyl-pyridin-2-yl)methyl]amino]butanedioate

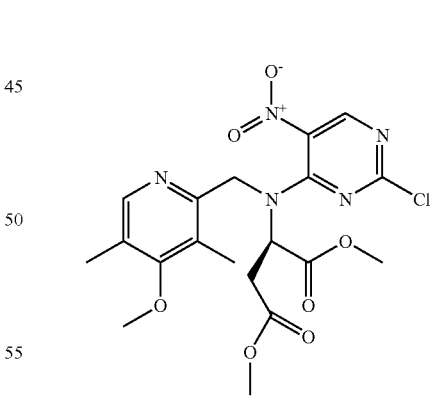

Intermediate 21 was prepared using an analogous method to that used for the preparation of Intermediate 3, except Intermediate 20 was used in place of Intermediate 2 to give Intermediate 21 as a yellow gum; $^1$H NMR spectrum (400 MHz, CDCl$_3$) δ 2.13 (3H, s), 2.20 (3H, s), 3.23 (1H, dd), 3.44 (1H, dd), 3.66 (3H, s), 3.74 (6H, s), 4.70 (1H, d), 4.77 (1H, d), 5.11-5.19 (1H, m), 8.00 (1H, s), 8.52 (1H, s); Mass spectrum: (M+H)$^+$ 468, 470.

Intermediate 14

Dimethyl (2R)-2-[(2-amino-5-nitro-pyrimidin-4-yl)-[(4-methoxy-3,5-dimethyl-pyridin-2-yl)methyl]amino]butanedioate

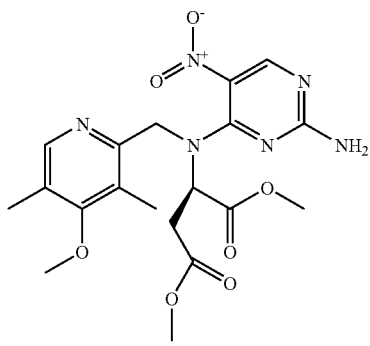

Intermediate 14 was prepared using an analogous method to that used for the preparation of Intermediate 1, except Intermediate 21 was used in place of Intermediate 3 to give Intermediate 14 as a yellow solid; $^1$H NMR spectrum (400 MHz, CDCl$_3$) δ2.10 (3H, s), 2.21 (3H, s), 3.20-3.26 (1H, m), 3.44-3.50 (1H, m), 3.65 (3H, s), 3.70 (3H, s), 3.74 (3H, s), 4.55 (1H, d), 4.68 (1H, d), 4.87-4.90 (1H, m), 5.25 (2H, s), 8.10 (1H, s), 8.65 (1H, s); Mass spectrum: (M+H)$^+$ 449.

The Intermediate 15 used as the starting material was benzyl (2R)-2-[(2-amino-5-nitro-pyrimidin-4-yl)-[(4-methoxy-3,5-dimethyl-pyridin-2-yl)methyl]amino]pentanoate and was prepared as follows:

Intermediate 22

Benzyl (2R)-2-[(4-methoxy-3,5-dimethyl-pyridin-2-yl)methylamino]pentanoate

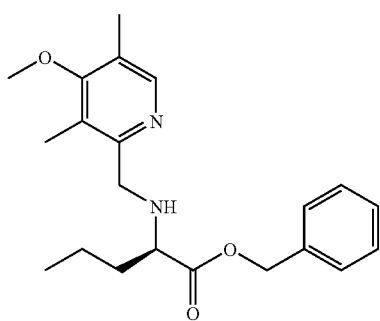

Intermediate 22 was prepared using an analogous method to that used for the preparation of Intermediate 2, except commercially available D-norvaline benzyl ester 4-toluenesulfonate was used in place of L-alanine methyl ester, hydrochloride to give Intermediate 22 as a yellow oil; $^1$H NMR spectrum (400 MHz, CDCl$_3$) δ0.88 (3H, t), 1.36-1.42 (2H, m), 1.62-1.75 (2H, m), 2.16 (3H, s), 2.22 (3H, s), 3.41 (1H, t), 3.73 (3H, s), 3.74-3.82 (2H, m), 5.16 (2H, s), 7.29-7.37 (5H, m), 8.18 (1H, s); Mass spectrum: (M+H)$^+$ 357.

Intermediate 23

Benzyl (2R)-2-[(2-chloro-5-nitro-pyrimidin-4-yl)-[(4-methoxy-3,5-dimethyl-pyridin-2-yl)methyl]amino]pentanoate

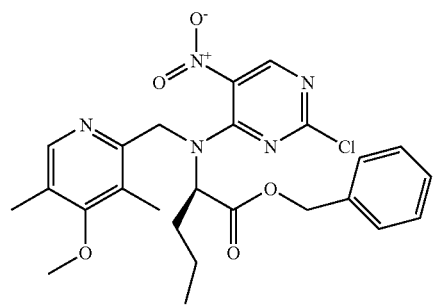

Intermediate 23 was prepared using an analogous method to that used for the preparation of Intermediate 3, except Intermediate 22 was used in place of Intermediate 2 to give Intermediate 23 as a yellow gum; $^1$H NMR spectrum (400 MHz, CDCl$_3$) δ 0.95 (3H, t), 1.48-1.60 (2H, m), 1.91-1.99 (1H, m), 2.02 (3H, s), 2.04-2.15 (1H, m), 2.17 (3H, s), 3.69 (3H, s), 4.48 (1H, d), 4.68 (1H, d), 5.06 (1H, d), 5.19 (1H, d), 5.49-5.53 (1H, m), 7.29-7.37 (5H, m), 7.91 (1H, s), 8.46 (1H, s); Mass spectrum: (M+H)$^+$ 514, 516.

Intermediate 15

Benzyl (2R)-2-[(2-amino-5-nitro-pyrimidin-4-yl)-[(4-methoxy-3,5-dimethyl-pyridin-2-yl)methyl]amino]pentanoate

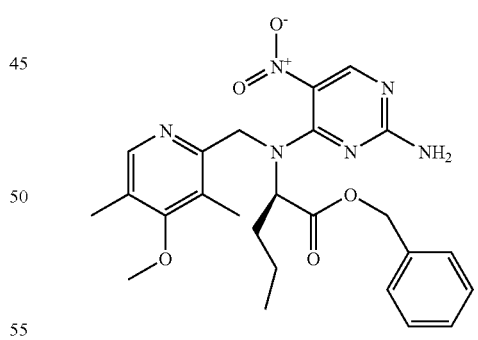

Intermediate 15 was prepared using an analogous method to that used for the preparation of Intermediate 1, except Intermediate 23 was used in place of Intermediate 3 to give Intermediate 15 as a yellow solid; $^1$H NMR spectrum (400 MHz, CDCl$_3$) δ0.96 (3H, t), 1.50-1.61 (2H, m), 1.99 (3H, s), 2.01-2.16 (2H, m), 2.19 (3H, s), 3.66 (3H, s), 4.47 (1H, d), 4.54 (1H, d), 4.74-4.78 (1H, m), 4.85-4.98 (3H, m), 5.04 (1H, d), 7.19-7.22 (2H, m), 7.28-7.33 (3H, m), 8.07 (1H, s), 8.63 (1H, s); Mass spectrum: (M+H)$^+$ 495.

Example 8

2-Amino-4-chloro-8-[(4-methoxy-3,5-dimethyl-pyridin-2-yl)methyl]-5,7-dihydropteridin-6-one

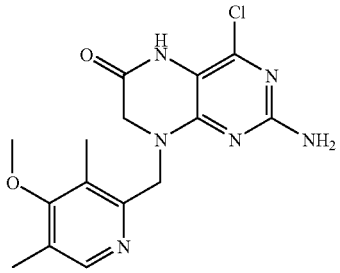

Methyl 2-[(2-amino-6-chloro-5-nitro-pyrimidin-4-yl)-[(4-methoxy-3,5-dimethyl-pyridin-2-yl)methyl]amino]acetate (Intermediate 25)(2.0 g) was dissolved in acetic acid (120 mL) and warmed to 65° C. Iron powder (5 g) was added and the mix heated at 85° C. for 40 minutes. The reaction mixture allowed to cool, filtered and the filtrate was evaporated to dryness. The residue was purified by flash chromatography on silica, eluting with increasingly polar mixtures of methanol DCM (1/99-10/90) to give crude product. The crude product was triturated with methanol (3 mL) and the resulting solid filtered off then redissolved in 5N aqueous HCl (5 mL) and heated at 80° C. for 30 minutes. The reaction mixture was cooled, evaporated to dryness and the residue triturated with aqueous ammonia solution (d=0.880). The resulting solid was filtered off to give the title compound (129 mg) as a beige coloured solid; $^1$H NMR spectrum (400 MHz, DMSO) 2.20 (6H, s), 3.74 (3H, s), 4.05 (2H, s), 4.79 (2H, s), 6.17 (2H, s), 8.15 (1H, s), 9.92 (1H, s);

Mass spectrum: (M+H)$^+$ 349.37, 351.33

The methyl 2-[(2-amino-6-chloro-5-nitro-pyrimidin-4-yl)-[(4-methoxy-3,5-dimethyl-pyridin-2-yl)methyl]amino]acetate (Intermediate 25) used as starting material was made as follows:

Intermediate 24

Methyl-2-[(2-amino-6-hydroxy-5-nitro-pyrimidin-4-yl)-[(4-methoxy-3,5-dimethyl-pyridin-2-yl)methyl]amino]acetate, DMF adduct

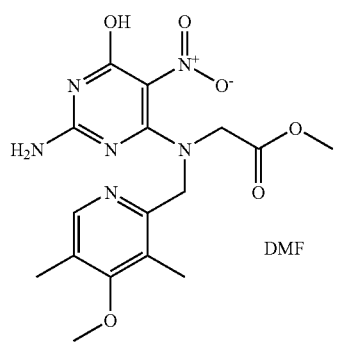

To a mixture of N,N-diisopropylethylamine (3.86 mL) and methyl 2-[(4-methoxy-3,5-dimethyl-pyridin-2-yl)methylamino]acetate (Intermediate 10)(2.38 g) in DMF (50 mL) was added solid 2-amino-4-chloro-5-nitro-6-hydroxypyrimidine (1.9 g)(prepared as described in Justus Liebigs Annalen der Chemie (1964), 677, 113-126). The yellow solution was stirred at ambient temperature for 2 hours. The reaction mixture was evaporated to dryness and the residue partitioned between DCM and saturated aqueous sodium bicarbonate solution. The organic layer was separated, dried over magnesium sulphate, filtered and the filtrate evaporated to dryness to give Intermediate 24 as a yellow solid (3.65 g). NMR shows the presence of 1 equivalent of DMF; $^1$H NMR spectrum (400 MHz, DMSO-d$_6$) δ 2.09 (3H, s), 2.19 (3H, s), 2.75 (3H, s), 2.90 (3H, s), 3.62 (3H, s), 3.72 (3H, s), 4.15 (2H, s), 4.63 (2H, s), 6.79-7.13 (2H, br), 7.97 (1H, s), 8.14 (1H, s), 10.77 (1H, s); Mass spectrum: (M+H)$^+$ 393.35.

Intermediate 25

Methyl 2-[(2-amino-6-chloro-5-nitro-pyrimidin-4-yl)-[(4-methoxy-3,5-dimethyl-pyridin-2-yl)methyl]amino]acetate

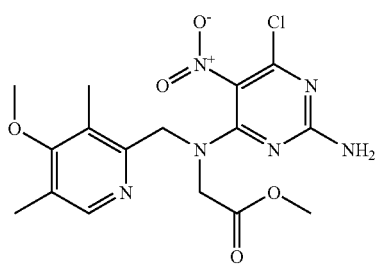

Methyl-2-[(2-amino-6-hydroxy-5-nitro-pyrimidin-4-yl)-[(4-methoxy-3,5-dimethyl-pyridin-2-yl)methyl]amino]acetate, DMF adduct (Intermediate 24)(2 g) was dissolved in toluene and the solution evaporated to dryness. This procedure was repeated twice again to give methyl-2-[(2-amino-6-hydroxy-5-nitro-pyrimidin-4-yl)-[(4-methoxy-3,5-dimethyl-pyridin-2-yl)methyl]amino]acetate, free of DMF, as a pale brown solid. All of this material was added to stirred phosphorus oxychloride (40 mL) and heated to 90° C. for 20 minutes. The mixture was evaporated to dryness and azeotroped with toluene to give Intermediate 25 (1.9 g) as a brown gum; $^1$H NMR spectrum (400 MHz, CDCl$_3$) 2.14 (3H, s), 2.24 (3H, s), 3.73 (3H, s), 3.76 (3H, s), 4.33 (2H, s), 4.65 (2H, s), 5.07 (2H, s), 8.17 (1H, s); Mass spectrum: (M+H)$^+$ 411.33.

Example 9

2-Amino-8-[(4-methoxy-3,5-dimethyl-pyridin-2-yl)methyl]-4-methylsulfanyl-5,7-dihydropteridin-6-one

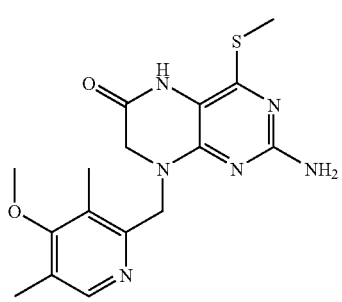

To a solution of methyl 2-[(2-amino-6-methylsulfanyl-5-nitro-pyrimidin-4-yl)-[(4-methoxy-3,5-dimethyl-pyridin-2-yl)methyl]amino]acetate (Intermediate 26)(212 mg) in glacial acetic acid (5 mL) stirred at 70° C. was added iron powder (120 mg). The reaction mixture was heated at 70° C. for 30 minutes then allowed to cool to room temperature. The reaction mixture was filtered, the filtrate evaporated to dryness and azeotroped with toluene to give a brown gum. This material was stirred with 5% methanol in DCM (10 mL) and then filtered to remove iron residues. The filtrate was purified by flash chromatography on silica eluting with an increasingly polar gradient of methanol/DCM (0/100 to 5/95) to give the title compound (52 mg) as a beige solid. $^1$H NMR spectrum (400 MHz, DMSO-d$_6$) 2.11 (6H, s), 2.37 (3H, s), 3.66 (3H, s), 3.88 (2H, s), 4.68 (2H, s), 5.80 (2H, s), 8.07 (1H, s), 9.34 (1H, s); Mass spectrum: (M+H)$^+$ 361.44.

The 2-[(2-amino-6-methylsulfanyl-5-nitro-pyrimidin-4-yl)-[(4-methoxy-3,5-dimethyl-pyridin-2-yl)methyl]amino]acetate (Intermediate 26) used as starting material was made as follows:

Intermediate 26

2-[(2-Amino-6-methylsulfanyl-5-nitro-pyrimidin-4-yl)-[(4-methoxy-3,5-dimethyl-pyridin-2-yl)methyl]amino]acetate

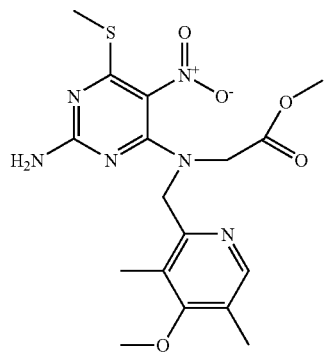

Methyl 2-[(2-amino-6-chloro-5-nitro-pyrimidin-4-yl)-[(4-methoxy-3,5-dimethyl-pyridin-2-yl)methyl]amino]acetate (Intermediate 25)(250 mg) was dissolved in DMA (3 mL) and sodium methanethiolate (43 mg) added. The reaction was stirred at room temperature for 1 hour. The reaction was monitored by LC/MS during the addition of additional portions of sodium methanethiolate, until all starting material was consumed. The reaction mixture was evaporated to dryness and the residue partitioned between ethyl acetate and water. The organic layer was dried with MgSO$_4$, filtered and the filtrate evaporated to dryness. The residue was purified by flash chromatography on silica, eluting with an increasingly polar gradient of ethylacetate/DCM (0/100 to 20/80) to give Intermediate 26 as a yellow foam (218 mg). $^1$H NMR spectrum (400 MHz, CDCl$_3$) 2.06 (3H, s), 2.16 (3H, s), 2.34 (3H, s), 3.63 (3H, s), 3.68 (3H, s), 4.21 (2H, s), 4.58 (2H, s), 4.99 (2H, s), 8.09 (1H, s); Mass spectrum: (M+H)$^+$ 423.13.

Example 10

(7R)-2-Amino-8-[(4-methoxy-3,5-dimethylpyridin-2-yl)methyl]-5-(3-methoxypropyl)-7-methyl-7,8-dihydropteridin-6(5H)-one

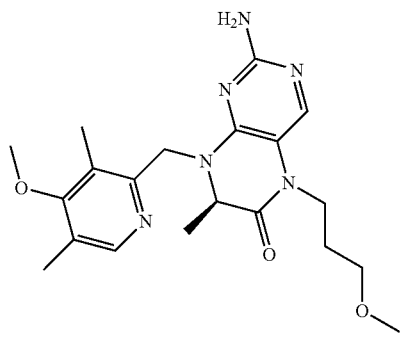

(7R)-2-Amino-8-[(4-methoxy-3,5-dimethylpyridin-2-yl)methyl]-7-methyl-7,8-dihydropteridin-6(5H)-one (Example 2[2])(60 mg, 0.18 mmol) was suspended in THF (10 mL) and the 3-methoxy-1-propanol (70 µL, 0.73 mmol) was added, followed by triphenylphosphine (192 mg, 0.73 mmol) and DIAD (144 µL, 0.73 mmol). The mixture was stirred at room temperature for 2 hours. A further quantity of triphenylphosphine (192 mg, 0.73 mmol) and DIAD (144 µL, 0.73 mmol) were added and stirring continued for 2 hours. A further quantity of triphenylphosphine (192 mg, 0.73 mmol) and DIAD (144 µL, 0.73 mmol) were added and stirring continued overnight. TLC and LCMS analysis showed complete reaction; the mixture was diluted with methanol (5 mL) and loaded onto an SCX-2 column which had been equilibrated with 30% methanol in DCM. The column was eluted with 30% methanol in DCM to remove impurities, then with 30% (3M NH$_3$ in methanol) in DCM to elute the product. The appropriate fractions were concentrated in vacuo; the residue (about 40 mg) was found to be a mixture of N- and O-alkylated products. The sample was dissolved in methanol (5 mL) and 6N HCl (2 mL) was added. The mixture was stirred at room temperature for 2 hours. LCMS showed complete hydrolysis of the O-alkylated material; the desired N-alkylated material was unchanged. The mixture was concentrated in vacuo and the residue was purified by chromatography, eluting with 0 to 5% (10:1 methanol/concentrated NH$_3$ $_{(aqueous)}$) in DCM. The appropriate fractions were concentrated under reduced pressure to give the title compound as a pale yellow gum (20 mg, 27%); $^1$H NMR spectrum (400 MHz, CDCl$_3$) δ 1.36 (3H, d), 1.89 (2H, ddt), 2.17 (3H, s), 2.25 (3H, s), 3.39 (2H, td), 3.75 (3H, s), 3.81 (1H, dd), 3.97 (1H, dd), 4.03 (1H, q), 4.09 (1H, d), 4.67 (2H, s), 5.70 (1H, d), 7.70 (1H, s), 8.18 (1H, s); Mass spectrum: (M+H) 401.

Example 11

Using a similar procedure to that used for the synthesis of Example 3, the compounds shown in Table 5 were prepared from the appropriate 7,8-dihydropteridin-6-one (SM in Table 5) and appropriate alcohol (ROH in Table 5). Either THF or DCM could be used as solvent, as indicated in Table 5. Additional quantities of triphenylphosphine and DIAD were added (typically 4 equivalents of each added every 2 hours) until most of the starting materials were consumed. In all cases excess of these reagents were removed during the SCX purification step (as described for Example 10). Where indicated, to facilitate purification of the required N-alkylated compounds, O-alkylated isomers were hydrolysed at ambient temperature with hydrochloric acid and methanol (as described for Example 10), prior to purification by MPLC or preparative reverse phase HPLC. Purification, in some instances, could also be achieved by fractional crystallisation. The choice of purification method was determined based on ease of separation, as judged from TLC and LCMS analysis.

TABLE 5

| No. and Note | Compound | ROH | Solvent | SM |
|---|---|---|---|---|
| [1] | 2-amino-8-[(4-methoxy-3,5-dimethylpyridin-2-yl)methyl]-5-(3-methoxypropyl)-7,8-dihydropteridin-6(5H)-one | MeO(CH$_2$)$_3$H | THF | Example 2[3] |
| [2] | (7R)-2-amino-8-[(4-methoxy-3,5-dimethylpyridin-2-yl)methyl]-7-methyl-5-(2-phenylethyl)-7,8-dihydropteridin-6(5H)-one | PhCH$_2$CH$_2$OH | THF | Example 2[2] |
| [3] | (7R)-2-amino-8-[(4-methoxy-3,5-dimethylpyridin-2-yl)methyl]-7-methyl-5-(2-piperazin-1-ylethyl)-7,8-dihydropteridin-6(5H)-one | | THF | Example 2[2] |
| [4] | (7R)-2-amino-5-(2,2-difluoroethyl)-8-[(4-methoxy-3,5-dimethylpyridin-2-yl)methyl]-7-methyl-7,8-dihydropteridin-6(5H)-one | CHF$_2$CH$_2$OH | THF | Example 2[2] |

TABLE 5-continued

| No. and Note | Compound | ROH | Solvent | SM |
|---|---|---|---|---|
| [5] | 2-amino-8-[(4-methoxy-3,5-dimethylpyridin-2-yl)methyl]-5-(3-methylbutyl)-7,8-dihydropteridin-6(5H)-one | isopentanol (3-methyl-1-butanol) | THF | Example 2[3] |
| [6] | 2-amino-4-chloro-8-[(4-methoxy-3,5-dimethylpyridin-2-yl)methyl]-5-(3-methylbutyl)-7,8-dihydropteridin-6(5H)-one | isopentanol (3-methyl-1-butanol) | DCM | Example 8 |
| [7] | (7R)-2-amino-8-[(4-methoxy-3,5-dimethylpyridin-2-yl)methyl]-7-methyl-5-(3-methylbutyl)-7,8-dihydropteridin-6(5H)-one | isopentanol (3-methyl-1-butanol) | DCM | Example 2[2] |
| [8] | (7R)-2-amino-8-[(4-methoxy-3,5-dimethylpyridin-2-yl)methyl]-7-methyl-5-propyl-7,8-dihydropteridin-6(5H)-one | $CH_3(CH_2)_2OH$ | DCM | Example 2[2] |

TABLE 5-continued

| No. and Note | Compound | ROH | Solvent | SM |
|---|---|---|---|---|
| [9] | (7R)-2-amino-5-benzyl-8-[(4-methoxy-3,5-dimethylpyridin-2-yl)methyl]-7-methyl-7,8-dihydropteridin-6(5H)-one | PhCH$_2$OH | THF | Example 2[2] |
| [10] | (7R)-2-amino-5-(cyclopropylmethyl)-8-[(4-methoxy-3,5-dimethylpyridin-2-yl)methyl]-7-methyl-7,8-dihydropteridin-6(5H)-one | | THF | Example 2[2] |
| [11] | (7R)-2-amino-8-[(4-methoxy-3,5-dimethylpyridin-2-yl)methyl]-7-methyl-5-(2-pyrrolidin-1-ylethyl)-7,8-dihydropteridin-6(5H)-one | | THF | Example 2[2] |

TABLE 5-continued

| No. and Note | Compound | ROH | Solvent | SM |
|---|---|---|---|---|
| [12] | (7R)-2-amino-5-[2-(dimethylamino)-2-methylpropyl]-8-[(4-methoxy-3,5-dimethylpyridin-2-yl)methyl]-7-methyl-7,8-dihydropteridin-6(5H)-one 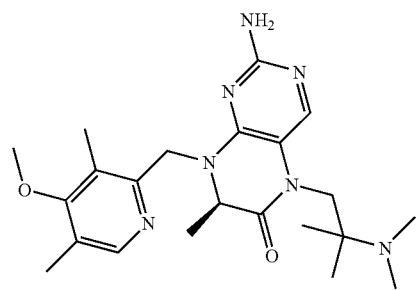 | 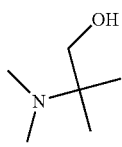 | DCM | Example 2[2] |
| [13] | (7R)-2-amino-5-[3-(dimethylamino)propyl]-8-[(4-methoxy-3,5-dimethylpyridin-2-yl)methyl]-7-methyl-7,8-dihydropteridin-6(5H)-one 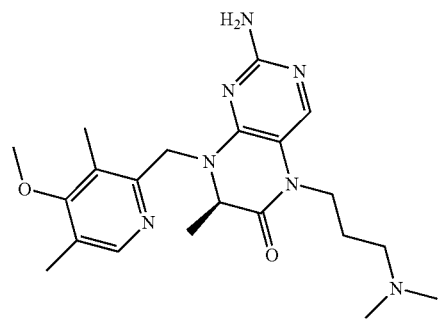 | Me$_2$N(CH$_2$)$_3$OH | THF | Example 2[2] |
| [14] | (7R)-2-amino-8-[(4-methoxy-3,5-dimethylpyridin-2-yl)methyl]-7-methyl-5-(2-morpholin-4-ylethyl)-7,8-dihydropteridin-6(5H)-one 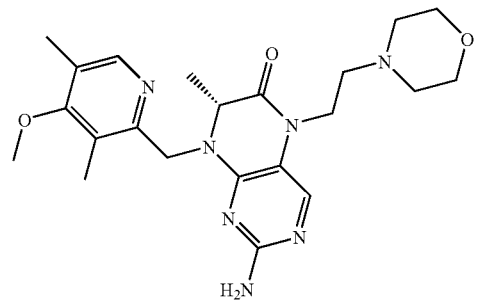 | 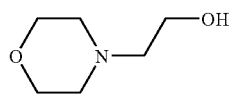 | THF | Example 2[2] |

TABLE 5-continued
| No. and Note | Compound | ROH | Solvent | SM |
|---|---|---|---|---|
| [15] | (7R)-2-amino-8-[(4-methoxy-3,5-dimethylpyridin-2-yl)methyl]-7-methyl-5-(2-pyridin-4-ylethyl)-7,8-dihydropteridin-6(5H)-one 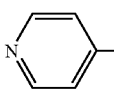 | 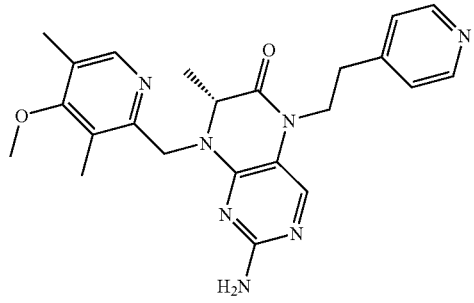 | THF | Example 2[2] |
| [16] | (7R)-2-amino-8-[(4-methoxy-3,5-dimethylpyridin-2-yl)methyl]-7-methyl-5-(2-pyridin-3-ylethyl)-7,8-dihydropteridin-6(5H)-one 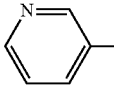 | 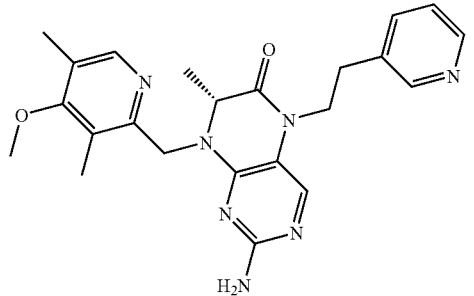 | THF | Example 2[2] |
| [17] | (7R)-2-amino-8-[(4-methoxy-3,5-dimethylpyridin-2-yl)methyl]-7-methyl-5-(3-pyridin-3-ylpropyl)-7,8-dihydropteridin-6(5H)-one 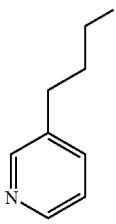 | 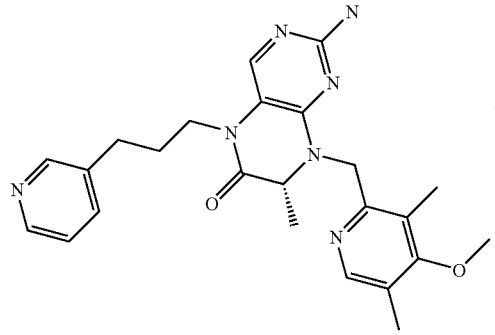 | THF | Example 2[2] |

TABLE 5-continued

| No. and Note | Compound | ROH | Solvent | SM |
|---|---|---|---|---|
| [18] | 2-amino-4-chloro-8-[(4-methoxy-3,5-dimethylpyridin-2-yl)methyl]-5-(2-pyridin-3-ylethyl)-7,8-dihydropteridin-6(5H)-one | pyridin-3-yl-CH2CH2-OH | DCM/THF (1:1) | Example 8 |
| [19] | 2-amino-8-[(4-methoxy-3,5-dimethylpyridin-2-yl)methyl]-5-propyl-7,8-dihydropteridin-6(5H)-one | $CH_3(CH_2)_2OH$ | DCM | Example 2[3] |
| [20] | (7R)-2-amino-8-[(4-methoxy-3,5-dimethylpyridin-2-yl)methyl]-7-methyl-5-[2-(2-oxoimidazolidin-1-yl)ethyl]-7,8-dihydropteridin-6(5H)-one | 2-oxoimidazolidin-1-yl-CH2CH2-OH | THF | Example 2[2] |

TABLE 5-continued

| No. and Note | Compound | ROH | Solvent | SM |
|---|---|---|---|---|
| [21] | (7R)-2-amino-8-[(4-methoxy-3,5-dimethylpyridin-2-yl)methyl]-7-methyl-5-[2-(2-oxopyrrolidin-1-yl)ethyl]-7,8-dihydropteridin-6(5H)-one 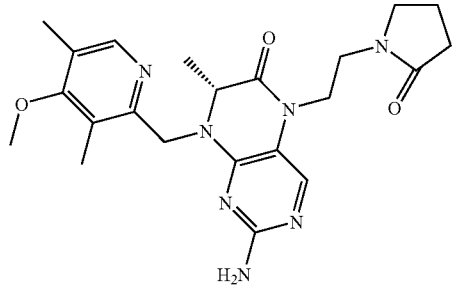 |  | THF | Example 2[2] |
| [22] | 2-amino-5-benzyl-4-chloro-8-[(4-methoxy-3,5-dimethylpyridin-2-yl)methyl]-7,8-dihydropteridin-6(5H)-one 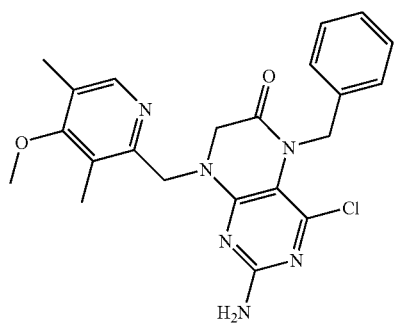 | PhCH$_2$OH | THF | Example 8 |
| [23] | 2-amino-4-chloro-8-[(4-methoxy-3,5-dimethylpyridin-2-yl)methyl]-5-propyl-7,8-dihydropteridin-6(5H)-one 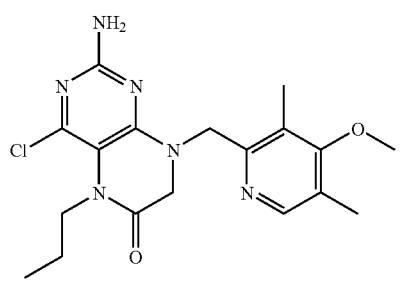 | CH$_3$(CH$_2$)$_2$OH | THF | Example 8 |

TABLE 5-continued

| No. and Note | Compound | ROH | Solvent | SM |
|---|---|---|---|---|
| [24] | 2-amino-4-chloro-8-[(4-methoxy-3,5-dimethylpyridin-2-yl)methyl]-5-(2-phenylethyl)-7,8-dihydropteridin-6(5H)-one | PhCH$_2$CH$_2$OH | THF | Example 8 |

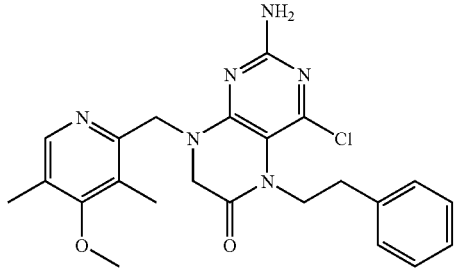

Notes for Table 5

Following SCX purification the products were further purified as follows, and gave the characterising data shown below:

[1] Purification was achieved by MPLC on silica eluting with 2% to 10% methanol in DCM; $^1$H NMR spectrum (400 MHz, DMSO-d$_6$) δ 1.74-1.80 (2H, m), 2.19 (3H, s), 2.21 (3H, s), 3.24 (3H, s), 3.37 (2H, t), 3.74 (3H, s), 3.85 (2H, t), 4.11 (2H, s), 4.78 (2H, s), 5.86 (2H, s), 7.62 (1H, s), 8.15 (1H, s); Mass spectrum: (M+H)$^+$ 387.

[2] The crude product was stirred in 6N HCl/methanol for 2 hours, concentrated under reduced pressure and then purified by MPLC on silica eluting with 0% to 10% methanol in DCM; $^1$H NMR spectrum (400 MHz, CDCl$_3$) δ 1.33 (3H, d), 2.16 (3H, s), 2.25 (3H, s), 2.92 (2H, m), 3.75 (3H, s), 3.84-3.94 (1H, m), 3.99-4.15 (3H, m), 4.68 (2H, s), 5.69 (1H, d), 7.16-7.32 (5H, m), 7.56 (1H, s), 8.18 (1H, s); Mass spectrum: (M+H)$^+$ 433.

[3] The crude product was stirred in concentrated HCl (37%)(1 mL) and methanol (5 mL) for 2 hours, then concentrated under reduced pressure and purified by MPLC on silica eluting with 2% to 20% methanol in DCM; $^1$H NMR spectrum (400 MHz, CDCl$_3$) δ 1.36 (3H, d), 2.17 (3H, s), 2.25 (3H, s), 2.40-2.48 (2H, m), 2.53-2.60 (4H, m), 2.84-2.89 (4H, m), 3.75 (3H, s), 3.80-3.85 (1H, m), 4.00-4.14 (3H, m), 4.67 (2H, s), 5.70 (1H, d), 7.69 (1H, s), 8.18 (1H, s); Mass spectrum: (M+H)$^+$ 441.

[4] The crude product was stirred in 6N HCl/methanol for 2 hours, concentrated under reduced pressure and then purified by MPLC on silica eluting with 0% to 10% methanol in DCM; $^1$H NMR spectrum (400 MHz, CDCl$_3$) δ 1.38 (3H, d), 2.18 (3H, s), 2.25 (3H, s), 3.76 (3H, s), 3.86-3.95 (1H, m), 4.08-4.16 (2H, m), 4.31-4.40 (1H, m), 4.72 (2H, s), 5.69 (1H, d), 5.85-6.16 (1H, m), 7.74 (1H, s), 8.18 (1H, s); Mass spectrum: (M+H)$^+$ 393.

[5] Purification was achieved by MPLC on silica eluting with 0% to 3% [10:1 methanol/concentrated NH$_3$ (aqueous)] in ethyl acetate. The resulting material was recrystallised twice from ethyl acetate/isohexane; $^1$H NMR spectrum (400 MHz, CDCl$_3$) δ 0.96 (3H, s), 0.98 (3H, s), 1.51 (2H, m), 1.66 (1H, m), 2.23 (3H, s), 2.24 (3H, s), 3.77 (3H, s), 3.82 (2H, m), 4.14 (2H, s), 4.83 (2H, s), 5.09 (2H, s), 7.46 (1H, s), 8.17 (1H, s); Mass spectrum: (M+H)$^+$ 385.

[6] Purification was achieved by MPLC on silica eluting with 50% to 60% ethyl acetate/isohexane. The resulting material was recrystallised from ethyl acetate/isohexane; $^1$H NMR spectrum (400 MHz, CDCl$_3$) δ 0.87 (6H, d), 1.39 (2H, ddd), 1.49 (2H, ddd), 2.20 (3H, s), 2.24 (3H, s), 3.76 (3H, s), 3.93 (2H, s), 4.12 (2H, ddd), 4.72 (2H, s), 4.77 (2H, s), 8.14 (1H, s); Mass spectrum: (M+H)$^+$ 419, 421.

[7] Purification was achieved by MPLC on silica eluting with 0% to 3% [10:1 methanol/concentrated NH$_3$ (aqueous)] in ethyl acetate. The resulting material was stirred in 6N HCl/methanol for 2 hours, then concentrated under reduced pressure and purified by MPLC on silica eluting with 0% to 3% [10:1 methanol/concentrated NH$_3$ (aqueous)] in ethyl acetate; $^1$H NMR spectrum (400 MHz, CDCl$_3$) δ 0.95 (6H, d), 1.36 (3H, d), 1.48 (2H, dddd), 1.64 (1H, m), 2.16 (3H, s), 2.25 (3H, s), 3.74 (1H, ddd), 3.86 (1H, ddd), 4.03 (1H, q), 4.10 (1H, d), 4.86 (2H, s), 5.70 (1H, d), 7.55 (1H, s), 8.18 (1H, s); Mass spectrum: (M+H)$^+$ 399.

[8] Purification was achieved by MPLC on silica eluting with 0% to 3% [10:1 methanol/concentrated NH$_3$ (aqueous)] in DCM; $^1$H NMR spectrum (400 MHz, CDCl$_3$) δ 0.93 (3H, t), 1.37 (3H, d), 1.65 (2H, tq), 2.16 (3H, s), 2.25 (3H, s), 3.70 (1H, ddd), 3.75 (3H, s), 3.84 (1H, ddd), 4.03 (1H, q), 4.09 (1H, d), 4.75 (2H, s), 5.71 (1H, d), 7.57 (1H, s), 8.18 (1H, s); Mass spectrum: (M+H)$^+$ 371.

[9] The crude product was stirred in 6N HCl/methanol for 16 hours, concentrated under reduced pressure and then purified by MPLC on silica eluting with 0% to 7% [10:1 methanol/concentrated NH$_3$ (aqueous)] in ethyl acetate. The resulting material was recrystallised from ethyl acetate/isohexane; $^1$H NMR spectrum (400 MHz, CDCl$_3$) δ 1.51 (3H, d), 2.19 (3H, s), 2.26 (3H, s), 3.77 (3H, s), 4.16 (1H, d), 4.24 (1H, q), 4.75 (1H, d), 5.00 (2H, s), 5.30 (1H, d), 5.71 (1H, d), 7.18 (2H, d), 7.25 (1H, dd), 7.32 (2H, dd), 7.39 (1H, s), 8.20 (1H, s); Mass spectrum: (M+H)$^+$ 419.

[10] The crude product was stirred in 6N HCl/methanol for 16 hours, concentrated under reduced pressure and then purified by MPLC on silica eluting with 0% to 7% [10:1 methanol/concentrated NH$_3$ (aqueous)] in ethyl acetate; $^1$H NMR spectrum (400 MHz, CDCl$_3$) δ 0.36 (1H, m), 0.41 (1H, m), 0.50 (2H, m), 1.11 (1H, m), 1.38 (3H, d), 2.17 (3H, s), 2.25 (3H, s), 3.63 (1H, dd), 3.75 (3H, s), 3.85 (1H, dd), 4.03 (1H, q), 4.11 (1H, d), 4.78 (2H, s), 5.72 (1H, d), 7.69 (1H, s), 8.18 (1H, s); Mass spectrum: (M+H)$^+$ 383.

[11] The crude product was stirred in 6N HCl/methanol for 16 hours, concentrated under reduced pressure and then purified by MPLC on silica eluting with 0% to 5% [10:1 methanol/concentrated NH$_3$ (aqueous)] in DCM; $^1$H NMR spectrum (400 MHz, CDCl$_3$) δ 1.36 (3H, d), 1.77 (4H, m), 2.16 (3H, s), 2.25 (3H, s), 2.58 (4H, m), 2.68 (2H, ddd), 3.75 (3H, s), 3.86 (1H, ddd), 4.03 (1H, q), 4.04 (1H, ddd), 4.08 (1H, d), 4.63 (2H, s), 5.70 (1H, d), 7.70 (1H, s), 8.18 (1H, s); Mass spectrum: (M+H)$^+$ 426.

[12] The crude product was purified by MPLC on silica eluting with 0% to 7% [10:1 methanol/concentrated NH$_3$ (aqueous)] in DCM; $^1$H NMR spectrum (400 MHz, CDCl$_3$) δ 1.01 (6H, s), 1.33 (3H, d), 2.16 (3H, s), 2.25 (3H, s), 2.30 (6H, s), 3.74 (3H, s), 3.90 (2H, br.s), 3.99 (1H, q), 4.08 (1H, d), 4.62 (2H, s), 5.69 (1H, d), 8.03 (1H, s), 8.18 (1H, s); Mass spectrum: (M+H)$^+$ 428.

[13] The crude product was stirred in 6N HCl/methanol for 2 hours, then concentrated under reduced pressure and purified by MPLC on silica eluting with 0% to 5% [10:1 methanol/concentrated NH$_3$ (aqueous)] in DCM; $^1$H NMR spectrum (400 MHz, CDCl$_3$) δ 1.36 (3H, d), 1.80 (2H, ddt), 2.17 (3H, s), 2.23 (6H, s), 2.25 (3H, s), 2.33 (2H, td), 3.75 (3H, s), 3.79 (1H, dt), 3.93 (1H, dt), 4.03 (1H, q), 4.09 (2H, d), 4.65 (2H, s), 5.70 (1H, d), 7.70 (1H, s), 8.18 (1H, s); Mass spectrum: (M+H)$^+$ 414.

[14] The crude product was stirred in 6N HCl/methanol for 16 hours, then concentrated under reduced pressure and purified by MPLC on silica eluting with 0% to 5% [10:1 methanol/concentrated NH$_3$ (aqueous)] in DCM. Further purification was by preparative reverse-phase HPLC, eluting with 20% to 40% acetonitrile in water containing 1% aqueous ammonia (d=0.88) solution; $^1$H NMR spectrum (400 MHz, CDCl$_3$) δ 1.37 (3H, d), 2.17 (3H, s), 2.25 (3H, s), 2.51 (4H, m), 2.56 (2H, dd), 3.66 (4H, m), 3.76 (3H, s), 3.84 (1H, m), 4.04 (1H, m), 4.04 (1H, q), 4.10 (1H, d), 4.64 (2H, s), 5.70 (1H, d), 7.67 (1H, s), 8.18 (1H, s); Mass spectrum: (M+H)$^+$ 442.

[15] Purification was achieved by MPLC on silica eluting with 0% to 6% [10:1 methanol/concentrated NH$_3$ (aqueous)] in ethyl acetate; $^1$H NMR spectrum (400 MHz, CDCl$_3$) δ1.32 (3H, d), 2.16 (3H, s), 2.25 (3H, s), 2.92 (2H, t), 3.76 (3H, s), 4.03 (1H, q), 4.05 (1H, dd), 4.08 (1H, d), 4.12 (1H, dd), 4.65 (2H, s), 5.68 (1H, d), 7.14 (2H, dd), 7.60 (1H, s), 8.18 (1H, s), 8.50 (2H, dd); Mass spectrum: (M+H) 434.

[16] The crude product was stirred in 6N HCl/methanol for 5 hours then concentrated under reduced pressure and purified by MPLC on silica eluting with 0% to 6% [10:1 methanol/concentrated NH$_3$ (aqueous)] in ethyl acetate. Further purification was carried out by MPLC on silica eluting with 0% to 5% [10:1 methanol/concentrated NH$_3$ (aqueous)] in DCM; $^1$H NMR spectrum (400 MHz, CDCl$_3$) δ 1.31 (3H, d), 2.16 (3H, s), 2.25 (3H, s), 2.94 (2H, t), 3.76 (3H, s), 3.96 (1H, dd), 4.01 (1H, q), 4.08 (1H, d), 4.14 (1H, dd), 4.66 (2H, s), 5.68 (1H, d), 7.20 (1H, ddd), 7.57 (1H, ddd), 7.59 (1H, s), 8.18 (1H, s), 8.45 (1H, d), 8.47 (1H, dd); Mass spectrum: (M+H)$^+$ 434.

[17] The crude product was stirred in 6N HCl/methanol for 5 hours, then concentrated under reduced pressure and purified by MPLC on silica eluting with 0% to 6% [10:1 methanol/concentrated NH$_3$ (aqueous)] in ethyl acetate. Further purification was carried out by MPLC on silica eluting with 0% to 5% [10:1 methanol/concentrated NH$_3$ (aqueous)] in DCM; $^1$H NMR spectrum (400 MHz, CDCl$_3$) δ 1.37 (3H, d), 1.95 (2H, m), 2.16 (3H, s), 2.24 (3H, s), 2.67 (2H, t), 3.74 (3H, s), 3.81 (1H, ddd), 3.91 (1H, ddd), 4.06 (1H, q), 4.09 (1H, d), 4.64 (2H, s), 5.69 (1H, d), 7.21 (1H, ddd), 7.50 (1H, s), 7.51 (1H, ddd), 8.17 (1H, s), 8.45 (1H, s), 8.45 (2H, dd); Mass spectrum: (M+H)$^+$ 448.

[18] The crude product was purified by MPLC on silica eluting with 0% to 2% [10:1 methanol/concentrated NH$_3$ (aqueous)] in ethyl acetate. Further purification was carried out by MPLC on silica eluting with 0% to 2% [10:1 methanol/concentrated NH$_3$ (aqueous)] in DCM $^1$H NMR spectrum (400 MHz, CDCl$_3$) δ 2.20 (3H, s), 2.24 (3H, s), 2.91 (2H, t), 3.77 (3H, s), 3.97 (2H, s), 4.33 (2H, t), 4.72 (2H, s), 4.74 (2H, s), 7.17 (1H, dd), 7.50 (1H, dd), 8.13 (1H, s), 8.37 (1H, d), 8.44 (1H, dd); Mass spectrum: (M+H)$^+$ 454, 456.

[19] The crude product was purified by MPLC on silica eluting with 0% to 3% [10:1 methanol/concentrated NH$_3$ (aqueous)] in ethyl acetate. The resulting material was recrystallised from ethyl acetate/isohexane; $^1$H NMR spectrum (400 MHz, DMSO-d$_6$) δ 0.89 (3H, t), 1.56 (2H, tq), 2.19 (3H, s), 2.20 (3H, s), 3.74 (3H, s), 3.77 (2H, t), 4.10 (2H, s), 4.78 (2H, s), 5.84 (2H, s), 7.62 (1H, s), 8.15 (1H, s); Mass spectrum: (M+H)$^+$ 357.

[20] Purified by preparative reverse-phase HPLC, eluting with 20% to 40% acetonitrile in water containing 1% aqueous ammonia (d=0.88); $^1$H NMR spectrum (400 MHz, CDCl$_3$) δ 1.29 (3H, d), 2.11 (3H, s), 2.18 (3H, s), 3.22-3.35 (3H, m), 3.36-3.53 (2H, m), 3.69 (3H, s), 3.69-3.77 (1H, m), 3.95-4.15 (4H, m), 4.57 (2H, s), 5.63 (1H, d), 7.70 (1H, s), 8.10 (1H, s); Mass spectrum: (M+H)$^+$ 441.50.

[21] The crude product was stirred in methanol/6N HCl for 16 hours, then concentrated under reduced pressure and purified by preparative reverse-phase HPLC, eluting with 20% to 40% acetonitrile in water containing 1% aqueous ammonia (d=0.88); $^1$H NMR spectrum (400 MHz, DMSO-d$_6$) δ 1.68-1.75 (2H, m), 1.98 (2H, t), 1.15 (3H, d), 2.09 (3H, s), 2.12 (3H, s), 3.18-3.36 (3H, m), 3.38-3.46 (1H, m), 3.69-3.78 (1H, m), 3.83 (1H, q), 4.01 (1H, d), 5.47 (1H, d), 5.89 (2H, s), 7.67 (1H, s), 8.09 (1H, s); Mass spectrum: (M+H)$^+$ 440.52

[22] Purification was achieved by preparative reverse-phase HPLC, eluting with 20% to 40% acetonitrile in water containing 1% aqueous ammonia (d=0.88); $^1$H NMR spectrum (400 MHz, DMSO-d$_6$) δ 2.16 (3H, s), 2.21 (4H, s), 3.75 (3H, s), 4.09 (2H, s), 4.80 (2H, s), 5.27 (2H, s), 6.40 (2H, s), 7.09-7.14 (2H, m), 7.18-7.29 (m, 3H), 8.18 (1H, s); Mass spectrum: (M+H)$^+$ 439.43

[23] The crude product was stirred in methanol/6N HCl for 16 hours, then concentrated under reduced pressure and purified by MPLC on silica eluting with 0% to 10% methanol in DCM; $^1$H NMR spectrum (400 MHz, CDCl$_3$) δ 0.74 (3H, t), 2.14 (3H, s), 2.17 (3H, s), 3.69 (3H, s), 3.88 (2H, s), 3.99 (2H, t), 4.65 (2H, s), 4.71 (2H, s), 8.07 (1H, s); Mass spectrum: (M+H)$^+$ 391.39

[24] The crude product was stirred in methanol/6N HCl for 16 hours, then concentrated under reduced pressure and purified by MPLC on silica eluting with 0% to 10% methanol in DCM; $^1$H NMR spectrum (400 MHz, CDCl$_3$) δ 2.12 (3H, s), 2.17 (3H, s), 2.80 (2H, t), 3.69 (3H, s), 3.86 (2H, s), 4.26 (2H, t), 4.65 (4H, s), 7.05-7.18 (5H, m), 8.07 (1H, s); Mass spectrum: (M+H)$^+$ 453.15

Example 12

{(7R)-2-amino-8-[(4-methoxy-3,5-dimethylpyridin-2-yl)methyl]-6-oxo-5,6,7,8-tetrahydropteridin-7-yl}acetic acid

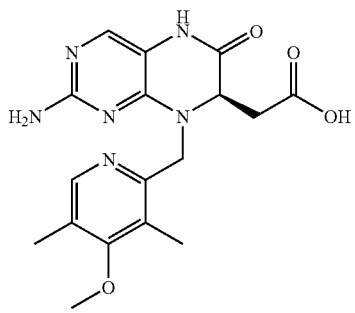

Sodium hydroxide (1 mL, 2M, 2 mmol) was added to a solution of methyl {(7R)-2-amino-8-[(4-methoxy-3,5-dimethylpyridin-2-yl)methyl]-6-oxo-5,6,7,8-tetrahydropteridin-7-yl}acetate (272 mg, 0.26 mmol)(Example 7[3]) in methanol (1 mL) and THF (3 mL). The mixture was stirred for 2 hours and then concentrated under reduced pressure. The solution was diluted with water (1 mL) and made acidic by the addition of acetic acid. This solution was loaded onto an SCX column, washed with water and then methanol and the product was eluted with 2M ammonia in methanol. Thus, the title compound was obtained as a cream solid (169 mg, 65%); $^1$H NMR spectrum (400 MHz, DMSO-d$_6$) δ 2.18 (6H, s), 2.29 (1H, d), 2.38 (1H, d), 3.72 (3H, s), 4.13-4.15 (1H, m), 4.41 (1H, d), 5.49 (1H, d), 5.55 (2H, s), 7.27 (1H, s), 8.13 (1H, s), 9.91 (1H, s); Mass spectrum: (M+H)$^+$ 373.

Example 13

2-{(7R)-2-amino-8-[(4-methoxy-3,5-dimethylpyridin-2-yl)methyl]-6-oxo-5,6,7,8-tetrahydropteridin-7-yl}acetamide

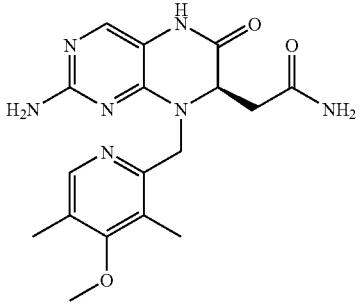

HATU (128 mg, 0.34 mmol) was added to a mixture of 2-{(7R)-2-amino-8-[(4-methoxy-3,5-dimethylpyridin-2-yl)methyl]-6-oxo-5,6,7,8-tetrahydropteridin-7-yl}acetamide (106 mg, 0.28 mmol)(Example 12) and diisopropylethylamine (0.1 mL) in DMF (2 mL). The mixture was stirred for 5 minutes and concentrated aqueous ammonia (0.2 mL) was then added. The reaction mixture was stirred for 16 hours at room temperature. The mixture was partitioned between DCM and water. The organic solution was dried with magnesium sulfate and concentrated under reduced pressure. The residue was purified by preparative reverse phase HPLC (acetonitrile/water/0.1% ammonia). The title compound was obtained as a colourless solid (17 mg, 16%); $^1$H NMR spectrum (400 MHz, DMSO-d$_6$) δ 2.17 (3H, s), 2.19 (3H, s), 3.73 (3H, s), 4.03-4.18 (2H, m), 5.44-5.60 (3H, m), 6.82 (1H, s), 7.27 (1H, s), 7.79 (1H, br), 8.15 (1H, s); Mass spectrum: (M+H)$^+$ 372.

Example 14

Using a similar procedure to that described in Example 10, the compounds shown in Table 4 were prepared by coupling Example 12 with the amines shown as "SM" in Table 4.

TABLE 4

| No. and Note | Compound | SM |
|---|---|---|
| [1] | 2-{(7R)-2-amino-8-[(4-methoxy-3,5-dimethylpyridin-2-yl)methyl]-6-oxo-5,6,7,8-tetrahydropteridin-7-yl}-N-[3-(dimethylamino)propyl]acetamide | Me$_2$N(CH$_2$)$_3$NH$_2$ |

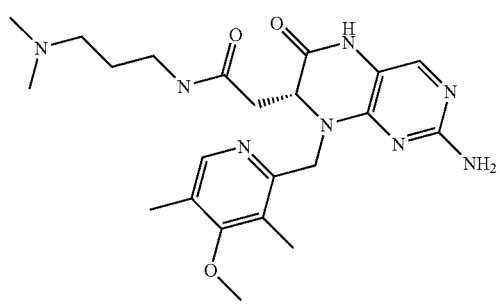

TABLE 4-continued

| No. and Note | Compound | SM |
|---|---|---|
| [2] | 2-{(7R)-2-amino-8-[(4-methoxy-3,5-dimethylpyridin-2-yl)methyl]-6-oxo-5,6,7,8-tetrahydropteridin-7-yl}-N-[2-(dimethylamino)ethyl]acetamide 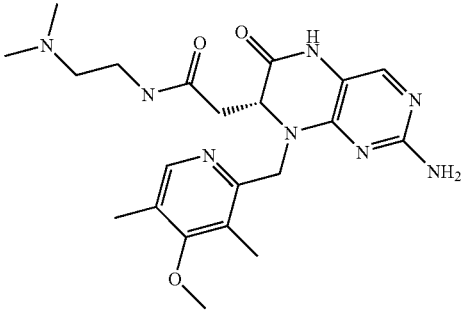 | $Me_2N(CH_2)_2NH_2$ |

Notes for Table 4

The products gave the characterising data shown below:

[1] $^1$H NMR spectrum (400 MHz, DMSO-$d_6$) δ 1.42-1.49 (2H, m), 2.10 (6H, s), 2.12-2.22 (8H, m), 2.55-2.68 (2H, m), 3.00 (2H, q), 3.73 (3H, s), 4.16 (1H, d), 4.22 (1H, t), 5.52 (1H, d), 5.70 (2H, s), 7.34 (1H, s), 8.01 (1H, t), 8.15 (1H, s), 10.16 (1H, s); Mass spectrum: (M+H) 457.

[2] $^1$H NMR spectrum (400 MHz, CDCl$_3$) δ 2.19 (9H, s), 2.23 (3H, s), 2.32 (2H, t), 2.82-2.94 (2H, m), 3.22-3.25 (2H, m), 3.76 (3H, s), 4.33-4.37 (2H, m), 5.52-5.65 (3H, m), 6.92 (1H, s), 7.43 (1H, s), 8.15 (1H, s); Mass spectrum: (M+H)$^+$ 443.

Example 15

2-amino-8-[(4-methoxy-3,5-dimethyl-pyridin-2-yl)methyl]-4-methyl-5,7-dihydropteridin-6-one

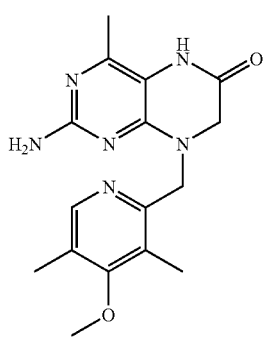

Methyl 2-[(2-amino-6-methyl-5-nitro-pyrimidin-4-yl)-[(4-methoxy-3,5-dimethyl-pyridin-2-yl)methyl]amino]acetate (Intermediate 27) (190 mg, 0.49 mmol) was heated to 70° C. in acetic acid (10 mL) and iron powder (55 mg, 0.97 mmol) was added and the mixture stirred at 70° C. for 1.5 hours. The mixture was poured through Celite®, washing with DCM (200 mL) and the filtrate concentrated in vacuo. NaHCO$_3$ (saturated aqueous, 200 mL) was added and extracted with DCM (3×100 mL). The organics were combined and concentrated and purified by column chromatography (eluting with 0 to 10% 2M methanolic ammonia in DCM) and appropriate fractions combined to the title compound as a yellow solid (87 mg, 54%); $^1$H NMR spectrum (400 MHz, DMSO-$d_6$) δ2.12 (3H, s), 2.20 (6H, s), 3.74 (3H, s), 3.98 (2H, s), 4.76 (2H, s), 5.67 (2H, s), 8.15 (1H, s), 9.81 (1H, s); Mass spectrum: (M+H)$^+$ 329.

The methyl 2-[(2-amino-6-methyl-5-nitro-pyrimidin-4-yl)-[(4-methoxy-3,5-dimethyl-pyridin-2-yl)methyl]amino] acetate (Intermediate 27) used as a starting material was made as follows:

Intermediate 28

Methyl N-(2-chloro-6-methyl-5-nitropyrimidin-4-yl)-N-[(4-methoxy-3,5-dimethylpyridin-2-yl)methyl]glycinate

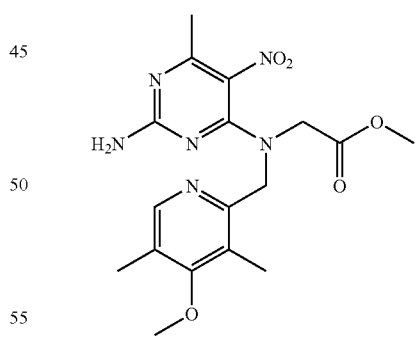

Methyl 2-[(4-methoxy-3,5-dimethyl-pyridin-2-yl)methylamino]acetate (Intermediate 10)(1.15 g, 4.81 mmol) in acetone (10 mL) was added to a stirred mixture of 2,4-dichloro-6-methyl-5-nitro-pyrimidine (1 g, 4.81 mmol) and potassium carbonate (731 mg, 5.29 mmol) in acetone (20 mL) and the mixture stirred at room temperature for 4 hours. The mixture was concentrated in vacuo and water (200 mL) added and extracted with ethyl acetate (3×100 mL). The organics were combined and concentrated in vacuo and the residue was purified by column chromatography (eluting with 0 to 100% ethyl acetate in isohexane) and appropriate fractions combined to yield Intermediate 28 as an orange oil (958 mg, 49%); $^1$H NMR spectrum (400 MHz, CDCl$_3$) δ2.19 (3H, s), 2.24 (3H, s), 2.37 (3H, s), 3.76 (6H, s), 4.41 (2H, s), 4.71 (2H, s), 8.14 (1H, s); Mass spectrum: (M+H)$^+$ 410.

Intermediate 27

Methyl N-(2-amino-6-methyl-5-nitropyrimidin-4-yl)-N-[(4-methoxy-3,5-dimethylpyridin-2-yl)methyl] glycinate

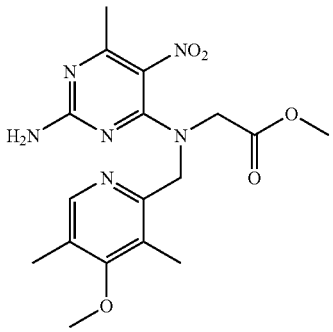

Methyl 2-[(2-chloro-6-methyl-5-nitro-pyrimidin-4-yl)-[(4-methoxy-3,5-dimethyl-pyridin-2-yl)methyl]amino]-acetate (Intermediate 28)(465 mg, 1.13 mmol) was stirred in THF (50 mL) and ammonia (28% in water, 10 mL) was added and the mixture stirred at room temperature overnight. The mixtures were concentrated in vacuo and water (200 mL) was added and extracted with DCM (3×100 mL) and concentration in vacuo yielded Intermediate 27 an orange solid (437 mg, 99%); $^1$H NMR spectrum (400 MHz, DMSO-d$_6$) δ 2.21 (9H, m), 3.63 (3H, d), 3.73 (3H, s), 4.39 (2H, d), 4.98 (2H, d), 7.90 (2H, s), 8.14 (1H, s); Mass spectrum: (M+H)$^+$ 391.

The invention claimed is:
1. A compound of formula I:

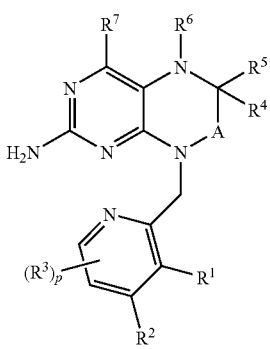

I wherein:
$R^1$, $R^2$ and $R^3$ are independently selected from H, halo, cyano, nitro and a group of the formula:

—$X^1$—$R^8$, wherein $X^1$ is a direct bond, O, S or $NR^{8a}$,
wherein $R^{8a}$ is H or $C_{1-6}$alkyl, and $R^8$ is selected from H, $C_{1-6}$alkyl, $C_{2-6}$alkenyl, $C_{3-7}$cycloalkyl and $C_{2-6}$alkynyl, and wherein $R^1$, $R^2$ and $R^3$ may independently of each other be optionally substituted on carbon by one or more substituents selected from halo, hydroxy, amino, N—($C_{1-6}$alkyl)amino, N,N—($C_{1-6}$alkyl)$_2$amino, $C_{1-6}$alkoxy, $C_{3-7}$cycloalkyl, carbamoyl, N—($C_{1-6}$alkyl)carbamoyl and N,N—($C_{1-6}$alkyl)$_2$carbamoyl;

p is 1 or 2;
A is $CR^{10}R^{11}$;
$R^4$ and $R^{10}$ are independently selected from H, $C_{1-6}$alkyl, $C_{2-6}$alkenyl and $C_{2-6}$alkynyl,
wherein $R^4$ and $R^{10}$ may, independently of each other, be optionally substituted on carbon by halo, hydroxy, amino, $C_{1-6}$alkoxy, N—($C_{1-6}$alkyl)amino or N,N—($C_{1-6}$alkyl )$_2$amino;

$R^5$ and $R^{11}$ are independently selected from H, cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, N—($C_{1-4}$alkoxy)carbamoyl, N—($C_{1-4}$alkyl)-N—($C_{1-4}$alkoxy)carbamoyl, $C_{1-6}$alkoxycarbonyl, $C_{1-6}$alkylsulfonylaminocarbonyl, carbocyclyl-$X^2$—, heterocyclyl-$X^3$— and heteroaryl-$X^4$—,
wherein $R^5$ and $R^{11}$ may independently of each other be optionally substituted on carbon by one or more $R^{13}$;
and wherein if any of said heterocyclyl or heteroaryl contains an —NH— moiety that nitrogen may be optionally substituted by a group selected from $R^{14}$,
and wherein any heterocyclyl group within $R^5$ and $R^{11}$ may optionally bear 1 or 2 oxo or thioxo substituents;
and wherein any carbocyclyl, heterocyclyl or heteroaryl group within $R^5$ and $R^{11}$ may optionally bear a $C_{1-3}$alkylenedioxy group;
or $R^4$ and $R^5$ together form oxo (=O);
or $R^{10}$ and $R^{11}$ together form oxo (=O);
or one of the following pairs of substituents (i) $R^4$ and $R^6$ or (ii) $R^4$ and $R^{10}$ together form a bond;

$R^6$ is selected from H, $C_{1-6}$alkyl, $C_{2-6}$alkenyl, $C_{2-6}$alkynyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, carbocyclyl-$X^5$—, heterocyclyl-$X^6$— and heteroaryl-$X^7$—,
wherein $X^5$, $X^6$ and $X^7$ are independently selected from a direct bond, —C(O)—, —N($R^{12}$)C(O)— and —SO$_2$—;
wherein $R^{12}$ is selected from hydrogen and $C_{1-4}$alkyl,
and wherein $R^6$ may be optionally substituted on carbon by one or more $R^{16}$;
and wherein if any of said heterocyclyl or heteroaryl contains an —NH— moiety that nitrogen may be optionally substituted by a group selected from $R^{17}$,
and wherein any heterocyclyl group within $R^6$ may optionally bear 1 or 2 oxo or thioxo substituents;
and wherein any carbocyclyl, heterocyclyl or heteroaryl group within $R^6$ may optionally bear a $C_{1-3}$alkylenedioxy group;

$R^7$ is selected from H, halo, hydroxy, trifluoromethoxy, mercapto, $C_{1-6}$alkyl, $C_{2-6}$alkenyl, $C_{2-6}$alkynyl, $C_{1-6}$alkoxy, $C_{1-6}$alkylS(O)$_a$ wherein a is 0 to 2,
wherein $R^7$ may be optionally substituted on carbon by one or more $R^{15}$;

$R^{13}$, $R^{15}$ and $R^{16}$ are independently selected from halo, nitro, cyano, hydroxy, trifluoromethoxy, amino, carboxy, carboxyamino, carbamoyl, mercapto, sulfamoyl, ureido, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$ alkyl)$_2$amino, C$_{1-6}$alkanoylamino, N—(C$_{1-6}$alkyl)carbamoyl, N,N—(C$_{1-6}$alkyl)$_2$carbamoyl, N'—(C$_{1-6}$alkyl)ureido, N',N'—(C$_{1-6}$alkyl)$_2$ureido, N,N',N'—(C$_{1-6}$alkyl)$_3$ureido, C$_{1-6}$alkylS(O)$_a$ wherein a is 0 to 2, C$_{1-6}$alkoxycarbonyl, N—(C$_{1-6}$alkyl)sulfamoyl, N,N—(C$_{1-6}$alkyl)$_2$sulfamoyl, C$_{1-6}$alkylsulfonylamino, carbocyclyl-X$^8$—, heterocyclyl-X$^9$— and heteroaryl-X$^{10}$—, and wherein R$^{13}$, R$^{15}$ and R$^{16}$ may be optionally substituted on carbon by one or more R$^{18}$, and wherein if said heterocyclyl or heteroaryl contains an —NH— moiety that nitrogen may be optionally substituted by a group selected from R$^{19}$, and wherein any heterocyclyl group within R$^{13}$, R$^{15}$ and R$^{16}$ may optionally bear 1 or 2 oxo or thioxo substituents, and wherein any carbocyclyl, heterocyclyl or heteroaryl group within R$^{13}$, R$^{15}$ and R$^{16}$ may optionally bear a C$_{1-3}$alkylenedioxy group;

R$^{14}$, R$^{17}$ and R$^{19}$ are independently selected from C$_{1-6}$alkyl, C$_{1-6}$alkanoyl, C$_{1-6}$alkylsulfonyl, C$_{1-6}$alkoxycarbonyl, carbamoyl, N—(C$_{1-6}$alkyl)carbamoyl, N,N—(C$_{1-6}$alkyl)$_2$carbamoyl, benzyl, benzyloxycarbonyl, benzoyl and phenylsulfonyl;

wherein R$^{14}$, R$^{17}$ and R$^{19}$ independently of each other may be optionally substituted on carbon by one or more R$^{20}$;

X$^2$, X$^3$ and X$^4$ are independently selected from a direct bond, —C(O)— and —N(R$^{22}$)C(O)—;

wherein R$^{22}$ is hydrogen or C$_{1-4}$alkyl;

X$^8$, X$^9$ and X$^{10}$ are independently selected from a direct bond, —O—, —N(R$^{21}$)—, —C(O)—, —N(R$^{22}$)C(O)—, —C(O)N(R$^{23}$)—, —S(O)$_q$—, —SO$_2$N(R$^{24}$)— and —N(R$^{25}$)SO$_2$—;

wherein R$^{21}$, R$^{22}$, R$^{23}$, R$^{24}$ and R$^{25}$ are independently selected from hydrogen or C$_{1-4}$alkyl and q is 0-2;

R$^{18}$ is selected from halo, nitro, cyano, hydroxy, trifluoromethoxy, amino, carboxy, carbamoyl, mercapto, sulfamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulfamoyl, N,N—(C$_{1-6}$alkyl)$_2$sulfamoyl, C$_{1-6}$alkylsulfonylamino, carbocyclyl, heterocyclyl and heteroaryl;

wherein R$^{18}$ may be optionally substituted on carbon by one or more R$^{25}$;

and wherein if any of said heterocyclyl or heteroaryl contains an —NH— moiety that nitrogen may be optionally substituted by a group selected from R$^{26}$;

and wherein any heterocyclyl group within R$^{18}$ may optionally bear 1 or 2 oxo or thioxo substituents;

and wherein any carbocyclyl, heterocyclyl or heteroaryl group within R$^{18}$ may optionally bear a C$_{1-3}$alkylenedioxy group;

R$^{26}$ is selected from C$_{1-6}$alkyl, C$_{1-6}$alkanoyl, C$_{1-6}$alkylsulfonyl, C$_{1-6}$alkoxycarbonyl, carbamoyl, N—(C$_{1-6}$alkyl)carbamoyl, N,N—(C$_{1-6}$alkyl)$_2$carbamoyl, benzyl, benzyloxycarbonyl, benzoyl and phenylsulfonyl;

wherein R$^{26}$ may be optionally substituted on carbon by one or more R$^{27}$; and R$^{20}$, R$^{25}$ and R$^{27}$ are independently selected from halo, nitro, cyano, hydroxy, trifluoromethoxy, trifluoromethyl, amino, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl and N-methyl-N-ethylsulfamoyl;

or an N-oxide thereof;

or a pharmaceutically acceptable salt thereof.

2. A compound according to claim 1, or a pharmaceutically acceptable salt or N-oxide thereof, wherein:

R$^{10}$ is H; and

R$^{11}$ is selected from H, C$_{1-6}$alkyl, C$_{3-7}$cycloalkyl-X$^2$—, phenyl-X$^2$, heterocyclyl-X$^3$— and heteroaryl-X$^4$—, wherein said heteroaryl is a monocyclic 5- or 6-membered heteroaryl ring containing 1, 2 or 3 heteroatoms selected from O, S and N, and said heterocyclyl is a monocyclic 5-, 6- or 7-membered heterocyclyl ring containing 1 or 2 heteroatoms selected from O, S and N, wherein R$^{11}$ may be optionally substituted on carbon by one or more R$^{13}$;

and wherein if any of said heterocyclyl or heteroaryl contains an —NH— moiety that nitrogen may be optionally substituted by a group selected from R$^{14}$, and wherein any heterocyclyl group within R$^{11}$ may optionally bear 1 oxo substituent, and wherein any phenyl or heteroaryl group within R$^{11}$ may optionally bear a C$_{1-3}$alkylenedioxy group;

R$^{13}$ is selected from halo, nitro, cyano, hydroxy, trifluoromethoxy, amino, carboxy, carbamoyl, mercapto, sulfamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulfamoyl, N,N—(C$_{1-4}$alkyl)$_2$sulfamoyl, C$_{3-7}$cycloalkyl, phenyl-, a monocyclic 5- or 6-membered heteroaryl ring containing 1, 2 or 3 heteroatoms selected from O, S and N, and a monocyclic 5-, 6- or 7-membered heterocyclyl ring containing 1 or 2 heteroatoms selected from O, S and N, and wherein R$^{13}$ may be optionally substituted on carbon by one or more R$^{18}$, and wherein if any of said heterocyclyl or heteroaryl contains an —NH— moiety that nitrogen may be optionally substituted by a group selected from R$^{19}$, and wherein any heterocyclyl group within R$^{13}$ may optionally bear 1 oxo substituent;

R$^{14}$ and R$^{19}$ are independently selected from C$_{1-4}$alkyl, C$_{1-4}$alkanoyl, C$_{1-4}$alkylsulfonyl, C$_{1-4}$alkoxycarbonyl, carbamoyl, N—(C$_{1-6}$alkyl)carbamoyl, N,N—(C$_{1-6}$alkyl)$_2$carbamoyl, benzyl, benzyloxycarbonyl and benzoyl;

R$^{18}$ is selected from halo, hydroxy, amino, C$_{1-4}$alkyl, C$_{1-4}$alkoxy, N—(C$_{1-4}$alkyl)amino and N,N—(C$_{1-4}$alkyl)$_2$amino; and X$^2$, X$^3$ and X$^4$ are independently selected from a direct bond, —C(O)— and —N(R$^{22}$)C(O)—, wherein R$^{22}$ is selected from hydrogen and C$_{1-4}$alkyl.

3. A compound according to claim 1, or a pharmaceutically acceptable salt or N-oxide thereof, wherein:

R$^{10}$ is H;

R$^{11}$ is selected from H, C$_{1-6}$alkyl, C$_{3-7}$cycloalkyl-X$^2$—, phenyl-X$^2$, heterocyclyl-X$^3$— and heteroaryl-X$^4$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl, wherein said $C_{3-7}$cycloalkyl is selected from cyclopropyl, cyclobutyl, cyclopentyl and cyclohexyl, and wherein $R^{11}$ may be optionally substituted on carbon by one or more $R^{13}$;

and wherein if any of said heterocyclyl or heteroaryl contains an —NH— moiety that nitrogen may be optionally substituted by a group selected from $R^{14}$, and wherein any heterocyclyl group within $R^{11}$ may optionally bear 1 oxo substituent;

$R^{13}$ is selected from halo, nitro, cyano, hydroxy, trifluoromethoxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl)$_2$sulfamoyl, cyclopropyl, cyclobutyl, cyclopentyl, cyclohexyl, phenyl, a heteroaryl selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and a heterocyclyl selected from azetidinyl, pyrrolidinyl, morpholinyl, piperidinyl and piperazinyl, and wherein $R^{13}$ may be optionally substituted on carbon by one or more $R^{18}$, and wherein if any of said heterocyclyl or heteroaryl contains an —NH— moiety that nitrogen may be optionally substituted by a group selected from $R^{19}$;

and wherein any heterocyclyl group within $R^{13}$ may optionally bear 1 oxo substituent;

$R^{14}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-6}$alkyl)carbamoyl, N,N—($C_{1-6}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^2$, $X^3$ and $X^4$ are independently selected from a direct bond, —C(O)— and —N($R^{22}$)C(O)—, wherein $R^{22}$ is selected from hydrogen and $C_{1-4}$alkyl.

4. A compound according to claim 1, or a pharmaceutically acceptable salt or N-oxide thereof, wherein:

$R^{10}$ is H; and $R^{11}$ is selected from H and $C_{1-6}$alkyl, wherein $R^{11}$ is optionally substituted on carbon by one or more $R^{13}$;

$R^{13}$ is selected from halo, nitro, cyano, hydroxy, trifluoromethoxy, amino, carboxy, carboxyamino, carbamoyl, mercapto, sulfamoyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$ amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulfamoyl, N,N—($C_{1-4}$alkyl )$_2$sulfamoyl, $C_{1-4}$alkylsulfonylamino, phenyl, pyridyl and pyrimidinyl.

5. A compound according to claim 1, or a pharmaceutically acceptable salt or N-oxide thereof, wherein:

$R^6$ is selected from H, $C_{1-6}$alkyl, $C_{3-7}$cycloalkyl-$X^5$—, phenyl-$X^5$—, heterocyclyl-$X^6$— and heteroaryl-$X^7$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl, wherein $X^5$, $X^6$ and $X^7$ are independently selected from a direct bond, —C(O)— and —N($R^{12}$)C(O)—, wherein $R^{12}$ is selected from hydrogen or $C_{1-4}$alkyl, and wherein $R^6$ may be optionally substituted on carbon by one or more $R^{16}$; and wherein if any of said heterocyclyl or heteroaryl contains an —NH— moiety that nitrogen may be optionally substituted by a group selected from $R^{17}$, and wherein any heterocyclyl group within $R^6$ may optionally bear 1 oxo substituent;

$R^{16}$ is selected from halo, cyano, hydroxy, amino, mercapto, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, $C_{1-4}$alkylS())$_a$ wherein a is 0 to 2, $C_{1-4}$alkoxycarbonyl, cyclopropyl-$X^8$—, cyclobutyl-$X^8$—, cyclopentyl-$X^8$—, cyclohexyl-$X^8$—, phenyl-$X^8$—, and heterocyclyl-$X^9$—, wherein said heterocyclyl is selected from azetidinyl, pyrrolidinyl, morpholinyl, piperidinyl and piperazinyl, and heteroaryl-$X^{10}$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl, and wherein $R^{16}$ may be optionally substituted on carbon by one or more $R^{18}$, and wherein if any of said heterocyclyl or heteroaryl contains an —NH— moiety that nitrogen may be optionally substituted by a group selected from $R^{19}$, and wherein any heterocyclyl group within $R^{16}$ may optionally bear 1 oxo substituent;

$R^{17}$ and $R^{19}$ are independently selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)$_2$carbamoyl, benzyl, benzyloxycarbonyl and benzoyl;

$R^{18}$ is selected from halo, hydroxy, amino, $C_{1-4}$alkyl, $C_{1-4}$alkoxy, N—($C_{1-4}$alkyl)amino and N,N—($C_{1-4}$alkyl)$_2$amino; and $X^8$, $X^9$ and $X^{10}$ are independently selected from a direct bond, —O—, —N($R^{21}$)—, —C(O)—, and —S(O)$_q$—, wherein $R^{21}$ is selected from hydrogen and $C_{1-4}$alkyl and q is 0-2.

6. A compound according to claim 1, or a pharmaceutically acceptable salt or N-oxide thereof, wherein:

$R^6$ is selected from H, $C_{1-6}$alkyl, cyclopropyl, cyclobutyl, cyclopentyl, cyclohexyl, phenyl-$C_{1-4}$alkyl, cyclopropyl-$C_{1-4}$alkyl, cyclobutyl-$C_{1-4}$alkyl, cyclopentyl-$C_{1-4}$ alkyl, cyclohexyl-$C_{1-4}$alkyl, azetidinyl-$C_{1-4}$alkyl, pyrrolidinyl-$C_{1-4}$alkyl, morpholinyl-$C_{1-4}$alkyl, piperidinyl- C$_{1-4}$alkyl, imidazolidinyl-C$_{1-4}$alkyl, piperazinyl-C$_{1-4}$alkyl and pyridinyl-C$_{1-4}$alkyl, wherein R$^6$ may be optionally substituted on carbon by one or more substituents selected from halo, hydroxy, amino, C$_{1-4}$alkyl, C$_{1-4}$alkoxy, N—(C$_{1-4}$alkyl)amino and N,N—(C$_{1-4}$alkyl)$_2$amino, and wherein any —NH— in an azetidinyl, pyrrolidinyl, piperidinyl, morpholinyl, imidazolidinyl, piperidinyl or piperazinyl group in R$^6$ is optionally substituted by C$_{1-4}$alkyl, and wherein any azetidinyl, pyrrolidinyl, piperidinyl, morpholinyl, piperidinyl or piperazinyl group in R$^6$ optionally bears 1 oxo substituent.

7. A compound according to claim 5, or a pharmaceutically acceptable salt or N-oxide thereof, wherein:

R$^{10}$ is H;

R$^{11}$ is selected from H and C$_{1-6}$alkyl, wherein R$^{11}$ is optionally substituted on carbon by one or more R$^{13}$; and R$^{13}$ is selected from halo, nitro, cyano, hydroxy, trifluoromethoxy, amino, carboxy, carboxyamino, carbamoyl, mercapto, sulfamoyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulfamoyl, N,N—(C$_{1-4}$alkyl)$_2$sulfamoyl, C$_{1-4}$alkylsulfonylamino, phenyl, pyridyl and pyrimidinyl.

8. A compound according to claim 1, or a pharmaceutically acceptable salt or N-oxide thereof, wherein R$^4$ and R$^5$ together form oxo.

9. A compound according to claim 1, or a pharmaceutically acceptable salt or N-oxide thereof, wherein R$^7$ is chloro.

10. A compound according to claim 1, or a pharmaceutically acceptable salt or N-oxide thereof, wherein:

R$^7$ is chloro; and

R$^4$ and R$^5$ together form oxo.

11. A compound according to claim 1, or a pharmaceutically acceptable salt or N-oxide thereof, wherein:

R$^1$ is selected from halo and C$_{1-3}$alkyl;

R$^2$ is selected from halo, C$_{1-3}$alkoxy and C$_{1-3}$alkylthio;

p is 1; and

R$^3$ is in the meta-position to the pyridyl nitrogen, and is selected from H, halo, hydroxy, C$_{1-4}$alkyl, C$_{1-4}$alkoxy and C$_{1-4}$alkylthio.

12. A compound according to claim 1, or a pharmaceutically acceptable salt or N-oxide thereof, wherein the pyridyl group in formula I is of the formula:

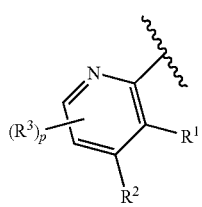

and is selected from 4-methoxy-3,5-dimethylpyridin-2-yl, 4-chloro-3,5-dimethylpyridin-2-yl, 4-chloro-3,5-dimethyl-1-oxypyridin-2-yl, 4-methoxy-3,5-dimethyl-1-oxypyridin-2-yl, 4-bromo-3,5-dimethylpyridin-2-yl, 4-bromo-3,5-dimethyl-1-oxy-pyridin-2-yl, 4-iodo-3,5-dimethyl-1-oxy-pyridin-2-yl, 4-iodo-3,5-dimethylpyridin-2-yl, 3-bromo-4,5,6-trimethoxypyridin-2-yl, 3-chloro-4,5,6-trimethoxypyridin-2-yl, 3,4,5-trimethylpyridin-2-yl, 3,4,5-trimethyl-1-oxypyridin-2-yl, 3,4,5-trimethoxypyridin-2-yl, 6-chloro-4-methoxy-3,5-dimethylpyridin-2-yl, 6-bromo-4-methoxy-3,5-dimethylpyridin-2-yl, 6-chloro-4-methoxy-3,5-dimethyl-1-oxy-pyridin-2-yl, 6-bromo-4-methoxy-3,5-dimethyl-1-oxy-pyridin-2-yl, 6,4-dimethoxy-3,5-dimethylpyridin-2-yl, 6,4-dimethoxy-3,5-dimethyl-1-oxy-pyridin-2-yl, 3-bromo-4,5,6-trimethoxy-1-oxy-pyridin-2-yl and 3-chloro-4,5,6-trimethoxy-1-oxy-pyridin-2-yl.

13. A compound according to claim 1, or a pharmaceutically acceptable salt or N-oxide thereof, wherein the group of the formula:

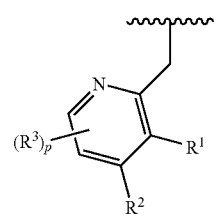

in formula I is of the formula:

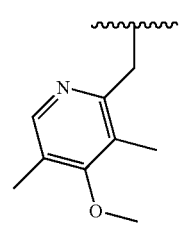

wherein ⁓ indicates the point of attachment to the nitrogen in formula I.

14. A compound according to claim 1, or a pharmaceutically acceptable salt or N-oxide thereof, wherein the pyridyl group in formula I is of the formula:

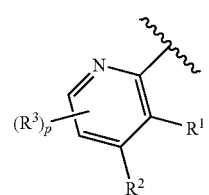

and is selected from 4-methoxy-3,5-dimethylpyridin-2-yl, 4-chloro-3,5-dimethylpyridin-2-yl, 4-chloro-3,5-dimethyl-1-oxypyridin-2-yl, 4-methoxy-3,5-dimethyl-1-oxypyridin-2-yl, 4-bromo-3,5-dimethylpyridin-2-yl, 4-bromo-3,5-dimethyl-1-oxy-pyridin-2-yl, 4-iodo-3,5-dimethyl-1-oxy-pyridin-2-yl, 4-iodo-3,5-dimethylpyridin-2-yl, 3-bromo-4,5,6-trimethoxypyridin-2-yl, 3-chloro-4,5,6-trimethoxypyridin-2-yl, 3,4,5-trimethylpyridin-2-yl, 3,4,5-trimethyl-1-oxypyridin-2-yl, 3,4,5-trimethoxypyridin-2-yl, 6-chloro-4-methoxy-3,5-dimethylpyridin-2-yl, 6-bromo-4-methoxy-3,5-dimethylpyridin-2-yl, 6-chloro-4-methoxy-3,5-dimethyl-1-oxy-pyridin-2-yl, 6-bromo-4-methoxy-3,5-dimethyl-1-oxy-pyridin-2-yl, 6,4-dimethoxy-3,5-dimethylpyridin-2-yl, 6,4-dimethoxy-3,5-dimethyl-1-oxypyridin-2-yl, 3-bromo-4,5,6-trimethoxy-1-oxy-pyridin-2-yl and 3-chloro-4,5,6-trimethoxy-1-oxy-pyridin-2-yl;
R$^7$ is chloro; and
R$^4$ and R$^5$ together form oxo.

15. A compound according to claim 1, or a pharmaceutically acceptable salt or N-oxide thereof, of the formula IF*:

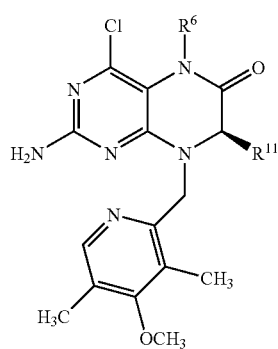

IF* wherein R$^6$ and R$^{11}$ are as defined in claim 1.

16. A compound according to claim 15, or a pharmaceutically acceptable salt or N-oxide thereof, of the formula IF* wherein R$^{11}$ is selected from H and C$_{1-4}$alkyl,
wherein R$^{11}$ is optionally substituted on carbon by one or more R$^{13}$ selected from halo, nitro, cyano, hydroxy, trifluoromethoxy, amino, carboxy, carboxyamino, carbamoyl, mercapto, sulfamoyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulfamoyl, N,N—(C$_{1-4}$alkyl)$_2$sulfamoyl, C$_{1-4}$alkylsulfonylamino, phenyl, pyridyl and pyrimidinyl.

17. A compound according to claim 15, or a pharmaceutically acceptable salt or N-oxide thereof, of the formula IF* wherein R$^6$ is selected from H, C$_{1-6}$alkyl, C$_{3-7}$cycloalkyl-X$^5$—, phenyl-X$^5$—, heterocyclyl-X$^6$— and heteroaryl-X$^7$—,
wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl,
wherein said heterocyclyl is selected from azetidinyl, tetrahydrofuranyl, tetrahydropyranyl, tetrahydrothiopyranyl, pyrrolinyl, pyrrolidinyl, morpholinyl, piperidinyl, piperazinyl, indolinyl and isoindolinyl,
wherein X$^5$, X$^6$ and X$^7$ are independently selected from a direct bond, —C(O)— and —N(R$^{12}$)C(O)—,
wherein R$^{12}$ is selected from hydrogen and C$_{1-4}$alkyl,
and wherein R$^6$ may be optionally substituted on carbon by one or more R$^{16}$;
and wherein if any of said heterocyclyl or heteroaryl contains an —NH— moiety that nitrogen may be optionally substituted by a group selected from R$^7$,
and wherein any heterocyclyl group within R$^6$ may optionally bear 1 oxo substituent;
R$^{16}$ is selected from halo, cyano, hydroxy, amino, mercapto, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, C$_{1-4}$alkylS(O)$_a$ wherein a is 0 to 2, C$_{1-4}$alkoxycarbonyl, cyclopropyl-X$^8$—, cyclobutyl-X$^8$—, cyclopentyl-X$^8$—, cyclohexyl-X$^8$—, phenyl-X$^8$—, and heterocyclyl-X$^9$—,
wherein said heterocyclyl is selected from azetidinyl, pyrrolidinyl, morpholinyl, piperidinyl and piperazinyl, and heteroaryl-X$^{10}$—, wherein said heteroaryl is selected from furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl and pyrazinyl,
and wherein R$^{16}$ may be optionally substituted on carbon by one or more R$^{18}$,
and wherein if any of said heterocyclyl or heteroaryl contains an —NH— moiety that nitrogen may be optionally substituted by a group selected from R$^{19}$,
and wherein any heterocyclyl group within R$^{16}$ may optionally bear 1 oxo substituent;
R$^{17}$ and R$^{19}$ are independently selected from C$_{1-4}$alkyl, C$_{1-4}$alkanoyl, C$_{1-4}$alkylsulfonyl, C$_{1-4}$alkoxycarbonyl, carbamoyl, N—(C$_{1-4}$alkyl)carbamoyl, N,N—(C$_{1-4}$alkyl)$_2$carbamoyl, benzyl, benzyloxycarbonyl and benzoyl;
R$^{18}$ is selected from halo, hydroxy, amino, C$_{1-4}$alkyl, C$_{1-4}$alkoxy, N—(C$_{1-4}$alkyl)amino and N,N—(C$_{1-4}$alkyl)$_2$amino; and
X$^8$, X$^9$ and X$^{10}$ are independently selected from a direct bond, —O—, —N(R$^{21}$)—, —C(O)—, and —S(O)$_q$—, wherein R$^{21}$ is selected from hydrogen or C$_{1-4}$alkyl and q is 0-2.

18. A compound selected from:
(7S)-2-amino-8-[(4-methoxy-3,5-dimethylpyridin-2-yl)methyl]-7-methyl-7,8-dihydropteridin-6(5H)-one;
(7S)-2-amino-8-[(4-methoxy-3,5-dimethylpyridin-2-yl)methyl]-7-propyl-7,8-dihydropteridin-6(5H)-one;
(7R)-2-amino-8-[(4-methoxy-3,5-dimethylpyridin-2-yl)methyl]-7-methyl-7,8-dihydropteridin-6(5H)-one;
2-amino-8-[(4-methoxy-3,5-dimethylpyridin-2-yl)methyl]-7,8-dihydropteridin-6(5H)-one;
(7S)-2-amino-8-[(4-methoxy-3,5-dimethylpyridin-2-yl)methyl]-5,7-dimethyl-7,8-dihydropteridin-6(5H)-one;
(7S)-2-amino-5-ethyl-8-[(4-methoxy-3,5-dimethylpyridin-2-yl)methyl]-7-methyl-7,8-dihydropteridin-6(5H)-one;
(7R)-2-amino-8-[(4-methoxy-3,5-dimethylpyridin-2-yl)methyl]-5,7-dimethyl-7,8-dihydropteridin-6(5H)-one;
2-amino-8-[(4-methoxy-3,5-dimethylpyridin-2-yl)methyl]-5-methyl-7,8-dihydropteridin-6(5H)-one;
(7R)-8-[(4-methoxy-3,5-dimethylpyridin-2-yl)methyl]-7-methyl-5,6,7,8-tetrahydropteridin-2-amine;
(7R)-8-[(4-methoxy-3,5-dimethylpyridin-2-yl)methyl]-5,7-dimethyl-5,6,7,8-tetrahydropteridin-2-amine;
8-[(4-methoxy-3,5-dimethylpyridin-2-yl)methyl]-5-methyl-5,6,7,8-tetrahydropteridin-2-amine;
(7R)-2-amino-8-[(4-methoxy-3,5-dimethyl-pyridin-2-yl)methyl]-7-(2-methylpropyl)-7,8-dihydropteridin-6(5H)-one;
(7R)-2-amino-7-benzyl-8-[(4-methoxy-3,5-dimethyl-pyridin-2-yl)methyl]-7,8-dihydropteridin-6(5H)-one;
methyl{(7R)-2-amino-8-[(4-methoxy-3,5-dimethylpyridin-2-yl)methyl]-6-oxo-5,6,7,8-tetrahydropteridin-7-yl} acetate;
(7R)-2-amino-8-[(4-methoxy-3,5-dimethyl-pyridin-2-yl)methyl]-7-propyl-7,8-dihydropteridin-6(5H)-one;
2-amino-4-chloro-8-[(4-methoxy-3,5-dimethyl-pyridin-2-yl)methyl]-5,7-dihydropteridin-6-one;
2-amino-8-[(4-methoxy-3,5-dimethyl-pyridin-2-yl)methyl]-4-methylsulfanyl-5,7-dihydropteridin-6-one;

(7R)-2-amino-8-[(4-methoxy-3,5-dimethylpyridin-2-yl) methyl]-5-(3-methoxypropyl)-7-methyl-7,8-dihydropteridin-6(5H)-one;

2-amino-8-[(4-methoxy-3,5-dimethylpyridin-2-yl)methyl]-5-(3-methoxypropyl)-7,8-dihydropteridin-6(5H)-one;

(7R)-2-amino-8-[(4-methoxy-3,5-dimethylpyridin-2-yl) methyl]-7-methyl-5-(2-phenylethyl)-7,8-dihydropteridin-6(5H)-one;

(7R)-2-amino-8-[(4-methoxy-3,5-dimethylpyridin-2-yl) methyl]-7-methyl-5-(2-piperazin-1-ylethyl)-7,8-dihydropteridin-6(5H)-one;

(7R)-2-amino-5-(2,2-difluoroethyl)-8-[(4-methoxy-3,5-dimethylpyridin-2-yl)methyl]-7-methyl-7,8-dihydropteridin-6(5H)-one;

2-amino-8-[(4-methoxy-3,5-dimethylpyridin-2-yl)methyl]-5-(3-methylbutyl)-7,8-dihydropteridin-6(5H)-one;

2-amino-4-chloro-8-[(4-methoxy-3,5-dimethylpyridin-2-yl)methyl]-5-(3-methylbutyl)-7,8-dihydropteridin-6(5H)-one;

(7R)-2-amino-8-[(4-methoxy-3,5-dimethylpyridin-2-yl) methyl]-7-methyl-5-(3-methylbutyl)-7,8-dihydropteridin-6(5H)-one;

(7R)-2-amino-8-[(4-methoxy-3,5-dimethylpyridin-2-yl) methyl]-7-methyl-5-propyl-7,8-dihydropteridin-6(5H)-one;

(7R)-2-amino-5-benzyl-8-[(4-methoxy-3,5-dimethylpyridin-2-yl)methyl]-7-methyl-7,8-dihydropteridin-6(5H)-one;

(7R)-2-amino-5-(cyclopropylmethyl)-8-[(4-methoxy-3,5-dimethylpyridin-2-yl)methyl]-7-methyl-7,8-dihydropteridin-6(5H)-one;

(7R)-2-amino-8-[(4-methoxy-3,5-dimethylpyridin-2-yl) methyl]-7-methyl-5-(2-pyrrolidin-1-ylethyl)-7,8-dihydropteridin-6(5H)-one;

(7R)-2-amino-5-[2-(dimethylamino)-2-methylpropyl]-8-[(4-methoxy-3,5-dimethylpyridin-2-yl)methyl]-7-methyl-7,8-dihydropteridin-6(5H)-one;

(7R)-2-amino-5-[3-(dimethylamino)propyl]-8-[(4-methoxy-3,5-dimethylpyridin-2-yl)methyl]-7-methyl-7,8-dihydropteridin-6(5H)-one;

(7R)-2-amino-8-[(4-methoxy-3,5-dimethylpyridin-2-yl) methyl]-7-methyl-5-(2-morpholin-4-ylethyl)-7,8-dihydropteridin-6(5H)-one;

(7R)-2-amino-8-[(4-methoxy-3,5-dimethylpyridin-2-yl) methyl]-7-methyl-5-(2-pyridin-4-ylethyl)-7,8-dihydropteridin-6(5H)-one;

(7R)-2-amino-8-[(4-methoxy-3,5-dimethylpyridin-2-yl) methyl]-7-methyl-5-(2-pyridin-3-ylethyl)-7,8-dihydropteridin-6(5H)-one;

(7R)-2-amino-8-[(4-methoxy-3,5-dimethylpyridin-2-yl) methyl]-7-methyl-5-(3-pyridin-3-ylpropyl)-7,8-dihydropteridin-6(5H)-one;

2-amino-4-chloro-8-[(4-methoxy-3,5-dimethylpyridin-2-yl)methyl]-5-(2-pyridin-3-ylethyl)-7,8-dihydropteridin-6(5H)-one;

2-amino-8-[(4-methoxy-3,5-dimethylpyridin-2-yl)methyl]-5-propyl-7,8-dihydropteridin-6(5H)-one;

(7R)-2-amino-8-[(4-methoxy-3,5-dimethylpyridin-2-yl) methyl]-7-methyl-5-[2-(2-oxoimidazolidin-1-yl) ethyl]-7,8-dihydropteridin-6(5H)-one;

(7R)-2-amino-8-[(4-methoxy-3,5-dimethylpyridin-2-yl) methyl]-7-methyl-5-[2-(2-oxopyrrolidin-1-yl)ethyl]-7,8-dihydropteridin-6(5H)-one;

2-amino-5-benzyl-4-chloro-8-[(4-methoxy-3,5-dimethylpyridin-2-yl)methyl]-7,8-dihydropteridin-6(5H)-one;

2-amino-4-chloro-8-[(4-methoxy-3,5-dimethylpyridin-2-yl)methyl]-5-propyl-7,8-dihydropteridin-6(5H)-one;

2-amino-4-chloro-8-[(4-methoxy-3,5-dimethylpyridin-2-yl)methyl]-5-(2-phenylethyl)-7,8-dihydropteridin-6(5H)-one;

{(7R)-2-amino-8-[(4-methoxy-3,5-dimethylpyridin-2-yl) methyl]-6-oxo-5,6,7,8-tetrahydropteridin-7-yl} acetic acid;

2-{(7R)-2-amino-8-[(4-methoxy-3,5-dimethylpyridin-2-yl)methyl]-6-oxo-5,6,7,8-tetrahydropteridin-7-yl} acetamide;

2-{(7R)-2-amino-8-[(4-methoxy-3,5-dimethylpyridin-2-yl)methyl]-6-oxo-5,6,7,8-tetrahydropteridin-7-yl}-N-[3-(dimethylamino)propyl]acetamide;

2-{(7R)-2-amino-8-[(4-methoxy-3,5-dimethylpyridin-2-yl)methyl]-6-oxo-5,6,7,8-tetrahydropteridin-7-yl}-N-[2-(dimethylamino)ethyl]acetamide; and 2-amino-8-[(4-methoxy-3,5-dimethyl-pyridin-2-yl)methyl]-4-methyl-5,7-dihydropteridin-6-one;

or an N-oxide thereof;

or a pharmaceutically acceptable salt thereof.

19. A pharmaceutical composition which comprises a compound of the formula I, or a pharmaceutically acceptable salt or N-oxide thereof, as defined in claim 1 in association with a pharmaceutically acceptable diluent or carrier.

\* \* \* \* \*